(12) United States Patent
Aebersold et al.

(10) Patent No.: US 6,670,194 B1
(45) Date of Patent: Dec. 30, 2003

(54) RAPID QUANTITATIVE ANALYSIS OF PROTEINS OR PROTEIN FUNCTION IN COMPLEX MIXTURES

(75) Inventors: Rudolf Hans Aebersold, Mercer Island, WA (US); Michael H. Gelb, Seattle, WA (US); Steven P. Gygi, Seattle, WA (US); C. Ronald Scott, Seattle, WA (US); Frantisek Turecek, Seattle, WA (US); Scott A. Gerber, Seattle, WA (US); Beate Rist, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/383,062

(22) Filed: Aug. 25, 1999

Related U.S. Application Data
(60) Provisional application No. 60/097,788, filed on Aug. 25, 1998, and provisional application No. 60/099,113, filed on Sep. 3, 1998.

(51) Int. Cl.[7] .................. C07C 331/16; G01N 33/68
(52) U.S. Cl. .................. 436/173; 436/86; 436/89; 436/120; 436/161; 436/165; 436/166; 436/167; 436/168; 436/171; 436/173; 436/174; 436/175; 436/177; 530/350; 530/812; 530/391.5
(58) Field of Search .................. 435/4, 7.1, 7.92, 435/24, 188, 6, 7.5, 23, 177, 964; 436/168, 175, 165, 86, 89, 18, 120, 161, 166, 171, 167, 174, 173, 178, 518, 538, 523–535, 539, 541, 824, 825; 530/367, 812, 391.5, 391.9, 807, 871

(56) References Cited
U.S. PATENT DOCUMENTS

| | | | |
|---|---|---|---|
| 4,798,795 A | 1/1989 | Sigler | 435/177 |
| 5,240,859 A | 8/1993 | Aebersold | 436/89 |
| 5,438,017 A | * 8/1995 | Allen et al. | 436/89 |
| 5,514,559 A | 5/1996 | Marker-Hahn et al. | 436/7.92 |
| 5,527,711 A | 6/1996 | Tom-Moy et al. | 436/518 |
| 5,534,132 A | 7/1996 | Vreeke et al. | 205/777.5 |
| 5,534,440 A | 7/1996 | Aebersold et al. | 436/89 |
| 5,538,897 A | 7/1996 | Yates, III et al. | 436/89 |
| 5,614,368 A | 3/1997 | Ghazarossian et al. | 435/7.5 |
| 5,650,270 A | 7/1997 | Giese et al. | 435/6 |
| 5,658,725 A | 8/1997 | Schlieper et al. | 435/5 |
| 5,686,310 A | 11/1997 | Haystead et al. | 436/86 |
| 5,738,984 A | 4/1998 | Shoeyov | 435/4 |
| 5,851,781 A | 12/1998 | Adamczyk et al. | 435/7.9 |
| 5,863,740 A | 1/1999 | Kientsch-Engel et al. | 435/7.5 |
| 5,880,270 A | 3/1999 | Berninger et al. | 530/391.1 |
| 5,952,653 A | 9/1999 | Covey et al. | 250/288 |
| 5,958,703 A | 9/1999 | Dower et al. | 435/7.1 |
| 5,965,131 A | 10/1999 | Griffiths et al. | 424/133.1 |
| 5,965,457 A | 10/1999 | Magnani | 436/518 |
| 6,017,693 A | 1/2000 | Yates, III et al. | 435/5 |
| 6,057,096 A | * 5/2000 | Rothschild et al. | 435/6 |

FOREIGN PATENT DOCUMENTS

| | | | |
|---|---|---|---|
| WO | WO 90/04786 | 5/1990 | G01N/33/53 |
| WO | WO98/26095 | 6/1998 | C12Q/1/68 |

OTHER PUBLICATIONS

Duncan et al., Amino acid analysis of Peptides and Proteins on femtomole scale by Gas Chromatography/Mass Spectrometry, Anal. Chem. 70: 890–896 (Mar. 1998).*

Aebersold, R. et al. (1991) "Determination of the site of tyrosine phosphorylation at the low picomole level by automated solid–phase sequence analysis" Anal. Biochem. 199:51–60.

Bruce et al. (Jul. 1999) "High–Mass–Measurement Accuracy and 100% Sequence Coverage of Enzymatically Digested Bovine Serum Albumin from an ESI–FTICR Mass Spectrum," Anal. Chem. 71(14):2595–2599.

Davis et al. (Apr. 1998) "Rapid Protein Identification Using a Microscale Electrospray LC/MS System on an Ion Trap Mass Spectrometer," J. Am. Soc. Mass. Spec. 9:194–201.

Fenyo et al. (Jun. 1998) "Protein identification using mass spectrometric information," Electrophoresis 19:998–1005.

Henzel, et al. (Jun. 1993) "Identifying proteins from two–dimensional gels by molecular mass searching of peptide fragments in protein sequence databases," Proc. Natl. Acad. Sci. USA 90:5011–5015.

(List continued on next page.)

Primary Examiner—Long V. Le
Assistant Examiner—Gailene R. Gabel
(74) Attorney, Agent, or Firm—Greenlee, Winner and Sullivan, P.C.

(57) ABSTRACT

Analytical reagents and mass spectrometry-based methods using these reagents for the rapid, and quantitative analysis of proteins or protein function in mixtures of proteins. The methods employ affinity labeled protein reactive reagents having three portions: an affinity label (A) covalently linked to a protein reactive group (PRG) through a linker group (L). The linker may be differentially isotopically labeled, e.g., by substitution of one or more atoms in the linker with a stable isotope thereof. These reagents allow for the selective isolation of peptide fragments or the products of reaction with a given protein (e.g., products of enzymatic reaction) from complex mixtures. The isolated peptide fragments or reaction products are characteristic of the presence of a protein or the presence of a protein function in those mixtures. Isolated peptides or reaction products are characterized by mass spectrometric (MS) techniques. The reagents also provide for differential isotopic labeling of the isolated peptides or reaction products which facilitates quantitative determination by mass spectrometry of the relative amounts of proteins in different samples. The methods of this invention can be used for qualitative and quantitative analysis of global protein expression profiles in cells and tissues, to screen for and identify proteins whose expression level in cells, tissue or biological fluids is affected by a stimulus or by a change in condition or cell state of the cell, tissue or organism from which the sample originated.

96 Claims, 10 Drawing Sheets

OTHER PUBLICATIONS

Horn, et al. (1998) "A Computer Program for Automated Analysis of High Resolution Mass Spectra," Proceedings of the 46$^{th}$ ASMS Conf. on Mass Spectromety and Allied Topics, Orlando, FL May 31–Jun. 4, 1998, p. 118.

Jonscher, K.R. and Yates, J.R. III (Jan. 1997) "Matrix assisted laser desorption ionization/quadrupole ion trap mass spectrometry of peptides. Application to the localization of phosphorylation sites on the P protein from Sendai virus" J,. Biol. Chem. 272(3):1735–1741.

Lundell, N. and Schreitmuller, T. (Jan. 1999) "Sample Preparation for Peptide Mapping—A Pharmaceutical Quality–Control Perspective," Anal. Biochem. 266:31–47.

McCormack, A.L. et al. (1997) "Direct Analysis and Identification of Proteins in Mixtures by LC/MS/MS and Database Searching at the Low–Femtomole Level" Anal. Chem. 69:767–776.

Neubauer et al., "Mass Spectrometry and EST–database searching allows characterization of the multi–protein spliceosome complex," (Sep. 1998) Nature Genetics 20:46–50.

Patterson et al. (1995) "Mass spectrometric approaches for the identification of gel–separated proteins," Electro. 16:1791–1814.

Qin, J. and Chait, B.T. (1997) "Identification and characterization of posttranslational modifications of proteins by MALDI Ion trap mass spectrometry" Anal. Chem. 69(19):4002–4009.

Papayannopoulos, I.A. (1995) "The interpretation of collision–induced dissociation tandem mass spectra of peptides" Mass Spectrometry Rev. 14:49–73.

Watts, J.D. et al. (1994) "Identification by electrospray ionization mass spectrometry of the sites of tyrosine phosphorylation induced in activated Jurkat T cells on the protein tyrosine kinase ZAP–70" J. Biol. Chem. 269(47):29520–29529.

Winger et al. (1993) "High–Resolution Accurate Mass Measurements of Biomolecules Using a New Electrospray ionization Ion Cyclotron Resonance Mass Spectrometer," J. Am. Soc. Mass Spec. 4:566–577.

Goodlett et al. (1993), "Reduced Elution Speed Detection for Capillary Electrophoresis/Mass Spectrometry" *J. Microcolumn Separations* 5:57–62.

Ogryzko, Vasily V. et al. (Jul. 10, 2998), "Histone–Like TAFs within the PCAF Histone Acetylase Complex" *Cell* 94:35–44.

Qin, Jun et al. (1998), "De Novo Peptide Sequencing in an Ion Trap Mass Spectrometer with $^{18}$O Labeling" *Rapid Communications in Mass Spectrometry* 12:209–216.

Paulsen, H. et al. (1993) "Building units of oligosaccharides: CVII. Synthesis of modified oligosaccharides of N–glycoproteins for substrate specificity studies o N–acetylglucosaminyltransferase II." (Abstract in English) of *Liebigs Annalen der Chemie* 7:721–735.

Gygi, S. P. et al., "Quantitative analysis of complex protein mixtures using isotope–coded affinity tags" (Oct. 1999) *Nature Biotechnology* 17:994–999.

Ashikaga, K. et al. (1988), "Intramolecular End–to–End Reactions of Photoactive Terminal Groups Linked by Poly(oxyethylene) Chains," Bull. Chem. Soc. Jpn. 61:2443–2450.

Bayer, E. and Wilchek, M. (1990), "Biotin–Binding Proteins: Overview and Prospects," Methods Enzymol. 184:49–51.

Brockhausen, I. et al. (1989), "Control of glycoprotein synthesis," J. Biol. Chem. 264:11211–11221.

Chapman, A. et al. (1980), "The primary glycosylation defect in class E Thy–I–negative mutant mouse lymphoma cells is an inability to synthesize dolichol–P–mannose," J. Biol. Chem. 255:4441–4446.

Clauser, K.R. et al. (1995), "Rapid mass spectrometric peptide sequencing and mass matching for characterization of human melanoma proteins isolated by two–dimensional PAGE," Proc. Natl. Acad. Sci. USA 92:5072–5076.

De Leenheer, A.P. and Thienpont, L.M. (1992) "Applications of isotope dilution–mass spectrometry in clinical chemistry, pharmacokinetics, and toxicology," Mass Spectrom. Rev. 11:249–307.

DeRisi, J.L. et al. (1997), "Exploring the metabolic and genetic control of gene expression on a genomic scale," Science 278:680–6.

Dongré, A.R. et al. (1997), "Emerging tandem–mass–spectrometry techniques for the rapid identification of proteins," Trends Biotechnol. 15:418–425.

Ducret, A. et al. (1998), "High throughput protein characterization by automated reverse–phase chromatography/electrospray tandem mass spectrometry," Prot. Sci. 7:706–719.

Eng, J. et al. (1994), "An approach to correlate tandem mass spectral data of peptides with amino acid sequences in a protein database," J. Am. Soc. Mass Spectrom. 5:976–989.

Figeys, D. et al. (1998), "Electrophoresis combined with novel mass spectrometry techniques: Powerful tools for the analysis of proteins and proteomes," Electrophoresis 19:1811–1818.

Figeys, D. and Aebersold, R. (1998), "High sensitivity analysis of proteins and peptides by capillary electrophoresis tandem mass spectrometry: Recent developments in technology and applications," Electrophoresis 19:885–892.

Figeys, D. et al. (1996), "Protein identification by solid phase microextraction–capillary zone electrophoresis–microelectrospray–tandem mass spectrometry," Nature Biotech. 14:1579–1583.

Figeys, D. et al. (1997), "A microfabricated device for rapid protein identification by microelectrospray ion trap mass spectrometry," Anal. Chem. 69:3153–3160.

Freeze, H. H. (1998), "Disorders in protein glycosylation and potential therapy," J. Pediatrics 133:593–600.

Freeze, H. H. (1999), "Human glycosylation disorders and sugar supplement therapy," Biochem. Biophys. Res. Commun. 255:189–193.

Gamper, H.B. (1993), "Facile Preparation of Nuclease Resistant 3' Modified Oligodeoxynucleotides," Nucl. Acids. Res. 21:145–150.

Garrels, J. I. et al. (1997), "Proteome studies of *Saccharomyces cerevisiae*: identification and characterization of abundant proteins. Electrophoresis," 18:1347–1360.

Gerber, S.A. et al. (1999), "Analysis of rates of multiple enzymes in cell lysates by electrospray ionization mass spectrometry," J. Am. Chem. Soc. 121:1102–1103.

Glaser, L. (1966) Phosphomannomutase from yeast. In *Meth. Enzymol.* vol. VIII, Neufeld, E. F.; Ginsburg, V. Eds; Academic Press: New York 1966, pp. 183–185.

Gygi, S.P. et al. (1999), "Correlation between portein and mRNA abundance in yeast," Mol. Cell. Biol. 19:1720–1730.

Gygi, S.P. et al. (1999), "Protein analysis by mass spectrometry and sequence database searching: tools for cancer research in the post–genomic era," Electrophoresis 20:310–319.

Haynes, P. A. et al. (1998), "Identification of gel–separated proteins by liquid chromatography electrospray tandem mass spectrometry: Comparison of methods and their limitations," Electrophoresis 19:939–945.

Hodges, P.E. et al. (1999), "The Yeast Proteome Database (YPD): a model for the organization and presentation of genome–wide functional data," Nucl. Acids Res. 27:69–73.

Kataky, R. et al. (1990), "Comparative Study of Mono– and Di–substituted 14–Crown–4 Derivatives as Lithium Ionophores," J. Chem. Soc. Perkin Trans. 2(2):321–327.

Kaur, K. J. and Alton, G.; Hindsgaul, O. (1991), "Use of N–acetylglucosaminyl–transerases I and II in the preparative synthesis of oligosaccharides," Carbohydr. Res. 210:145–153.

Kaur, K. J. and Hingsgaul, O. (1991) "A simple synthesis of octyl 3,6–di–O–(α–D–mannopyranosyl)–β–D–manopyranoside and its use as an acceptor for the assay of N–acetylglucosaminetransferase I activity," Glycoconjugate J. 8:90–94.

Körner, C. et al. (1998), "Carbohydrate–deficient glycoprotein syndrome type V: deficiency of dolichyl–P–Glc:Man$_9$GlcNAc$_2$–PP–dolichyl glucosyltransferase," Proc. Natl. Acad. Sci. U.S.A. 95:3200–13205.

Link, A. J. et al. (1997), "Identifying the major proteome components of *Haemophilus influenzae* type–strain NCTC 8143," Electrophoresis 18:1314–1334.

Link, J. et al. (1999), "Direct analysis of large protein complexes using mass spectrometry," Nat. Biotech. In press.

Mann, M. and Wilm, M. (1994), "Error–tolerant identification of peptides in sequence databases by peptide sequence tags," Anal. Chem. 66:4390–4399.

McMurry, J. E. and Kocovsky, P. (1984), "A method for the pallidium–catalyzed allylic oxidation of olefins," Tetrahedron Lett. 25, 4187–4190.

Morris, A.A.M. and Turnbull, D.M. (1994), "Metabolic disorders in children," Curr. Opin Neurol. 7:535–541.

Oda, Y. et al. (1999) "Accurate quantitation of protein expression and site–specific phosphorylation," Proc. Natl. Acad. Sci. USA 96:6591–6596.

Okada, S. and O'Brien, J.S. (1968), "Generalized Gangliosides: Beta–Galactosidase Deficiency," Science 160:1002–1004.

Opiteck, G.J. et al. (1997), "Comprehensive on–line LC/LC/MS of proteins," Anal. Chem. 69:1518–1524.

Paulsen, H. and Meinjohanns, E. (1992), "Synthesis of modified oligosaccharides of N–glycoproteins intended for substrate specificity studies of N–acetylglucosaminyltransferases II–V," Tetrahedron Lett. 33:7327–7330.

Pennington, S. R. et al. (1997), "Proteome analysis: from protein characterization to biological function," Trends Cell Bio. 7:168–173.

Qin, J. et al. (1997), "A strategy for rapid, high–confidence protein identification," Anal. Chem. 69:3995–4001.

Romanowska et al. (1994), "Serological and Structural Features of *Hafnia Alvei* Lipopolysaccharides containing D–3–hydroxybutyric Acid," FEMS Immunol. Med. Microbiol. 8(1):83–8.

Romanowska, A. (1994), "Michael Additions for Synthesis of Neoglycoproteins," Methods Enzymol. 242:90–101.

Ronin, C. et al. (1981), "Transfer of glucose in the biosynthesis of thyroid glycoproteins. I. Inhibition of glucose transfer to oligosaccharide lipids by GDP–mannose," Biochim. Biophy. Acta 674, 48–57.

Ronin, C. et al. (1981a), "Synthetic substrates for thyroid oligosaccharide transferase. Effects of peptide chain length and modifications in the –Asn–Xaa–Thr–region," Eur. J. Biochem. 118, 159–164.

Ronne, H. (1995), "Glucose repression in fungi," Trends Genet. 11:12–17.

Roth, F.P. et al. (1998), "Finding DNA regulatory motifs within unaligned noncoding sequences clustered by whole–genome mRNA quantitation," Nat. Biotechnol. 16:939–945.

Rush, J. S. and Wachter, C. J. (1995), "Transmembrane movement of a water–soluble analogue of mannosylphosphoryldolichol is mediated by an endoplasmic reticulum protein," J. Cell. Biol. 130:529–536.

Rush and Wachter (1995), "Methods for determination of cellular levels of guanosine–5'–diphosphate–mannose based on a weak interaction with concavalin A at low pH," Anal. Biochem. 224(2):494–501.

Schacter, H. (1986), "Biosynthetic controls that determine the branching and microheterogeneity of protein–bound oligosaccharides," Biochem. Cell Biol. 64, 163–181.

Sechi, S. and Chait, B.T. (1998), "Modification of cysteine residues by alkylation. A tool in peptide mapping and protein identification," Anal. Chem. 70:5150–5158.

Shalon, D. et al. (1996), "A DNA microarray system for analyzing complex DNA samples using two–color fluorescent probe hybridization," Genome Res. 6:639–645.

Shevchenko, A. et al. (1996), "Linking genome and proteome by mass spectrometry: large–scale identification of yeast proteins from two dimensional gels," Proc. Natl. Acad. Sci. U.S.A. 93:14440–14445.

Shevchenko, A. et al. (1996), "Mass spectrometric sequencing of proteins silver–stained polyacrylamide gels," Anal. Chem. 68:850–858.

Tan, J. et al. (1996), "Mutations of the MGAT2 gene controlling complex glycan synthesis cause carbohydrate deficient glycoprotein syndrome type II, an autosomal recessive disease with defective brain development,"Am. J. Hum. Genet. 59:810–817.

Velculescu, V. E. et al. (1997), "Characteristics of the yeast transcriptome," Cell 88:243–251.

Wilbur et al. (1997), "Biotin Reagents for Antibody Pretargeting. 2. Synthesis and in Vitro Evaluation of Biotin Dimers and Trimers for Cross–Linking of Streptavidin," Bioconjugate Chem. 8(6):819–832.

Wilbur, D.S. et al. (1997), "Biotin Reagents for Antibody Pretargeting. Synthesis, Radioiodination, and in Vitro Evaluation of Water Soluble, Biotinidase Resistant Biotin Derivatives," Bioconjugate Chem. 8:572–584.

Yates, J. R. et al. (1995), "Method to correlate tandem mass spectra of modified peptides to amino acid sequences in the protein database," Anal. Chem. 67:1426–1436.

\* cited by examiner

| # | Rank/Sp | (M+H) | +C*10^4 | Ions | Reference | Peptide |
|---|---------|-------|---------|------|-----------|---------|
| 1. | 1/1 | 1994.3 | 4.4675 | 17/26 | G3P_RABIT | (R)VPTPNVSVVDLTC#R (SEQ ID NO:60) |
| 2. | 2/403 | 1995.1 | 2.7366 | 13/34 | SLTRNGL | (E)LGKPVLTANQVTIWEGLR (SEQ ID No:61) |
| 3. | 3/3 | 1995.0 | 2.6591 | 16/36 | FLP_LACCA | (N)LANPNVYTETLTAATVCTI (SEQ ID NO:62) |
| 4. | 4/209 | 1995.0 | 2.6335 | 14/36 | A42912 | (Y)LALLPSDAEGPHGQFVTDK (SEQ ID NO:63) |
| 5. | 5/381 | 1995.1 | 2.4634 | 13/38 | H69373 | (L)ALLVLVAPAMAAGNGEDLRN (SEQ INO:64) |

FIG. 4B

ADH1 : YSGVC#HTDLHAWHGDWPLP<u>V</u>K

ADH2 : YSGVC#HTDLHAWHGDWPLP<u>T</u>K

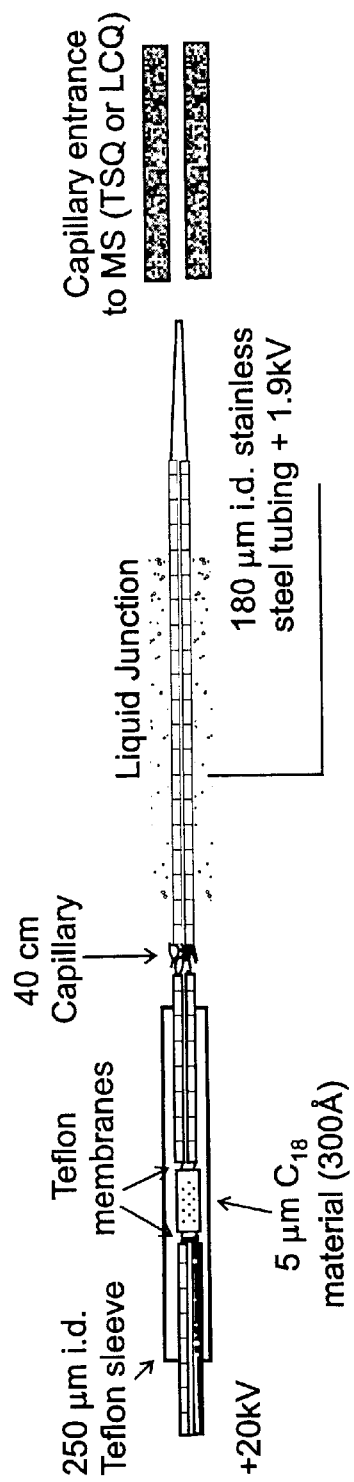
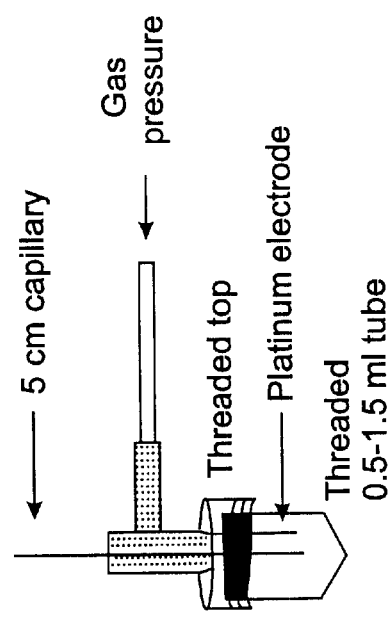
FIG. 8A
FIG. 8B

RAPID QUANTITATIVE ANALYSIS OF PROTEINS OR PROTEIN FUNCTION IN COMPLEX MIXTURES

CROSS-REFERENCE TO RELATED APPLICATIONS

This application takes priority under 35 U.S.C.§119(e) from U.S. provisional applications Ser. No. 60/097,788, filed Aug. 25, 1998 and Ser. No. 60/099,113, filed Sep. 3, 1998, both of which are incorporated in their entirety by reference herein.

This invention was made through funding from the National Science Foundation Science and Technology Center for Molecular Biotechnology (grants 5T32HG and BIR9214821) and the National Institutes of Health (NIH grants RR11823, T32HG00035, HD-02274 and GM60184). The United States government has certain rights in this invention.

BACKGROUND OF THE INVENTION

Genomic technology has advanced to a point at which, in principle, it has become possible to determine complete genomic sequences and to quantitatively measure the mRNA levels for each gene expressed in a cell. For some species the complete genomic sequence has now been determined, and for one strain of the yeast *Saccharomyces cervisiae,* the mRNA levels for each expressed gene have been precisely quantified under different growth conditions (Velculescu et al., 1997). Comparative cDNA array analysis and related technologies have been used to determine induced changes in gene expression at the mRNA level by concurrently monitoring the expression level of a large number of genes (in some cases all the genes) expressed by the investigated cell or tissue (Shalon et al., 1996). Furthermore, biological and computational techniques have been used to correlate specific function with gene sequences. The interpretation of the data obtained by these techniques in the context of the structure, control and mechanism of biological systems has been recognized as a considerable challenge. In particular, it has been extremely difficult to explain the mechanism of biological processes by genomic analysis alone.

Proteins are essential for the control and execution of virtually every biological process. The rate of synthesis and the half-life of proteins and thus their expression level are also controlled post-transcriptionally. Furthermore, the activity of proteins is frequently modulated by post-translational modifications, in particular protein phosphorylation, and dependent on the association of the protein with other molecules including DNA and proteins. Neither the level of expression nor the state of activity of proteins is therefore directly apparent from the gene sequence or even the expression level of the corresponding mRNA transcript. It is therefore essential that a complete description of a biological system include measurements that indicate the identity, quantity and the state of activity of the proteins which constitute the system. The large-scale (ultimately global) analysis of proteins expressed in a cell or tissue has been termed protein analysis (Pennington et al., 1997).

At present no protein analytical technology approaches the throughput and level of automation of genomic technology. The most common implementation of protein analysis is based on the separation of complex protein samples most commonly by two-dimensional gel electrophoresis (2DE) and the subsequent sequential identification of the separated protein species (Ducret et al., 1998; Garrels et al., 1997; Link et al., 1997; Shevchenko et al., 1996; Gygi et al. 1999; Boucherie et al., 1996). This approach has been revolutionized by the development of powerful mass spectrometric techniques and the development of computer algorithms which correlate protein and peptide mass spectral data with sequence databases and thus rapidly and conclusively identify proteins (Eng et al., 1994; Mann and Wilm, 1994; Yates et al., 1995). This technology has reached a level of sensitivity which now permits the identification of essentially any protein which is detectable by conventional protein staining methods including silver staining (Figeys and Aebersold, 1998; Figeys et al., 1996; Figeys et al., 1997; Shevchenko et al., 1996). However, the sequential manner in which samples are processed limits the sample throughput, the most sensitive methods have been difficult to automate and low abundance proteins, such as regulatory proteins, escape detection without prior enrichment, thus effectively limiting the dynamic range of the technique. In the 2DE/(MS)$^n$ method, proteins are quantified by densitometry of stained spots in the 2DE gels.

The development of methods and instrumentation for automated, data-dependent electrospray ionization (ESI) tandem mass spectrometry (MS$^n$) in conjunction with microcapillary liquid chromatography ($\mu$LC) and database searching has significantly increased the sensitivity and speed of the identification of gel-separated proteins. As an alternative to the 2DE/MS$^n$ approach to protein analysis, the direct analysis by tandem mass spectrometry of peptide mixtures generated by the digestion of complex protein mixtures has been proposed (Dongr'e et al., 1997). $\mu$LC-MS/MS has also been used successfully for the large-scale identification of individual proteins directly from mixtures without gel electrophoretic separation (Link et al., 1999; Opitek et al., 1997). While these approaches dramatically accelerate protein identification, the quantities of the analyzed proteins cannot be easily determined, and these methods have not been shown to substantially alleviate the dynamic range problem also encountered by the 2DE/MS/MS approach. Therefore, low abundance proteins in complex samples are also difficult to analyze by the uLC/MS/MS method without their prior enrichment.

It is therefore apparent that current technologies, while suitable to identify the components of protein mixtures, are neither capable of measuring the quantity nor the state of activity of the protein in a mixture. Even evolutionary improvements of the current approaches are unlikely to advance their performance sufficiently to make routine quantitative and functional proteome analysis a reality.

This invention provides methods and reagents that can be employed in proteome analysis which overcome the limitations inherent in traditional techniques. The basic approach described can be employed for the quantitative analysis of protein expression in complex samples (such as cells, tissues, and fractions thereof), the detection and quantitation of specific proteins in complex samples, and the quantitative measurement of specific enzymatic activities in complex samples.

In this regard, a multitude of analytical techniques are presently available for clinical and diagnostic assays which detect the presence, absence, deficiency or excess of a protein or protein function associable with a normal or disease state. While these techniques are quite sensitive, they do not necessarily provide chemical speciation of products and may, as a result, be difficult to use for assaying several proteins or enzymes simultaneously in a single sample. Current methods may not distinguish among aberrant expression of different enzymes or their malfunctions which lead to a common set of clinical symptoms. The methods and reagents herein can be employed in clinical and diagnostic assays for simultaneous (multiplex) monitoring of multiple proteins and protein reactions.

SUMMARY OF THE INVENTION

This invention provides analytical reagents and mass spectrometry-based methods using these reagents for the rapid, and quantitative analysis of proteins or protein function in mixtures of proteins. The analytical method can be used for qualitative and particularly for quantitative analysis of global protein expression profiles in cells and tissues, i.e. the quantitative analysis of proteomes. The method can also be employed to screen for and identify proteins whose expression level in cells, tissue or biological fluids is affected by a stimulus (e.g., administration of a drug or contact with a potentially toxic material), by a change in environment (e.g., nutrient level, temperature, passage of time) or by a change in condition or cell state (e.g., disease state, malignancy, site-directed mutation, gene knockouts) of the cell, tissue or organism from which the sample originated. The proteins identified in such a screen can function as markers for the changed state. For example, comparisons of protein expression profiles of normal and malignant cells can result in the identification of proteins whose presence or absence is characteristic and diagnostic of the malignancy.

In an exemplary embodiment, the methods herein can be employed to screen for changes in the expression or state of enzymatic activity of specific proteins. These changes may be induced by a variety of chemicals, including pharmaceutical agonists or antagonists, or potentially harmful or toxic materials. The knowledge of such changes may be useful for diagnosing enzyme-based diseases and for investigating complex regulatory networks in cells.

The methods herein can also be used to implement a variety of clinical and diagnostic analyses to detect the presence, absence, deficiency or excess of a given protein or protein function in a biological fluid (e.g., blood), or in cells or tissue. The method is particularly useful in the analysis of complex mixtures of proteins, i.e., those containing 5 or more distinct proteins or protein functions.

The inventive method employs affinity-labeled protein reactive reagents that allow for the selective isolation of peptide fragments or the products of reaction with a given protein (e.g., products of enzymatic reaction) from complex mixtures. The isolated peptide fragments or reaction products are characteristic of the presence of a protein or the presence of a protein function, e.g., an enzymatic activity, respectively, in those mixtures. Isolated peptides or reaction products are characterized by mass spectrometric (MS) techniques. In particular, the sequence of isolated peptides can be determined using tandem MS (MS") techniques, and by application of sequence database searching techniques, the protein from which the sequenced peptide originated can be identified. The reagents also provide for differential isotopic labeling of the isolated peptides or reaction products which facilitates quantitative determination by mass spectrometry of the relative amounts of proteins in different samples. Also, the use of differentially isotopically-labeled reagents as internal standards facilitates quantitative determination of the absolute amounts of one or more proteins or reaction products present in the sample.

In general, the affinity labeled protein reactive reagents of this invention have three portions: an affinity label (A) covalently linked to a protein reactive group (PRG) through a linker group (L):

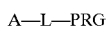

The linker may be differentially isotopically labeled, e.g., by substitution of one or more atoms in the linker with a stable isotope thereof. For example, hydrogens can be substituted with deuteriums or $C^{12}$ with $C^{13}$.

The affinity label A functions as a molecular handle that selectively binds covalently or non-covalently, to a capture reagent (CR). Binding to CR facilitates isolation of peptides, substrates or reaction products tagged or labeled with A. In specific embodiments, A is a strepavidin or avidin. After affinity isolation of affinity tagged materials, some of which may be isotopically labeled, the interaction between A and the capture reagent is disrupted or broken to allow MS analysis of the isolated materials. The affinity label may be displaced from the capture reagent by addition of displacing ligand, which may be free A or a derivative of A, or by changing solvent (e.g., solvent type or pH) or temperature conditions or the linker may be cleaved chemically, enzymatically, thermally or photochemically to release the isolated materials for MS analysis.

Two types of PRG groups are specifically provided herein: (a) those groups that selectively react with a protein functional group to form a covalent or non-covalent bond tagging the protein at specific sites, and (b) those that are transformed by action of the protein, e.g., that are substrates for an enzyme. In specific embodiments, PRG is a group having specific reactivity for certain protein groups, such as specificity for sulfhydryl groups, and is useful in general for selectively tagging proteins in complex mixtures. A sulfhydryl specific reagent tags proteins containing cysteine. In other specific embodiments, PRG is an enzyme substrate that is selectively cleaved (leaving A—L) or modified (giving A—L—PRG') by the action of an enzyme of interest.

Exemplary reagents have the general formula:

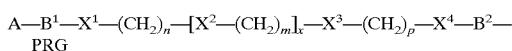

where:

A is the affinity label;

PRG is the protein reactive group;

$X^1$, $X^2$, $X^3$ and $X^4$, independently of one another, and $X^2$ independently of other $X^2$ in the linker group, can be selected from O, S, NH, NR, NRR'+, CO, COO, COS, S—S, SO, $SO_2$, CO—NR', CS—NR', Si—O, aryl or diaryl groups or $X^1$–$X^4$ may be absent, but preferably at least one of $X^1$–$X^4$ is present;

$B^1$ and $B^2$, independently of one another, are optional moieties that can faciliate bonding of the A or PRG group to the linker or prevent undesired cleavage of those groups from the linker and can be selected, for example, from COO, CO, CO—NR', CS—NR' and may contain one or more $CH_2$ groups alone or in combination with other groups, e.g. $(CH_2)_q$—CONR', $(CH_2)_q$—CS—NR', or $(CH_2)_{q'}$;

n, m, p and q are whole numbers that can have values from 0 to about 100, preferably one of n, m, p or q is not 0 and x is also a whole number that can range from 0 to about 100 where the sum of n+xm+p+q is preferably less than about 100 and more preferably less than about 20;

R is an alkyl, alkenyl, alkynyl, alkoxy or aryl group; and
R' is a hydrogen, an alkyl, alkenyl, alkynyl, alkoxy or aryl group.

One or more of the $CH_2$ groups of the linker can be optionally substituted with small (C1–C6) alkyl, alkenyl, or alkoxy groups, an aryl group or can be substituted with functional groups that promote ionization, such as acidic or basic groups or groups carrying permanent positive or negative charge. One or more single bonds connecting $CH_2$ groups in the linker can be replaced with a double or a triple bond. Preferred R and R' alkyl, alkenyl, alkynyl or alkoxy groups are small having 1 to about 6 carbon atoms.

One or more of the atoms in the linker can be substituted with a stable isotope to generate one or more substantially chemically identical, but isotopically distinguishable reagents. For example, one or more hydrogens in the linker can be substituted with deuterium to generate isotopically heavy reagents.

In an exemplary embodiment the linker contains groups that can be cleaved to remove the affinity tag. If a cleavable linker group is employed, it is typically cleaved after affinity tagged peptides, substrates or reaction products have been isolated using the affinity label together with the CR. In this case, any isotopic labeling in the linker preferably remains bound to the protein, peptide, substrate or reaction product.

Linker groups include among others: ethers, polyethers, ether diamines, polyether diamines, diamines, amides, polyamides, polythioethers, disulfides, silyl ethers, alkyl or alkenyl chains (straight chain or branched and portions of which may be cyclic), aryl, diaryl or alkyl-aryl groups. Aryl groups in linkers can contain one or more heteroatoms (e.g., N, O or S atoms).

In one aspect, the invention provides a mass spectrometric method for identification and quantitation of one or more proteins in a complex mixture which employs affinity labeled reagents in which the PRG is a group that selectively reacts with certain groups that are typically found in peptides (e.g., sulfhydryl, amino, carboxy, homoserine lactone groups). One or more affinity labeled reagents with different PRG groups are introduced into a mixture containing proteins and the reagents react with certain proteins to tag them with the affinity label. It may be necessary to pretreat the protein mixture to reduce disulfide bonds or otherwise facilitate affinity labeling. After reaction with the affinity labeled reagents, proteins in the complex mixture are cleaved, e.g., enzymatically, into a number of peptides. This digestion step may not be necessary, if the proteins are relatively small. Peptides that remain tagged with the affinity label are isolated by an affinity isolation method, e.g., affinity chromatography, via their selective binding to the CR. Isolated peptides are released from the CR by displacement of A or cleavage of the linker, and released materials are analyzed by liquid chromatography/mass spectrometry (LC/MS). The sequence of one or more tagged peptides is then determined by $MS^n$ techniques. At least one peptide sequence derived from a protein will be characteristic of that protein and be indicative of its presence in the mixture. Thus, the sequences of the peptides typically provide sufficient information to identify one or more proteins present in a mixture.

Quantitative relative amounts of proteins in one or more different samples containing protein mixtures (e.g., biological fluids, cell or tissue lysates, etc.) can be determined using chemically identical, affinity tagged and differentially isotopically labeled reagents to affinity tag and differentially isotopically label proteins in the different samples. In this method, each sample to be compared is treated with a different isotopically labeled reagent to tag certain proteins therein with the affinity label. The treated samples are then combined, preferably in equal amounts, and the proteins in the combined sample are enzymatically digested, if necessary, to generate peptides. Some of the peptides are affinity tagged and in addition tagged peptides originating from different samples are differentially isotopically labeled. As described above, affinity labeled peptides are isolated, released from the capture reagent and analyzed by (LC/MS). Peptides characteristic of their protein origin are sequenced using $MS^n$ techniques allowing identification of proteins in the samples. The relative amounts of a given protein in each sample is determined by comparing relative abundance of the ions generated from any differentially labeled peptides originating from that protein. The method can be used to assess relative amounts of known proteins in different samples. Further, since the method does not require any prior knowledge of the type of proteins that may be present in the samples, it can be used to identify proteins which are present at different levels in the samples examined. More specifically, the method can be applied to screen for and identify proteins which exhibit differential expression in cells, tissue or biological fluids. It is also possible to determine the absolute amounts of specific proteins in a complex mixture. In this case, a known amount of internal standard, one for each specific protein in the mixture to be quantified, is added to the sample to be analyzed. The internal standard is an affinity tagged peptide that is identical in chemical structure to the affinity tagged peptide to be quantified except that the internal standard is differentially isotopically labeled, either in the peptide or in the affinity tag portion, to distinguish it from the affinity tagged peptide to be quantified. The internal standard can be provided in the sample to be analyzed in other ways. For example, a specific protein or set of proteins can be chemically tagged with an isotopically-labeled affinity tagging reagent. A known amount of this material can be added to the sample to be analyzed. Alternatively, a specific protein or set of proteins may be labeled with heavy atom isotopes and then derivatized with an affinity tagging reagent.

Also, it is possible to quantify the levels of specific proteins in multiple samples in a single analysis (multiplexing). In this case, affinity tagging reagents used to derivatize proteins present in different affinity tagged peptides from different samples can be selectively quantified by mass spectrometry.

In this aspect of the invention, the method provides for quantitative measurement of specific proteins in biological fluids, cells or tissues and can be applied to determine global protein expression profiles in different cells and tissues. The same general strategy can be broadened to achieve the proteome-wide, qualitative and quantitative analysis of the state of modification of proteins, by employing affinity reagents with differing specificity for reaction with proteins. The method and reagents of this invention can be used to identify low abundance proteins in complex mixtures and can be used to selectively analyze specific groups or classes of proteins such as membrane or cell surface proteins, or proteins contained within organelles, sub-cellular fractions, or biochemical fractions such as immunoprecipitates. Further, these methods can be applied to analyze differences in expressed proteins in different cell states. For example, the methods and reagents herein can be employed in diagnostic assays for the detection of the presence or the absence of one or more proteins indicative of a disease state, such as cancer.

In a second aspect, the invention provides a MS method for detection of the presence or absence of a protein function, e.g., an enzyme activity, in a sample. The method can also be employed to detect a deficiency or excess (over normal levels) of protein function in a sample. Samples that can be analyzed include various biological fluids and materials, including tissue and cells. In this case, the PRG of the affinity labeled reagent is a substrate for the enzyme of interest. Affinity labeled substrates are provided for each enzyme of interest and are introduced into a sample where they react to generate affinity labeled products, if the enzyme of interest is present in the sample. Products or unreacted substrate that are tagged with the affinity label are isolated by an affinity isolation method, e.g., affinity chromatography, via their selective binding to the CR. The isolated tagged substrates and products are analyzed by mass spectrometry. Affinity labeled products include those in which the substrate is entirely cleaved from the linker or in which the substrate is modified by reaction with a protein of interest. Detection of the affinity-labeled product indicates the protein function is present in the sample. Detection of little or no affinity labeled product indicates deficiency or absence, respectively, of the protein function in the sample.

The amount of selected protein, e.g., measured in terms of enzyme activity, present in a sample can be measured by introducing a known amount of an internal standard which is an isotopically labeled analog of the expected product of the enzymatic reaction of the reagent substrate. The internal standard is substantially chemically identical to the expected enzymatic reaction product, but is isotopically distinguishable therefrom. The level of protein function (e.g., enzymatic activity) in a given sample can be compared with activity levels in other samples or controls (either negative or positive controls). The procedure therefore can detect the presence, absence, deficiency or excess of a protein function in a sample. The method is capable of quantifying the velocity of an enzymatic reaction since it enables the amount of product formed over a known time period to be measured. This method can be multiplexed, by simultaneous use of a plurality of affinity labeled substrates selective for different protein functions and if quantitation is desired by inclusion of the corresponding internal standards for expected products, to analyze for a plurality of protein functions in a single sample.

BRIEF DESCRIPTION OF THE FIGURES

FIG. 3 shows a mass spectrum for a single differentially labeled peptide pair.

FIG. 4B shows the result of database searching the CID spectrum of FIG. 4A.

FIG. 8 is a schematic representation of the SPE$^6$-CE-MS/MS system.

DETAILED DESCRIPTION OF THE INVENTION

Figure 1B:
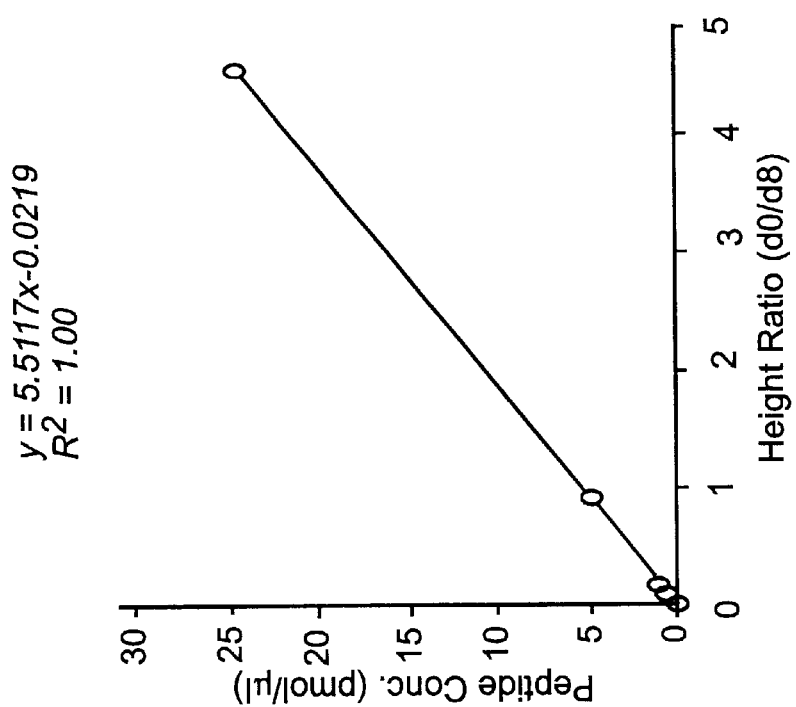
FIG. 1 is a standard curve generated with a cysteine-biotinylated peptide and quantitated by stable isotope dilution. A) Zoom-scan from an ion-trap mass spectrometer showing a 4 amu isotope distribution for the $[M+2H]^{2+}$ ions of the peptide modified with the isotopically light (1457.9 u) and heavy (1461.8) biotinylating reagents. The ratio (d0/d8) was 4.54. B) Curve generated from the analysis of isotope ratios from zoom-scans of 5 different concentrations of d0-labeled peptide measured in the presence of a known amount of peptide labeled with the isotopically heavy reagent.

The methods of this invention employ affinity tagged protein reactive reagents in which the affinity tag is covalently attached to a protein reactive group by a linker. The linker can be isotopically labeled to generate pairs or sets of reagents that are substantially chemically identical, but which are distinguishable by mass. For example a pair of reagents, one of which is isotopically heavy and the other of which is isotopically light can be employed for the comparison of two samples one of which may be a reference sample containing one or more known proteins in known amounts. For example, any one or more of the hydrogen, nitrogen, oxygen or sulfur atoms in the linker may be replaced with their isotopically stable isotopes: $^2$H, $^{13}$C, $^{15}$N, $^{17}$O, $^{18}$O or $^{34}$S.

Suitable affinity tags bind selectively either covalently or non-covalently and with high affinity to a capture reagent (CR). The CR-A interaction or bond should remain intact after extensive and multiple washings with a variety of solutions to remove non-specifically bound components. The affinity tag binds minimally or preferably not at all to components in the assay system, except CR, and does not significantly bind to surfaces of reaction vessels. Any non-specific interaction of the affinity tag with other components or surfaces should be disrupted by multiple washes that leave CR-A intact. Further, it must be possible to disrupt the interaction of A and CR to release peptides, substrates or reaction products, for example, by addition of a displacing ligand or by changing the temperature or solvent conditions. Preferably, neither CR nor A react chemically with other components in the assay system and both groups should be chemically stable over the time period of an assay or experiment. The affinity tag preferably does not undergo peptide-like fragmentation during (MS)$^n$ analysis. The affinity label is preferably soluble in the sample liquid to be analyzed and the CR should remain soluble in the sample liquid even though attached to an insoluble resin such as Agarose. In the case of CR term soluble means that CR is sufficiently hydrated or otherwise solvated such that it functions properly for binding to A. CR or CR-containing conjugates should not be present in the sample to be analyzed, except when added to capture A.

any 1,2-diol, such as 1,2-dihydroxyethane (HO—CH$_2$—CH$_2$—OH), and other 1,2-dihydroxyalkanes including those of cyclic alkanes, e.g., 1,2-dihydroxycyclohexane which bind to an alkyl or aryl boronic acid or boronic acid esters, such as phenyl-B(OH)$_2$ or hexyl-B(OEthyl)$_2$ which may be attached via the alkyl or aryl group to a solid support material, such as Agarose;

maltose which binds to maltose binding protein (as well as any other sugar/sugar binding protein pair or more generally to any ligand/ligand binding protein pairs that has properties discussed above);

a hapten, such as dinitrophenyl group, for any antibody where the hapten binds to an anti-hapten antibody that recognizes the hapten, for example the dinitrophenyl group will bind to an anti-dinitrophenyl-IgG;

a ligand which binds to a transition metal, for example, an oligomeric histidine will bind to Ni(II), the transition metal CR may be used in the form of a resin bound chelated transition metal, such as nitrilotriacetic acid-chelated Ni(II) or iminodiacetic acid-chelated Ni(II);

glutathione which binds to glutathione-S-transferase.

In general, any A-CR pair commonly used for affinity enrichment which meets the suitability criteria discussed above. Biotin and biotin-based affinity tags are preferred. Of particular interest are structurally modified biotins, such as d-iminobiotin, which will elute from avidin or strepavidin columns under solvent conditions compatible with ESI-MS analysis, such as dilute acids containing 10–20% organic solvent. It is expected that d-iminobiotin tagged compounds will elute in solvents below pH 4. d-Iminobiotin tagged protein reactive reagents can be synthesized by methods described herein for the corresponding biotin tagged reagents.

A displacement ligand, DL, is optionally used to displace A from CR. Suitable DLs are not typically present in samples unless added. DL should be chemically and enzymatically stable in the sample to be analyzed and should not react with or bind to components (other than CR) in samples or bind non-specifically to reaction vessel walls. DL preferably does not undergo peptide-like fragmentation during MS analysis, and its presence in sample should not significantly suppress the ionization of tagged peptide, substrate or reaction product conjugates.

DL itself preferably is minimally ionized during mass spectrometric analysis and the formation of ions composed of DL clusters is preferably minimal. The selection of DL, depends upon the A and CR groups that are employed. In general, DL is selected to displace A from CR in a reasonable time scale, at most within a week of its addition, but more preferably within a few minutes or up to an hour. The affinity of DL for CR should be comparable or stronger than the affinity of the tagged compounds containing A for CR. Furthermore, DL should be soluble in the solvent used during the elution of tagged compounds containing A from CR. DL preferably is free A or a derivative or structural modification of A. Examples of DL include, d-biotin or d-biotin derivatives, particularly those containing groups that suppress cluster formation or suppress ionization in MS.

The linker group (L) should be soluble in the sample liquid to be analyzed and it should be stable with respect to chemical reaction, e.g., substantially chemically inert, with components of the sample as well as A and CR groups. The linker when bound to A should not interfere with the specific interaction of A with CR or interfere with the displacement of A from CR by a displacing ligand or by a change in temperature or solvent. The linker should bind minimally or preferably not at all to other components in the system, to reaction vessel surfaces or CR. Any non-specific interactions of the linker should be broken after multiple washes which leave the A-CR complex intact. Linkers preferably do not undergo peptide-like fragmentation during $(MS)^n$ analysis. At least some of the atoms in the linker groups should be readily replaceable with stable heavy-atom isotopes. The linker preferably contains groups or moieties that facilitate ionization of the affinity tagged reagents, peptides, substrates or reaction products.

To promote ionization, the linker may contain acidic or basic groups, e.g., COOH, $SO_3H$, primary, secondary or tertiary amino groups, nitrogen-heterocycles, ethers, or combinations of these groups. The linker may also contain groups having a permanent charge, e.g., phosphonium groups, quaternary ammonium groups, sulfonium groups, chelated metal ions, tetralky or tetraryl borate or stable carbanions.

The covalent bond of the linker to A or PRG should typically not be unintentionally cleaved by chemical or enzymatic reactions during the assay. In some cases it may be desirable to cleave the linker from the affinity tag A or from the PRG, for example to facilitate release from an affinity column. Thus, the linker can be cleavable, for example, by chemical, thermal or photochemical reaction. Photocleavable groups in the linker may include the 1-(2-nitrophenyl)-ethyl group. Thermally labile linkers may, for example, be a double-stranded duplex formed from two complementary strands of nucleic acid, a strand of a nucleic acid with a complementary strand of a peptide nucelic acid, or two complementary peptide nucelic acid strands which will dissociate upon heating. Cleavable linkers also include those having disulfide bonds, acid or base labile groups, including among others, diarylmethyl or trimethylarylmethyl groups, silyl ethers, carbamates, oxyesters, thiesters, thionoesters, and α-fluorinated amides and esters. Enzymatically cleavable linkers can contain, for example, protease-sensitive amides or esters, β-lactamase-sensitive β-lactam analogs and linkers that are nuclease-cleavable, or glycosidase-cleavable.

The protein reactive group (PRG) can be a group that selectively reacts with certain protein functional groups or is a substrate of an enzyme of interest. Any selectively reactive protein reactive group should react with a functional group of interest that is present in at least a portion of the proteins in a sample. Reaction of PRG with functional groups on the protein should occur under conditions that do not lead to substantial degradation of the compounds in the sample to be analyzed. Examples of selectively reactive PRGs suitable for use in the affinity tagged reagents of this invention, include those which react with sulfhydryl groups to tag proteins containing cysteine, those that react with amino groups, carboxylate groups, ester groups, phosphate reactive groups, and aldehyde and/or ketone reactive groups or, after fragmentation with CNBr, with homoserine lactone.

Thiol reactive groups include epoxides, α-haloacyl group, nitriles, sulfonated alkyl or aryl thiols and maleimides. Amino reactive groups tag amino groups in proteins and include sulfonyl halides, isocyanates, isothiocyanantes, active esters, including tetrafluorophenyl esters, and N-hydroxysuccinimidyl esters, acid halides, and acid anyhydrides. In addition, amino reactive groups include aldehydes or ketones in the presence or absence of $NaBH_4$ or $NaCNBH_3$.

Carboxylic acid reactive groups include amines or alcohols in the presence of a coupling agent such as dicyclohexylcarbodiimide, or 2,3,5,6-tetrafluorophenyl trifluoroacetate and in the presence or absence of a coupling catalyst such as 4-dimethylaminopyridine; and transition metal-diamine complexes including Cu(II)phenanthroline.

Ester reactive groups include amines which, for example, react with homoserine lactone.

Phosphate reactive groups include chelated metal where the metal is, for example Fe(III) or Ga(III), chelated to, for example, nitrilotriacetiac acid or iminodiacetic acid.

Aldehyde or ketone reactive groups include amine plus $NaBH_4$ or $NaCNBH_3$, or these reagents after first treating a carbohydrate with periodate to generate an aldehyde or ketone.

PRG groups can also be substrates for a selected enzyme of interest. The enzyme of interest may, for example, be one that is associated with a disease state or birth defect or one that is routinely assayed for medical purposes. Enzyme substrates of interest for use with the methods of this invention include, acid phosphatase, alkaline phosphatase, alanine aminotransferase, amylase, angiotensin converting enzyme, aspartate aminotransferase, creatine kinase, gamma-glutamyltransferase, lipase, lactate dehydrogenase, and glucose-6-phosphate dehydrogenase which are currently routinely assayed by other methods.

The requirements discussed above for A, L, PRG, extend to the corresponding to the segments of A—L—PRG and the reaction products generated with this reagent.

Internal standards, which are appropriately isotopically labelled, may be employed in the methods of this invention to measure absolute quantitative amounts of proteins in samples. Internal standards are of particular use in assays intended to quantitate affinity tagged products of enzymatic reactions. In this application, the internal standard is chemically identical to the tagged enzymatic product generated by the action of the enzyme on the affinity tagged enzyme substrate, but carries isotope labels which may include $^2$H, $^{13}$C, $^{15}$N, $^{17}$O, $^{18}$O, or $^{34}$S, that allow it to be independently detected by MS techniques. Internal standards for use in method herein to quantitative one or several proteins in a sample are prepared by reaction of affinity labeled protein reactive reagents with a known protein to generate the affinity tagged peptides generated from digestion of the tagged protein. Affinity tagged peptides internal standards are substantially chemically identical to the corresponding affinity tagged peptides generated from digestion of affinity tagged protein, except that they are differentially isotopically labeled to allow their independent detection by MS techniques.

The method of this invention can also be applied to determine the relative quantities of one or more proteins in two or more protein samples, the proteins in each sample are reacted with affinity tagging reagents which are substantially chemically identical but differentially isotopically labeled. The samples are combined and processed as one. The relative quantity of each taggged peptide which reflects the relative quantity of the protein from which the peptide originates is determined by the measurement of the respective isotope peaks by mass spectrometry.

The methods of this invention can be applied to the analysis or comparison of multiple different samples. Samples that can be analyzed by methods of this invention include cell homogenates; cell fractions; biological fluids including urine, blood, and cerebrospinal fluid; tissue homogenates; tears; feces; saliva; lavage fluids such as lung or peritoneal lavages; mixtures of biological molecules including proteins, lipids, carbohydrates and nucleic acids generated by partial or complete fractionation of cell or tissue homogenates.

The methods of this invention employ MS and $(MS)^n$ methods. While a variety of MS and $(MS)^n$ are available and may be used in these methods, Matrix Assisted Laser Desorption Ionization MS (MALDI/MS) and Electrospray Ionization MS (ESI/MS) methods are preferred.

Quantitative Proteome Analysis

This method is schematically illustrated in Scheme 1 using a biotin labeled sulfhydryl-reactive reagent for quantitative protein profile measurements in a sample protein mixture and a reference protein mixture. The method comprises the following steps:

Reduction. Disulfide bonds of proteins in the sample and reference mixtures are reduced to free SH groups. The preferred reducing agent is tri-n-butylphosphine which is used under standard conditions. Alternative reducing agents include mercaptoethylamine and dithiothreitol. If required, this reaction can be performed in the presence of solubilizing agents including high concentrations of urea and detergents to maintain protein solubility. The reference and sample protein mixtures to be compared are processed separately, applying identical reaction conditions;

Derivatization of SH groups with an affinity tag. Free SH groups are derivatized with the biotinylating reagent biotinyl-iodoacetylamidyl-4,7,10 trioxatridecanediamine the synthesis of which is described below. The reagent is prepared in different isotopically labeled forms by substitution of linker atoms with stable isotopes and each sample is derivatized with a different isotopically labeled form of the reagent. Derivatization of SH groups is preferably performed under slightly basic conditions (pH 8.5) for 90 min at RT. For the quantitative, comparative analysis of two samples, one sample each (termed reference sample and sample) are derivatized as illustrated in Scheme 1 with the isotopically light and the isotopically heavy form of the reagent, respectively. For the comparative analysis of several samples one sample is designated a reference to which the other samples are related to. Typically, the reference sample is labeled with the isotopically heavy reagent and the experimental samples are labeled with the isotopically light form of the reagent, although this choice of reagents is arbitrary. These reactions are also compatible with the presence of high concentrations of solubilizing agents;

Combination of labeled samples. After completion of the affinity tagging reaction defined aliquots of the samples labeled with the isotopically different reagents (e.g., heavy and light reagents) are combined and all the subsequent steps are performed on the pooled samples. Combination of the differentially labeled samples at this early stage of the procedure eliminates variability due to subsequent reactions and manipulations. Preferably equal amounts of each sample are combined;

Removal of excess affinity tagged reagent. Excess reagent is adsorbed, for example, by adding an excess of SH-containing beads to the reaction mixture after protein SH groups are completely derivatized. Beads are added to the solution to achieve about a 5-fold molar excess of SH groups over the reagent added and incubated for 30 min at RT. After the reaction the beads are be removed by centrifugation;

Protein digestion. The proteins in the sample mixture are digested, typically with trypsin. Alternative proteases are also compatible with the procedure as in fact are chemical fragmentation procedures. In cases in which the preceding steps were performed in the presence of high concentrations of denaturing solubilizing agents the sample mixture are diluted until the denaturant concentration is compatible with the activity of the proteases used. This step may be omitting in the analysis of small proteins;

Affinity isolation of the affinity tagged peptides by interaction with a capture reagent. The biotinylated peptides are isolated on avidin-agarose. After digestion the pH of the peptide samples is lowered to 6.5 and the biotinylated peptides are immobilized on beads coated with monomeric avidin (Pierce). The beads are extensively washed. The last washing solvent includes 10% methanol to remove residual SDS. Biotinylated peptides are eluted from avidin-agarose, for example, with 0.3% formic acid at pH 2;

Analysis of the isolated, derivatized peptides by $\mu$LC-$MS^n$ or CE-$MS^n$ with data dependent fragmentation. Methods and instrument control protocols well-known in the art and described, for example, in Ducret et al., 1998; Figeys and Aebersold, 1998; Figeys et al., 1996; or Haynes et al., 1998 are used.

In this last step, both the quantity and sequence identity of the proteins from which the tagged peptides originated can be determined by automated multistage MS. This is achieved by the operation of the mass spectrometer in a dual mode in which it alternates in successive scans between measuring the relative quantities of peptides eluting from the capillary column and recording the sequence information of selected peptides. Peptides are quantified by measuring in the MS mode the relative signal intensities for pairs of peptide ions of identical sequence that are tagged with the isotopically light or heavy forms of the reagent, respectively, and which therefore differ in mass by the mass differential encoded within the affinity tagged reagent. Peptide sequence information is automatically generated by selecting peptide ions of a particular mass-to-charge (m/z) ratio for collision-induced dissociation (CID) in the mass spectrometer operating in the $MS^n$ mode. (Link, A. J. et al. (1997), Gygi, S. P. et al. (1999), and Gygi, S. P. et al. (1999)). The resulting CID spectra are then automatically correlated with sequence databases to identify the protein from which the sequenced peptide originated. Combination of the results generated by MS and $MS^n$ analyses of affinity tagged and differentially labeled peptide samples therefore determines the relative quantities as well as the sequence identities of the components of protein mixtures in a single, automated operation.

Figure 1A:
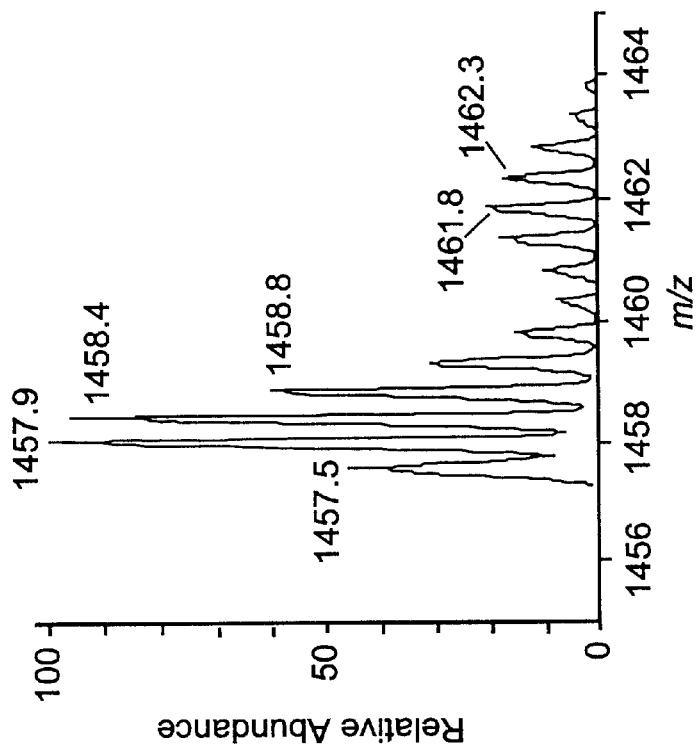
Figure 2:
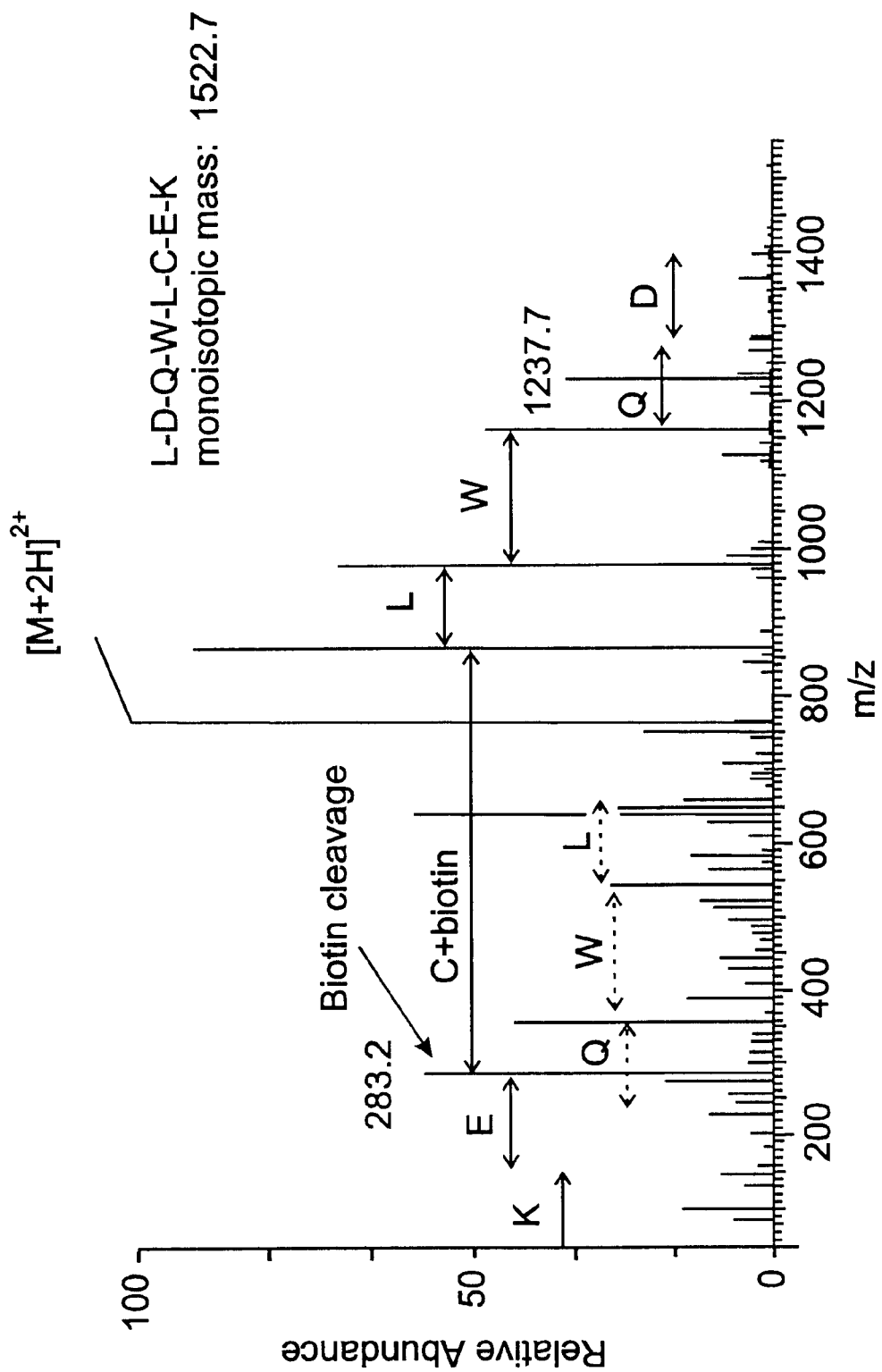
FIG. 2 is a tandem mass spectrum of a cysteine-modified peptide from α-lactalbumin.

Results of applying this method using the biotinylated sulfhydryl reagent and to the quantitative analysis of synthetic peptide samples, to the relative quantitation of the peptides in a protein digest and the tandem mass spectral analysis of a derivatized peptide are shown in FIG. 1, Table 1, and FIG. 2, respectively.

This method can also be practiced using other affinity tags and other protein reactive groups, including amino reactive groups, carboxyl reactive groups, or groups that react with homoserine lactones.

The approach employed herein for quanitative proteome analysis is based on two principles. First, a short sequence of contiguous amino acids from a protein (5–25 residues) contains sufficient information to uniquely identify that protein. Protein identification by $MS^n$ is accomplished by correlating the sequence information contained in the CID mass spectrum with sequence databases, using sophisticated computer searching algorithms (Eng, J. et al. (1994); Mann, M. et al. (1994); Qin, J. et al. (1997); Clauser, K. R. et al. (1995)). Second, pairs of identical peptides tagged with the light and heavy affinity tagged reagents, respectively, (or in analysis of more than two samples, sets of identical tagged peptides in which each set member is differentially isotopically labeled) are chemically identical and therefore serve as mutual internal standards for accurate quantitation. The MS measurement readily differentiates between peptides originating from different samples, representing for example different cell states, because of the difference between isotopically distinct reagents attached to the peptides. The ratios between the intensities of the differing weight components of these pairs or sets of peaks provide an accurate measure of the relative abundance of the peptides (and hence the proteins) in the original cell pools because the MS intensity response to a given peptide is independent of the isotopic composition of the reagents (De Leenheer, A. P. et al (1992). The use of isotopically labeled internal standards is standard practice in quantitative mass spectrometry and has been exploited to great advantage in, for example, the precise quantitation of drugs and metabolites in bodily fluids (De Leenheer, A. P. et al. (1992).

In another illustration of the method, two mixtures consisting of the same six proteins at known, but different, concentrations were prepared and analyzed. The protein mixtures were labeled, combined and treated as schematically illustrated in Scheme 1. The isolated, tagged peptides were quantified and sequenced in a single combined $\mu$LC-MS and $\mu$LC-$MS^n$ experiment on an ESI ion trap mass spectrometer. All six proteins were unambiguously identified and accurately quantified (Table 2). Multiple tagged peptides were encountered for each protein. The differences between the observed and expected quantities for the six proteins ranged between 2 and 12%.

Figure 3A:
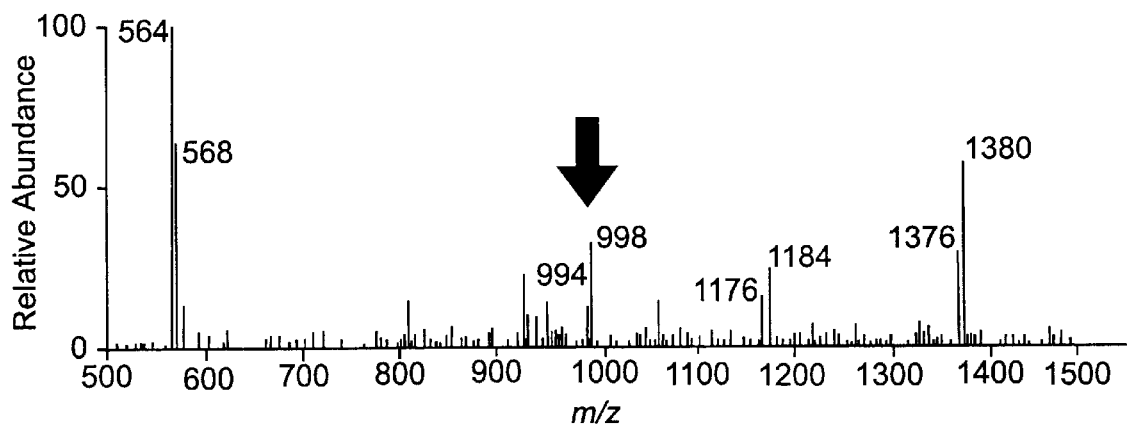
FIG. 3A shows four pairs of peptide ions characterized by the mass differential encoded in the affinity tagged reagent.
Figure 3B:
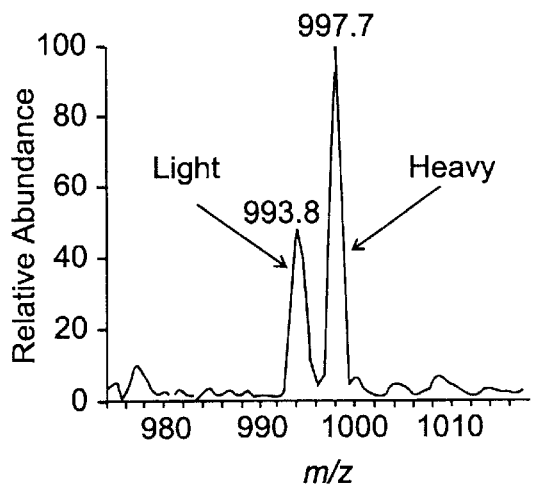
FIG. 3B shows an expanded view of the mass spectrum around one ion pair.
Figure 3C:
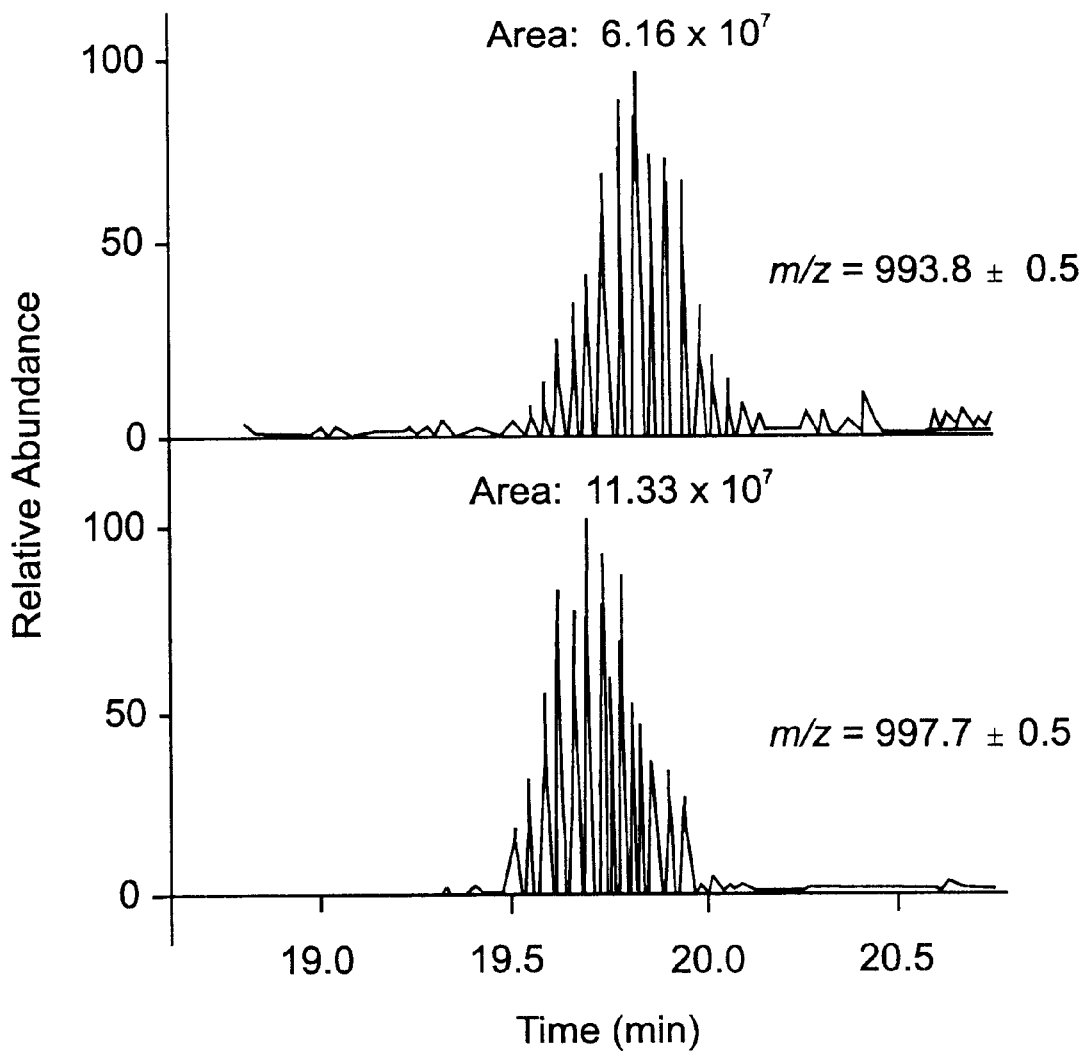
FIG. 3C shows the reconstructed ion chromatograms for each peak of the pair in FIG. 2.
Figure 4A:
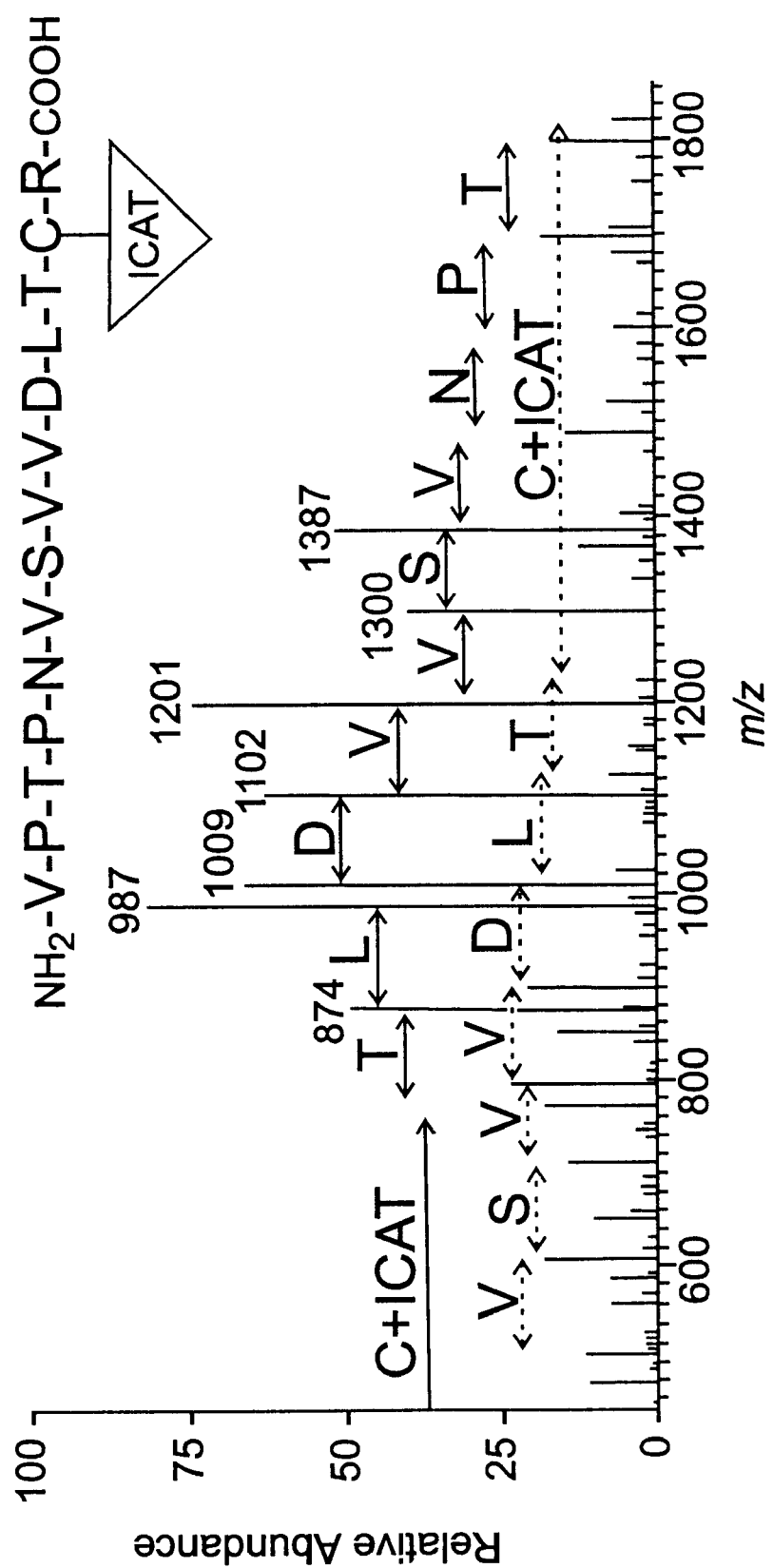
FIG. 4A shows the CID spectrum for one of the peaks of one of the peptides analyzed in FIG. 3.

The process is further illustrated for a single peptide pair in FIGS. 3A–C. A single scan of the mass spectrometer operated in MS mode is shown in FIG. 3A. Four pairs of peptide ions characterized by the mass differential encoded in the affinity tagged reagent are detected in this scan and indicated with their respective m/z values. The scan shown was acquired in 1.3 s. Over the course of the one-hour chromatographic elution gradient, more than 1200 such scans were automatically recorded. FIG. 3B shows an expanded view of the mass spectrum around the ion pair with m/z ratios of 993.8 and 977.7, respectively. Co-elution and a detected mass differential of four units potentially identifies the ions as a pair of doubly charged affinity tagged peptides of identical sequence (mass difference of eight and a charge state of two). FIG. 3C shows the reconstructed ion chromatograms for these two species. The relative quantities were determined by integrating the contour of the respective peaks. The ratio (light/heavy) was determined as 0.54 (Table 1). The peaks in the reconstructed ion chromatograms appear serrated because in every second scan the mass spectrometer switched between the MS and the $MS^n$ modes to collect sequence information (CID mass spectrum) of a selected peptide ion. These CID spectra were used to identify the protein from which the tagged peptides originated. FIG. 4A shows the CID spectrum recorded from the peptide ion with m/z=998 (marked with an arrow in FIG. 3A). Database searching with this CID spectrum identified the protein as glyceraldehyde-3-phosphate dehydrogenase (FIG. 4B) which was a member of the protein mixture.

Several beneficial features of the this method are apparent. First, at least two peptides were detected from each protein in the mixture. Therefore, both quantitation and protein identification can be redundant. Second, the identified peptides all contained at least one tagged cysteinyl residue. The presence of the relatively rare cysteinyl residue in a peptide adds an additional powerful constraint for database searching (Sechi, S. et al. (1998). Third, tagging and selective enrichment of cysteine-containing peptides significantly reduced the complexity of the peptide mixture generated by the concurrent digestion of six proteins. For this protein mixture, the complexity was reduced from 293 potential tryptic peptides to 44 tryptic peptides containing at least one cysteinyl residue. Fourth, the peptide samples eluted from the avidin affinity column are directly compatible with analysis by $\mu$LC-$MS^n$.

Quantitative Analysis of Protein Expression in Different Cell States

The protein reactive affinity reagent strategy was applied to study differences in steady-state protein expression in the yeast, *S. cerevisiae*, in two non-glucose repressed states (Table 3). Cells were harvested from yeast growing in log-phase utilizing either 2% galactose or 2% ethanol as the carbon source. One-hundred $\mu$g of soluble yeast protein from each cell state were labeled independently with the isotopically different affinity tagged reagents. The labeled samples were combined and subjected to the strategy described in Scheme 1. One fiftieth (the equivalent of approximately 2 μg of protein from each cell state) of the sample was analyzed.

Glucose repression causes large numbers of proteins with metabolic functions significant to growth on other carbon sources to be minimally expressed (Ronne, H. (1995; Hodges, P. E. et al. (1999)). Growth on galactose or ethanol with no glucose present results in the expression of glucose repressed genes. Table 3 presents a selection of 34 yeast genes encountered in the analysis, but it contains every known glucose-repressed genes that was identified (Mann, M. et al. (1994). Each of these genes would have been minimally expressed in yeast grown on glucose. Genes specific to both growth on galactose (GAL1, GAL 10) as well as growth on ethanol (ADH2, ACH1) were detected and quantitated.

The quantitative nature of the method is apparent in the ability to accurately measure small changes in relative protein levels. Evidence of the accuracy of the measurements can be seen by the excellent agreement found by examining ratios for proteins for which multiple peptides were quantified. For example, the five peptides found from PCK1 had a mean ratio ±95% confidence intervals of 1.57±0.15, and the percent error was <10%. In addition, the observed changes fit the expected changes from the literature (Ronne, H. 1995; Hodges, P. E. et al. (1999)). Finally, the observed changes are in agreement with the changes in staining intensity for these same proteins examined after two-dimensional gel electrophoresis (data not shown).

Figure 5A:
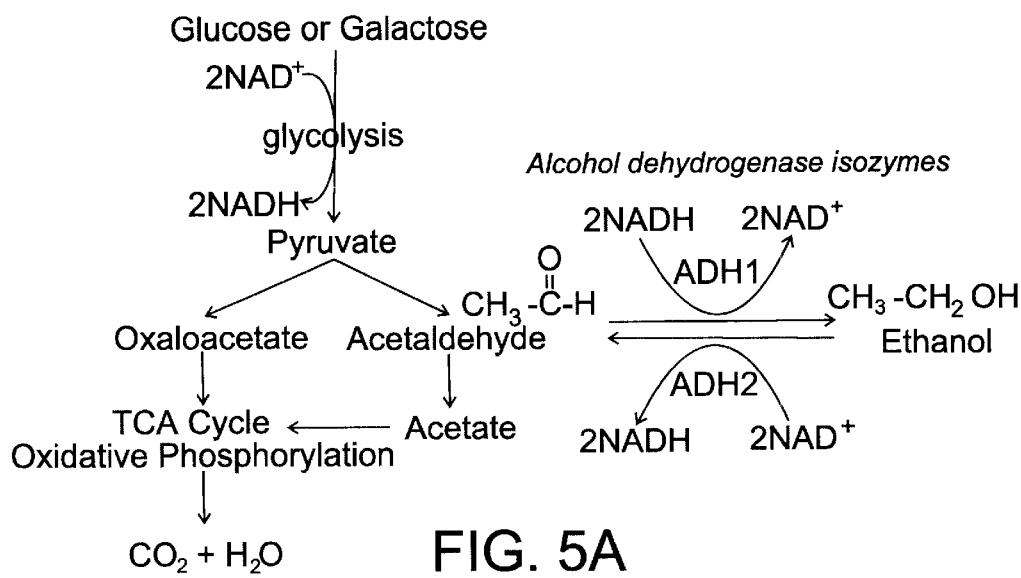
FIG. 5A shows the method by which yeast group on ethanol by converting ethanol into acetaldehyde which enters the TCA cycle.
Figure 5B:
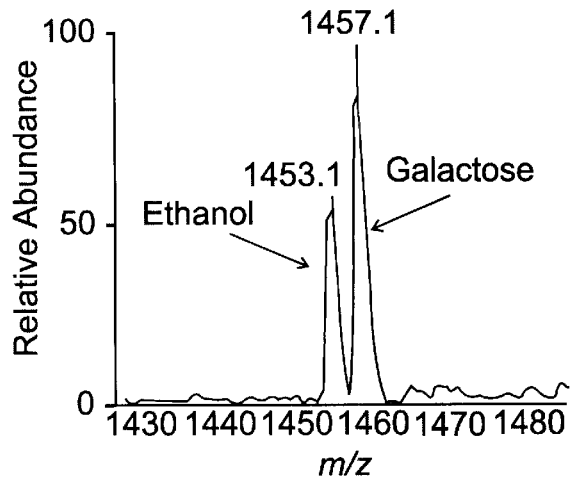
FIG. 5B shows the mass spectrum for ADH1 gene expression for yeast grown on ethanol or sugar.
Figure 5C:
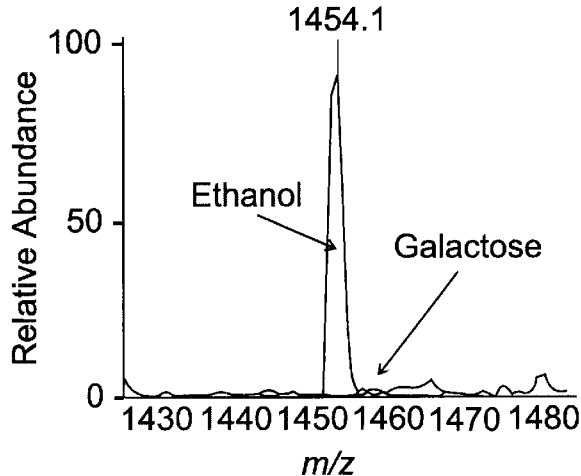
FIG. 5C shows the mass spectrum for ADH2 yeast gene expression for yeast grown on either ethanol or galactose.

The alcohol dehydrogenase family of isozymes in yeast facilitates growth on either hexose sugars (ADH1) and ethanol (ADH2). The gene ADH2 encodes an enzyme that is both glucose- and galactose-repressed and permits a yeast cell to grow entirely on ethanol by converting it into acetaldehyde which enters the TCA cycle (FIG. 5A). In the presence of sugar, ADH1 performs the reverse reaction converting acetaldehyde into ethanol. The regulation of these isozymes is key to carbon utilization in yeast (Ronne, H. (1995)). The ability to accurately measure differences in gene expression across families of isozymes is sometimes difficult using cDNA array techniques because of cross hybridization (DeRisi, J. L. et al. (1997)). The method of this invention applied as illustrated in Scheme 1 succeeded in measuring gene expression for each isozyme even though ADH1 and ADH2 share 93% amino acid (88% nucleotide) sequence similarity. This was because the affinity tagged peptides from each isozyme differed by a single amino acid residue (valine to threonine) which shifted the retention time by more than 2 min and the mass by 2 daltons for the ADH2 peptides (FIG. 5B). ADH1 was expressed at approximately 2-fold high levels when galactose was the carbon source compared with ethanol. Ethanol-induction of ADH2 expression resulted in more than 200-fold increases compared with galactose-induction.

The results described above illustrate that the method of this invention provides quantitative analysis of protein mixtures and the identification of the protein components therein in a single, automated operation.

The method as applied using a sulfhydryl reactive reagent significantly reduces the complexity of the peptide mixtures because affinity tagged cysteine-containing peptides are selectively isolated. For example, a theoretical tryptic digest of the entire yeast proteome (6113 proteins) produces 344, 855 peptides, but only 30,619 of these peptides contain a cysteinyl residue. Thus, the complexity of the mixture is reduced, while protein quantitation and identification are still achieved. The chemical reaction of the sulfhydryl reagent with protein can be performed in the presence of urea, sodium dodecyl sulfate (SDS), salts and other chemicals that do not contain a reactive thiol group. Therefore, proteins can be kept in solution with powerful stabilizing agents until they are enzymatically digested. The sensitivity of the μLC-MS$^n$ system is dependent of the sample quality. In particular, commonly used protein solubilizing agents are poorly compatible or incompatible with MS. Affinity purification of the tagged peptides completely eliminates contaminants incompatible with MS. The quantitation and identification of low abundance proteins by conventional methods requires large amounts (milligrams) of starting protein lysate and involves some type of enrichment for these low abundance proteins. Assays described above, start with about 100 μg of protein and used no fractionation techniques. Of this, approximately 1/50 of the protein was analyzed in a single μLC-MS$^n$ experiment. This system has a limit of detection of 10–20 fmol per peptide (Gygi, S. P. et al. (1999)). For this reason, in the assays described which employ μLC-MS$^n$ only abundant proteins are detected. However, the methods of this invention are compatible with any biochemical, immunological or cell biological fractionation methods that reduce the mixture complexity and enrich for proteins of low abundance while quantitation is maintained. This method can be redundant in both quantitation and identification if multiple cysteines are detected. There is a dynamic range associated with the ability of the method to quantitate differences in expression levels of affinity tagged peptides which is dependent on both the intensity of the peaks corresponding the peptide pair (or set) and the overall mixture complexity. In addition, this dynamic range will be different for each type of mass spectrometer used. The ion trap was employed in assays described herein because of its ability to collect impressive amounts of sequencing information (thousands of proteins can potentially be identified) in a data-dependent fashion even though it offers a more limited dynamic quantitation range. The dynamic range of the ion trap (based on signal-to-noise ratios) varied depending on the signal intensity of the peptide pair and complexity of the mixture, but differences of up to 100-fold were generally detectable and even larger differences could be determined for more abundant peptides. In addition, protein expression level changes of more than 100–200-fold still identify those proteins as major potential contributors of the phenotypic differences between the two original cell states. The method can be extended to include reactivity toward other functional groups. A small percentage of proteins (8% for S. cerevisiae) contain no cysteinyl residues and are therefore missed by analysis using reagents with sulfhydryl group specificity (i.e., thiol group specificity). Affinity tagged reagents with specificities toward functional groups other than sulfhydryl groups will also make cysteine-free proteins susceptible to analysis.

The methods of this invention can be applied to analysis of low abundance proteins and classes of proteins with particular physico-chemical properties including poor solubility, large or small size and extreme pI values.

The prototypical application of the chemistry and method is the establishment of quantitative profiles of complex protein samples and ultimately total lysates of cells and tissues following the preferred method described above. In addition the reagents and methods of this invetion have applications which go beyond the determination of protein expression profiles. Such applications include the following:

Application of amino-reactive or sulfhydryl-reactive, differentially isotopically labeled affinity tagged reagents for the quantitative analysis of proteins in immuno precipitated complexes. In the preferred version of this technique protein complexes from cells representing different states (e.g., different states of activation, different disease states, different states of differentiation) are precipitated with a specific reagent, preferably an antibody. The proteins in the precipitated complex are then derivatized and analyzed as above.

Application of amino-reactive, differentially isotopically labeled affinity tagged reagents to determine the sites of induced protein phosphorylation. In a preferred version of this method purified proteins (e.g., immunoprecipitated from cells under different stimulatory conditions) are fragmented and derivatized as described above. Phosphopeptides are identified in the resulting peptide mixture by fragmentation in the ion source of the ESI-MS instrument and their relative abundances are determined by comparing the ion signal intensities of the experimental sample with the intensity of an included, isotopically labeled standard.

Amino-reactive, differentially isotopically labeled affinity tagged reagents are used to identify the N-terminal ion series in $MS^n$ spectra. In a preferred version of this application, the peptides to be analyzed are derivatized with a 50:50 mixture of an isotopically light and heavy reagent which is specific for amino groups. Fragmentation of the peptides by CID therefore produces two N-terminal ion series which differ in mass precisely by the mass differential of the reagent species used. This application dramatically reduces the difficulty in determining the amino acid sequence of the derivatized peptide.

Quantitative Analysis of Surface Proteins in Cells and Tissue

The cell exterior membrane and its associated proteins (cell surface proteins) participate in sensing external signals and responding to environmental cues. Changes in the abundance of cell surface proteins can reflect a specific cellular state or the ability of a cell to respond to its changing environment. Thus, the comprehensive, quantitative characterization of the protein components of the cell surface can identify marker proteins or constellations of marker proteins characteristic for a particular cellular state, or explain the molecular basis for cellular responses to external stimuli. Indeed, changes in expression of a number of cell surface receptors such as Her2/neu, erbB, IGFI receptor, and EGF receptor have been implicated in carcinogenesis and a current immunological therapeutic approach for breast cancer is based on the infusion of an antibody (Herceptin, Genentech, Palo Alto, Calif.) that specifically recognizes Her2/neu receptor.

Cell surface proteins are also experimentally accessible. Diagnostic assays for cell classification and preparative isolation of specific cells by methods such as cell sorting or panning are based on cell surface proteins. Thus, differential analysis of cell surface proteins between normal and diseased (e.g., cancer) cells can identify important diagnostic or therapeutic targets. While the importance of cell surface proteins for diagnosis and therapy of cancer has been recognized, membrane proteins have been difficult to analyze. Due to their generally poor solubility they tend to be under-represented in standard 2D gel electrophoresis patterns and attempts to adapt 2D electrophoresis conditions to the separation of membrane proteins have met limited success. The method of this invention can overcome the limitations inherent in the traditional techniques.

The analysis of membrane proteins is challenging because they generally are difficult to maintain in solution under conditions that are compatible with high sensitivity analytical instruments such as mass spectrometers. The application of the methods of the present invention to the analysis of membrane proteins is exemplifed using human T cell lymphoma cell line Jurkat for membrane protein labeling and extraction and the well characterized human prostate epithelial cell line P69SV40T and two P69SV40T sublines which differ in IGF-1 receptor expression by factor of 10 to exemplify quantitative, differential analysis of membrane proteins.

Jurkat cells are an appropriate model system because the cells are easy to grow in large numbers and because the modulation of cell surface proteins in response to different stimuli and experimental conditions has been well characterized in T lymphocytes. Commercially available biotinylating reagents or more general affinity tagging reagents are employed to derivatize lysine residues and the free N-termini. Water soluble biotinylating reagents such as Sulfo-NHS (N-hydroxy succinimide) biotin and analogs (Sulfosuccinimidyl-6-(biotinamido)-hexanoate, Pierce, Rockford, Ill.) which have been used extensively for labeling cell surface proteins can be employed. The reaction of NHS esters with primary amines is best at neutral pH values and above and is compatible with the presence of organic solvent such as DMSO or DMF. Biotinylation of cell surface proteins from the Jurkat cells is carried out in PBS buffer at pH 7.2. Cells ($1\times10^7$) are washed with PBS buffer to remove contaminating serum and other proteins from the culture medium. The cells are resuspended at $25\times10^6$ cell/ml and reacted with 0.5 mg/ml of Sulfo-NHS-Biotin (Pierce, Rockford, Ill.) for 30 min at RT. The labeled cells are washed twice with cold PBS to remove unreacted biotinylating reagent. Biotinylated cells are solubilized at $5\times10^7$ cells/ml in lysis buffer containing 1% Triton X-114. Triton X-114 has the property of phase-partitioning into detergent phase and aqueous phase at 30° C. Following the phase partitioning, detergent phase is removed from the aqueous phase by centrifugation at 300×g. Phase partitioning has previously been successfully used to enrich cell membrane. Also, this technique was found to enrich membrane proteins from Jurkat cell lysates. Triton phase is diluted 1:5 (v/v) using 50 mM ammonium bicarbonate buffer, pH 8.5, and high-purity, modified porcine-trypsin is added to digest the proteins at a concentration of 12.5 ng/ml for overnight at 37° C. Trypsin is neutralized by the addition of a cocktail of serine protease inhibitors and tryptic peptides are isolated by the avidin affinity chromatography techniques. Eluted peptides are separated e.g., by $\mu$LC methods and identified by searching peptide sequence databases, using for example, the Sequest program.

The human prostate epithelial cell line P69SV40T which was immortalized with SV 40 T antigen has been well characterized. This cell line is immortal but not tumorigenic and expresses type 1 insulin like growth factor receptor (IGF-1R) at $2\times10^4$ receptors per cell. A subline, called M12, was derived from P69SV40T by sequential passage in male athymic nude mice. This cell line is highly tumorigenic and metastatic and expresses $1.1\times10^3$ IGF-1R per cell. The relative difference in the abundance of IGF-1R in the cell lines P69SV40T and M12 can be quantitatively determined using methods of this invention adapted for application to membrane proteins. Since the number of IGF-1R for these cell lines has already been determined, this well characterized system can provide a reference to validate the efficiency of the quantitative methods of this invention P69SV40T cells ($1\times10^7$) are biotinylated with an isotopically heavy biotin tagged amino reactive reagent and the M12 cells ($1\times10^7$) are biotinylated with a corresponding isotopically light amine reactive biotin tagged amino reactive reagent. IGF-1R is then immunoprecipitated from the combined lysate of both cell lines using an antibody against human IGF-1R and the total mass of immunoprecipitated proteins is digested with trypsin. Trypsin is then neutralized, e.g., by the addition of inhibitors and tagged peptides are purified by biotin-avidin affinity chromatography. The eluted peptides are analyzed by LC-MS and LC-MS$^n$ for peptide quantitation and identification, respectively, as has been described above. Quantitation in this experiment is facilitated by the option to use selective ion monitoring in the MS. In this mode only the masses of tagged peptide ions expected to derive from IGF-1R need be monitored.

The described technique can be applied to compare the differences in relative abundance of cell surface proteins between parental prostate cell line (P69SV40T) and M12 cells to detect and identify those cell surface proteins whose expression level is different in the two cell lines and which may be characteristic of the different cell states. Using the methods described herein, global, relative quantitation of the cell surface proteins in any two or more cell lines can be analyzed to detect and identify those cell surface proteins characteristic of the different cell states. Results can be independently confirmed using procedure such as ID or 2D gels, if applicable, or quantitative western blotting to confirm quantitation results.

It is expected that the experimental variability of quantitation of cell surface proteins will be considerably better than the accuracy of quantitation achieved by currently available cDNA array technology. In addition to relative protein quantity and identity, the method can also be used to reveal the orientation of the protein in the membrane, based on the presumption that intact, alive cells will exclude the biotinylating reagent.

Alternative methods can be applied to enhance the selectivity for tagged peptides derived from cell surface proteins. For example, tagged cell surface proteins can be trypsinized directly on the intact cells to generate tagged peptides, purified and analyzed as discussed. In addition, traditional cell membrane preparations may be used as an initial step to enrich cell surface proteins. These methods can include gentle cell lysis with a dounce homogenizer and series of density gradient centrifugations to isolate membrane proteins prior to proteolysis. This method can provide highly enriched preparations of cell surface proteins. Affinity tagged proteins may also be isolated by affinity chromatography prior to proteolysis as well as after proteolysis. This chromatography can be performed in the presence of surfactants such as TX-100, NP-40 or Tween-20 to maintain protein solubility. The sequential application of affinity chromatography steps (one for the intact protein and one for the tagged peptide fragments) provides a high degree of selectivity. These alternative methods are easily scalable for the detection of low abundance membrane proteins and the relative quantity of tagged peptides tagged is maintained through the selective enrichment steps.

In the application of the methods of this invention to cell surface proteins, once the tagged proteins are fragmented, the tagged peptides behave no differently from the peptides generated from more soluble samples.

Synthesis of Affinity Tagged Protein Reactive Reagents that are Selective for Certain Protein Groups Synthetic routes exemplary affinity tagged reagents suitable for use in the methods of this invention are provided in Schemes 2–3 where well-known synthetic techniques are employed in synthesis of the non-deuterated and deuterated reagents.

Biotinyl-iodoacetylamidyl-4,7,10 trioxatridecanediamine 4 (Scheme 3) consists of a biotin group, a chemically inert spacer of capable of being isotopically labeled with stable isotopes and a iodoacetamidyl group, respectively. The biotin group is used for affinity enrichment of peptides derivatized with the reagent, the ethylene glycol linker is differentially isotopically labeled for mass spectral analysis and the iodoacetamidyl group provides specificity of the reagent for sulfhydryl-containing peptides. The reagent can be synthesized in an all hydrogen form (isotopically light form) with and with 1–20, and preferably 4–8 deuterium atoms in the linker (isotopically heavy forms).

Analysis of Velocities of Multiple Enzymes in Cell Lysates

Monitoring enzyme functions by biochemical assays is an essential diagnostic tool that employs a multitude of analytical techniques including spectrophotometric, fluorometric, and radiometric detection of products. However, current methods are difficult to use for assaying several enzymes simultaneously in a single sample. Mass spectrometry for quantification of a collection of metabolites in biological fluids has emerged as a powerful approach for the analysis of birth defects (Morris et al., 1994), but this analytical technique has not been developed for the direct analysis of rates of individual enzymatic steps. The analytical method described herein for monitoring and quantification of enzymatic activities in cell homogenates and other biological samples permits simultaneous (multiplex) monitoring of multiple reactions, and can be readily automated.

A feature of the method of this invention as applied to enzyme assays is the use of electrospray ionization mass spectrometry (ESI-MS) (Cole et al., 1997) for the simultaneous detection of enzymatic products and chemically identical internal standards, which are distinguished by stable isotope (deuterium) labeling. A second feature is the use of affinity tagged reagents containing an enzyme substrate which when combined with affinity purification provide for facile capture of enzymatic products from crude biological fluids. The affinity tagged reagents are designed to contain a target substrate for an enzyme of interest that is covalently attached to an affinity tag via a linker. Action of the enzyme of interest on the substrate conjugate causes cleavage or other modification that changes its molecular mass (Scheme 4). The change of mass is detected by ESI-MS. The linker and and affinity tag used preferably facilitate ionization by ESI, block action of other enzymes in the biological fluid, and allow highly selective capture from the complex matrix for facile purification.

An example of this approach is the design and synthesis of affinity tagged enzyme substrate reagents 1 and 2 (Scheme 5) to simultaneously assay lysosomal β-galactosidase and N-acetyl-α-D-glucosaminidase, respectively. Deficiency of the former enzyme results in one of the lysosomal storage diseases, $GM_1$-gangliosidosis, a condition that occurs in the population with a frequency of about 1 in 50,000 and leads to early death of affected children. Deficiency of N-acetyl-R-D-glucosaminidase results in the rare lysosomal storage disorder Sanfilippo syndrome type B. This example has been described in Gerber et al. (1999) J. Amer. Chem. Soc. 121: 1102–1103 which is incorporated by reference herein in its entirety.

Conjugates 1 and 2 consist of biotin as an affinity tag, which is coupled to sarcosine. Biotin allows highly specific capture of the substrate conjugate through non-covalent binding to streptavidin immobilized on agarose beads (Bayer et al., 1990). Sarcosine provides an N-methylated amide linkage to biotin to block the enzyme biotinidase, which is often present in the cellular fluids and could cause cleavage of the conjugate molecule during the assay (Wilbur et al., 1997). In addition, it was found that biotinyl-sarcosine conjugates can be displaced from streptavidin by addition of biotin. The N-biotinylsarcosine block is linked to a polyether diamine, the length of which can be varied to avoid mass/charge overlaps of products and internal standards. The linker also allows facile introduction of multiple deuterium atoms (i.e., 8 deuteriums in 5 and 4 in 6, Scheme 5) to permit the synthesis of internal standards. The d8-linker was made by reacting DOCH2CH2OCH2CH2OD with CD2 dCDCN in benzene with catalytic NaOD (Ashikaga, K.; Ito, S.;Yamamoto, M.; Nishijima, Y. *Bull. Chem. Soc. Jpn.* 1988, 61, 2443–2450) and the resulting dinitrile was reduced to the diamine with Ra—Ni. The d4-linker was made in the same way using ethylene glycol and CD2 dCDCN in CH3CN and catalytic NaOH.

In addition, the linker is hydrophilic to ensure good water solubility of the substrate conjugate, and it has basic groups which are efficiently protonated by ESI and thus ensure sensitive detection by mass spectrometry. The target carbohydrate substrates are attached to the polyether linker by a β-alanine unit (Scheme 5). The enzymatic product conjugates 3 and 4 are also shown Scheme 5. Conjugates 1 and 2 were prepared as shown in Scheme 5. All reagents were purified to homogeneity by reverse-phase HPLC and characterized by high-field 1H-NMR and ESI-MS. The substrate was linked to the diamine spacer by Michael addition of the latter onto the p-acryloylamidophenyl glycoside, (Romanowska et al., 1994) and the intermediate was coupled with the tetrafluorophenyl ester of N-biotinylsarcosine (Wilbur et al., 1997).

The ESI-MS assay of β-galactosidase and N-acetyl-R-D-glucosaminidase is based on enzymatic cleavage of the glycosidic bond to release monosaccharide and conjugates 3 and 4 (mass differences are 162 and 203 Da, respectively). In a typical procedure, 0.2 mM 1 and 0.3 mM 2 were incubated with sonicated cultured fibroblasts from individual patients with β-galactosidase deficiency and with fibroblasts cultured from unaffected people. After incubation, labeled internal standards 5 and 6 were added, and the biotinylated components were captured on streptavidin-agarose beads. Quantitative strepavidin capture efficiency from a cell homogenate was observed with model reagents. After purification by multiple washings to remove nonspecifically bound components, the biotinylated products were released by free biotin, and the eluant was analyzed by ESI-MS. About 85% release of the biotinylated products was observed after incubation with excess biotin for 90 min. A blank was obtained by quenching the assay with all components present at time zero.

A typical procedure, cell protein (75 $\mu$g) in 15 $\mu$L of water was added to 15 $\mu$L buffer (0.1 M Na citrate, pH 4.25) containing 2 (0.3 mM) and 1 (0.2 mM, added 5 h after addition of cell protein). After incubation for 5.5 h at 37° C., the reaction was quenched by addition of 200 $\mu$L of 0.2 M glycine carbonate buffer, pH 10.3, and 5 and 6 (1 nmol each) were added. After centrifugation to remove cell debris, the supernatant was loaded onto a bed of streptavidin-agarose (7 nmol biotin binding capacity, Pierce) in a small filtration device (micro BioSpin, Bio-Rad). After 5 min, filtration was effected by centrifugation, and the gel bed was washed with 0.1% Triton X-100 (about 1 min incubation, then spin) and then six times with purified water (Milli-Q, Millipore). Elution was carried out in 25 $\mu$L of 50% methanol containing 56 nmol of free biotin (1–10 h incubation, then spin). Filtrate was diluted 4-fold with 50% methanol/water, and 1 $\mu$L was analyzed by ESI-MS.

Figure 6A:
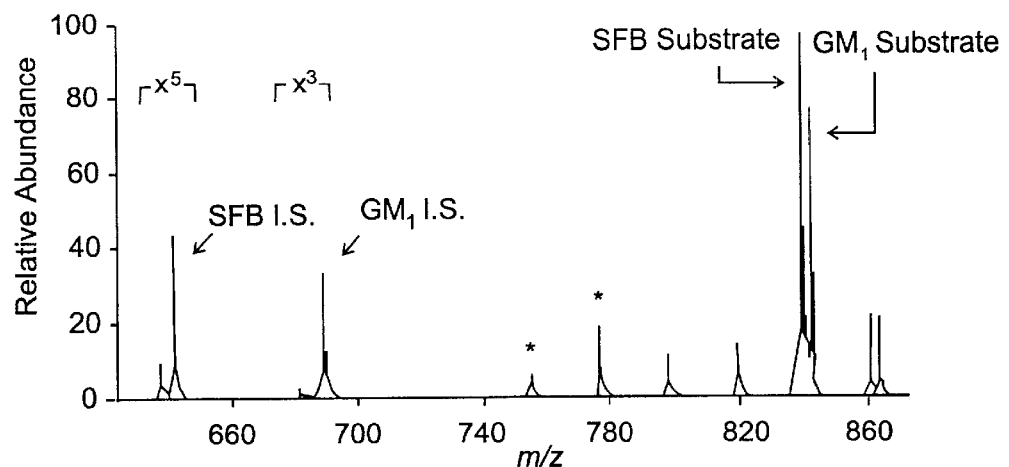
FIGS. 6A–6C represent the clinical analysis of patient samples for GM1 and SFB. See "Clinical Enzymology Assays."
Figure 6B:
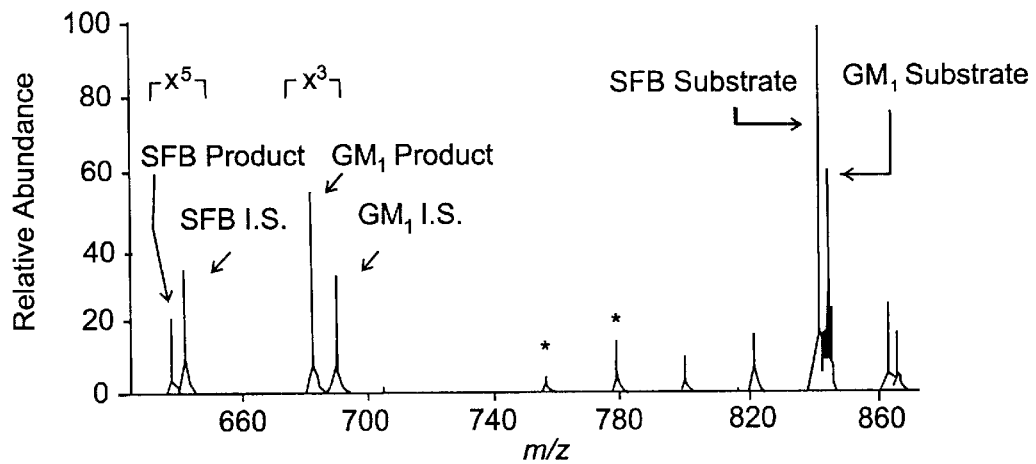
Figure 6C:
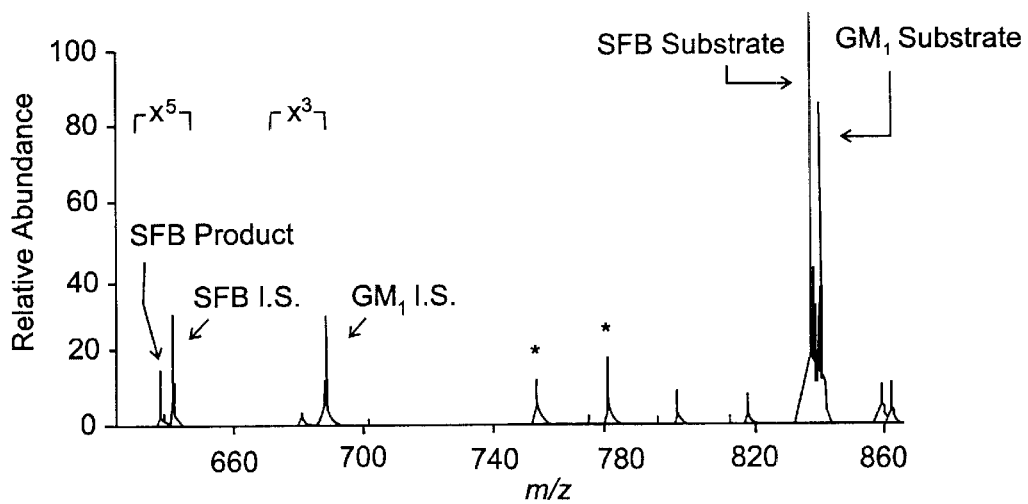

The ESI-MS spectrum of the blank (FIG. 6A) is remarkably simple, showing peaks of the (M+H)$^+$ ions from reagents 1 and 2 (m/z 843 and 840), internal standards 5 and 6 (m/z 689 and 641), and trace amounts of products 3 and 4 (m/z 681 and 637). Ions due to clusters of biotin also appear in the spectrum but did not interfere with the analysis. The presence of nondeuterated products in the blank may be due to nonenzymatic substrate reagent hydrolysis during sample work up or to collision-induced dissociation of the substrate ion in the gas phase. A MS/MS spectrum of the (conjugate 1+H)$^+$ ion at m/z 843 gave a prominent fragment of (conjugate 3+H)$^+$ at m/z 681 (spectrum not shown). The ESI-MS spectrum of a sample incubated with cell homogenate from a healthy individual clearly shows the β-galactosidase product at m/z 681 and the N-acetyl-α-D-glucosaminidase product at m/z 637 (FIG. 6B). Triplicate enzymatic reactions using cells from a healthy patient yielded a β-galactosidase specific activity of 51±3 nmol/h/(mg cell protein) and an N-acetyl-α-D-glucosaminidase specific activity of 1.4±0.3 nmol/h/mg. Time course studies confirmed that the initial reaction velocities were being measured. Values obtained with cells from six healthy individuals ranged from 36±4 to 68±3 nmol/h/mg for β-galactosidase and 0.9±0.05 to 2.3±0.4 nmol/h/mg for N-acetyl-α-D-glucosaminidase. In contrast, very little enzymatic product above the blank level (0.9±0.9 and 0.8±0.6 nmol/h/mg) was observed when cells from two patients with β-galactosidase deficiency were used, whereas N-acetyl-α-D-glucosamini-dase activity is clearly detected (FIG. 6C). These spectra were obtained with 0.75 $\mu$g of cell protein, corresponding to ~1000 fibroblasts. Thus the ESI-MS method has very high sensitivity for biomedical applications.

ESI-MS was carried out on a Finnigan LCQ ion trap instrument. Data were collected in full scan mode from mlz 625 to 875 by direct infusion at 1.5 $\mu$L/min. Specific activities were obtained from the ratio of product to internal standard ion peak areas (averaged over 30 scans).

The approach described for assaying enzymes using substrate reagents and ESI-MS can be broadly applied. The multiplex technique can be expanded to assay dozens or more enzymes simultaneously in a single reaction, obviating the need for multiple assays to assist in confirming diagnoses of rare disorders. The method can be used to measure several enzymes simultaneously when evaluating the rate of chemical flux through a specific biochemical pathway or for monitoring biochemical signaling pathways. The affinity tag-capture reagent method for isolation of affinity tagged reaction products and substrates from complex mixtures is technically simple and can be readily automated, particular when biotin-strepavidin is employed. Because of the high sensitivity of the ESI-MS detection employed, which requires only sub-microgram quantities of the substrate reagents per assay, the synthesis of several hundred substrate reagents on a low-gram scale becomes practical and economical. Since most enzyme active sites are exposed to solvent, it is possible to attach an affinity tagged linker to most enzyme substrates while preserving enzymatic activity. Scheme 6 provides the structures of several additional enzyme substrates, suitable for use in this method, indicating by arrows allowable positions for tag attachment sites. Allowable tag sites for additional enzyme substrates can be determined by review of X-ray crystal structures of enzyme-substrate or enzyme-substrate analog structures. Using a standard computer graphics program, available X-ray data and by attaching an extended chain butyl group (as a model for the affinity tagged linker) to potential tag attachment sites, suitable attachment sites that show there are no enzyme-atoms in van der Waals overlap with the model tag can be predicted.

Analogous methods to those described above can be applied to the analysis of enzymes associated with other Sanfillipo Syndromes (A, C and D). SFA is associated with heparan sulfamidase, SFC is associated with acetyl-CoA-alpha-glucosaminide N-acetyltransferase and SFD is associated with N-acetylglucosamine 6-sulfatase. Exemplary affinity tagged enzyme substrate reagents useful in the analysis of these enzymes and the diagnosis of these disorders are provided below. The methods can also be applied of the diagnosis of Niemann-Pick Type A and B disease by assaying for acid sphingomyelinase and to the diagnosis of Krabbe disease by assaying for galactocerebroside beta-galactosidase. These enzymes are currently assayed employing fluorphore-derivatived reagents as indicated in Scheme 7. Enzyme substrate reagents for assay of these enzymes in the methods herein can be readily prepared by replacement of the fluorophore with an A-L group herein. This approach to preparation of affinity tagged enzyme substrates is generally applicable to any known fluorophore-derivatized enzyme substrate or substrate analog.

Table 4 provides exemplary enzymes that are associated with certain birth defects or disease states. These enzymes can be assayed by the methods described herein.

Assaying Enzymatic Pathways for Carbohydrate-Deficient Glycoprotein Syndromes (CDGS)

The methods and reagents of this invention can be employed to quantify the velocities of multiple enzymes pertinent to diagnosis of CDGS diseases.

CDGS Type Ia and Ib are caused by the deficiency or absence of the enzymes phosphomannoisomerase (PMIb) (Type Ib) and phosphomannomutase (PMM2) (Type Ia) which are part of a multistep pathway (Scheme 8) for conversion of glucose to mannose-1-phosphate (Freeze, 1998). The monosaccharide substrates involved in the pathway are fructose-6-phosphate, mannose-6-phosphate, and mannose-1-phosphate. These monosaccharides can be somewhat difficult to convert to substrate conjugates because it is not a priori clear which atom on the sugar should be conjugated with the linker without impairing enzyme activity. PMIb and PMM2 can, however, be assayed indirectly. Mammalian cell microsomes contain dolichol-P-mannose synthase which catalyzes the reaction of dolichol-phosphate with GDP-mannose to form dolichol-P-mannose and GDP (Scheme 8, Chapman et al. 1980). This synthase can be assayed using the methods of this invention, specifically with a biotin-linker substrate. Microbial PMM and the enzyme which makes GDP-mannose from GTP and mannose-1-P, GDP-mannose pyrophosphorylase, are readily purified from bacteria and yeast (Glaser, 1966, Preiss, 1966), and these enzymes can be supplied exogeneously to the enzyme assay. If PMIb activity is deficient, little or no mannose-6-P will be made when the reaction sequence is started by addition of fructose-6-P. Without mannose-6-P, mannose-1-P and GDP-mannose will not be made, and thus no conjugated-dolichol-P-mannose will be detected by ESI-MS. Exogenous GTP is supplied as a requirement for the GDP-mannose pyrophosphorylase step, and ATP is omitted so that mannose-6-P cannot be made from mannose. To assay PMM2, the reaction sequence is initiated with mannose-6-P, and PMM2 deficiency results in the failure to make conjugated-dolichol-P-mannose.

The carrier dolichol is a ~60- to 105-carbon isoprenoid. Evidence is accumulating that many enzymes that operate on carbohydrates attached to dolichol chains are tolerant to significant shortening of the dolichol chain; even 10- and 15-carbon dolichols are tolerated (Rush and Wachter, 1995). It appears that such enzymes act on the water-soluble carbohydrate portion of the dolichol conjugate and thus have little or no requirement to bind the dolichol anchor. Based on this, an affinity labeled substrate for the direct assay of dolichol-P-mannose synthase and the indirect assay of PMIb and PMM2 is prepared by attaching an affinity labeled linker to the non-polar end of a short dolichol, such as the 10-carbon dolichol analog citronellol.

The synthesis of a biotinylated dolichol$_{10}$-substrate conjugate containing a sarcosinyl linker (B-S-Dol$_{10}$-P) is shown in Scheme 9. Protected citronellol (R=t-BuSiMe$_2$) is regioselectively oxidized at the terminal alyllic methyl group (McMurry and Kocovsky, 1984), and the allylic alcohol is coupled with biotinylsarcosine active ester (R=CH$_3$). The citronellol 1-hydroxy group is subsequently deprotected and phosphorylated with POCl$_3$ (Rush and Wachter, 1995). In a parallel synthesis, d$_5$-sarcosine, CD$_3$NHCD$_2$COOH, is used to prepare the isotopically labeled (heavy) reagent for use as an internal standard. d$_5$-Sarcosine is readily prepared from commercially available materials (BrCD$_2$COOD and CD$_3$NH$_2$) using standard synthetic techniques.

The deuterated internal standard, B-d$_5$-S-Dol$_{10}$-P-Mannose, is synthesized enzymatically by incubating hen oviduct microsomes with GDP-mannose and the synthetic B-d$_5$-S-Dol$_{10}$-P substrate conjugate (Rush and Waechler, 1995). An added advantage of the B-S-conjugate is that it allows for a facile affinity purification of the microsomal mannosylated product by specific capture on agarose-streptavidin beads followed by elution with free biotin.

This method employing affinity tagged short dolichol analogues is generally applicable for assaying other enzymes that operated on dolichol anchored carbohydrates. Such an approach is useful for the subsequent identification of enzyme deficiencies present in other types of CDGS that have not been yet identified.

CDGS Type II results from defective GlcNAc transferase II (GlcNAc-T II) which transfers GlcNAc from UDP-GlcNAc to the 2-position of a mannose residue in the intermediate branched oligosaccharide (the Core Region) in the process of building up the disialo-biantennary chain (Scheme 10) (Schachter, 1986, Brockhausen et al, 1989). GlcNAc transferase II is one of the six known enzymes that mediate highly regiospecific glycosylation of the mannose residues in the Core Region. The Core Region is anchored at the reducing end of chitobiosylasparagine, where the asparagine residue is part of the peptide chain of the glycosylated protein. The latter structure unit in the substrate can be replaced by a hydrophobic chain without loss of enzyme activity (Kaur et al, 1991). Thus, the substrate conjugate for CDGS Type II is assembled by linking an affinity-labeled linker group to the reducing end of chitobiosylasparagine. However, the latter structure unit in the substrate can be replaced by a hydrophobic chain without loss of enzyme activity (Kaur et al, 1991). For example, commercially available α-D-mannopyranosylphenylisothiocyanatecan be coupled to a biotin-labeled linker and the 5,6-hydroxyls are selectively protected as illustrated in Scheme 11 (Paulsen and Meinjohanns, 1992). Coupling of the equatorial 3-OH with per-O-acetylmannosyl-1-trichloroacetamidate (Paulsen et al, 1993) will provide a disaccharide conjugate (Scheme 12). If a minor amount of coupling occurs at the axial 2-OH group the products can be separated by HPLC. After deprotection, the primary 6-OH is coupled with a second equivalent of per-O-acetylmannosyl-1-trichloroacetamidate to yield the Core Region conjugate. Deprotection of the O-acetyl groups yields the substrate conjugate for GlcNAc transferase I which can be converted to the GlcNAc-T II substrate by enzymatic glycosyl transfer using a Triton X-100 rabbit liver extract, a reaction that has been carried out on apreparative scale (Kaur et al. 1981).

The synthesis of the deuterium labeled derivative needed for the internal standard is performed in parallel by using a labeled PEG-diamine building block (Gerber et al, 1999). The biotinylated trisaccharide is converted to the tetrasaccharide (product of GlcNAc-T II) by incubation with UDP-GlcNAc and transferase II ( (Kaur and Hindsgaul, 1991, Tan et al, 1996) and utilizing the B-S handle for affinity purification of the enzymatic products.

CDGS Type V

The lipid-linked oligosaccharide (LLO) that is transferred to the Asn residue of the glycosylated protein is composed of 2 GlcNAc, 9 mannoses, and 3 glucoses. It has recently been shown that microsomes from CDGS type V patients are greatly deficient in the enzyme that transfers one or more glucose residues during LLO biosynthesis (Korner et al, 1998). Since the transferase that attaches the carbohydrate unit of LLO to the Asn residue discriminates against the glucose-deficient LLO, CDGS Type V patients have fewer numbers of carbohydrate units atached to glycoproteins, such as transferrin (Korner et al, 1998). However, the few carbohydrate units that are present are full-length, demonstrating that residual glucosyl transfer occurs in type V CDGS patients (Korner et al, 1998). Thus, quantification of the rate of Asn glycosylation by ESI-MS would constitute a viable assay of CDGS Type V syndrome.

Synthetic peptides with 3–7 amino acid residues containing the Asn-Xaa-Ser/Thr sequence have been shown to be good substrates for glycosylation (Ronin et al., 1981). The strategy for the ESI-MS assay of the oligosaccharide transferase relies on a B-S conjugate of an appropriate peptide containing the Asn-Xaa-Ser/Thr sequence (Scheme 13). A heptapeptide, $NH_2$-Tyr-Gln-Ser-Asn-Ser-Thr-Met-$NH_2$ (SEQ ID NO. 1) has shown high activity in a previous study (Ronin et al, 1981). The peptide is readily available by standard peptide synthesis using an in-house automatic synthesizer. The heptapeptide and its glycoconjugates can be ionized by ESI to provide stable singly-charged ions. Coupling of BS-tetrafluorophenyl ester with $NH_2$-Tyr-Gln-Ser-Asn-Ser-Thr-Met-$NH_2$ (SEQ ID NO. 1) will directly yield the substrate for the transferase. Several products are expected from the enzymatic glycosylation and subsequent modifications of the oligosaccharide antenna. The products can be prepared enzymatically by incubating thyroid rough microsomes with BS-Tyr-Gln-Ser-Asn-Ser-Thr-Met-$NH_2$ and Dol-P-Glu (Ronin et al, 1981a), followed by affinity purification of the biotinylated products. Product distribution due to different degrees of glycosylation can be monitored by ESI-MS, and the major components can be purified by HPLC. An analogous procedure using a B-N($CD_3$)$CD_2$CO— conjugate is used to prepare deuterated internal standards.

The molecular masses of the ionized substrate conjugates for the set of enzymes assayed for CDGS Ia, Ib, II, and V syndromes, as well as products and internal standards are compiled in Table 5, which shows that no isobaric overlaps among the $(M+H)^+$ species occur. The close spacing between the $(M+Na)^+$ ion from the Type Ia,b product and the $(M+H)^+$ ion of the demannosylated B-(N-$C_2D_5$)-2,2-$D_2$-Gly-$Dol_{10}$-P internal standard can be readily avoided by adjusting the ESI-MS conditions by addition of $Na^+$ ions to generate the gas phase ions as Na-adducts.

All three of the targeted enzymes can be analyzed simultaneously in a single biological sample, such as a cell lysate. The PMM2 and PMIb cannot be assayed simultaneously because they require the addition of different exogeneous substrates. Nevertheless, two assays using identical ESI-MS techniques can be used for diagnosing the various CDGS types instead of relying on a battery of different methods.

Clinical Enzymology Assays

A fibroblast cell pellet is thawed on ice. Sufficient 0.9% NaCl is added to give a final protein concentration in the lysate of ~5 mg/mL (typically 100 mcL), and the cell pellet is sonicated in ice water 5 times for 2 seconds each at moderate power. Total protein is determined spectrophotmetrically using the BCA reagent (BCA Protein Assay kit, Pierce).

The total enzyme reaction volume is 20 û 30 mcL. The substrate stock solutions are maintained at concentrations of 3 mM (SFB) and 2 mM (GM1). These concentrations were measured by 1H-NMR signal integration versus an internal standard (formamide proton of DMF). Final concentration of substrates is 0.3 and 0.2 mM, respectively. A volume of reaction buffer (e.g. 200 mM sodium citrate, pH 4.5) equal to the difference of the substrate addition (2–3 mcL) plus sufficient cell sample volume to equal 50 û 75 mcg total protein from 20–30 mcL is added to a 0.5 mL Eppendorf tube, followed by substrate. The sample is cooled on ice, and patient cell sample is added. The reaction is initiated by incubation at 37 deg C.

For SFB: The reaction is allowed to proceed for 4.5 N 6 hours, after which GM1 substrate can be added or the reaction can be quenched with 100 mcL of 200 mM glycine-carbonate buffer, pH 10.5.

For GM1: The reaction is allowed to proceed for 0.5 hours. Quenching is as for SFB.

After quenching, the samples are placed on ice. Internal standards are added (1 nmol each, i.e. 50 mcL of a 0.02 mM solution). The samples are microfuged at ~15,000 rpm for 2 min at room temperature to pellet cell debris. Streptavidin-Agarose beads (Immunopure immobilized streptavidin, Pierce) are placed in a micro bio-spin chromatography column (Bio-Rad). Sufficient beads are added to give a total biotin binding capacity of 5 nmol (typical binding capacity 100 pmol per mcL of beads as determined by Pierce). The sample supernatant is transferred to the bio-spin tube and allowed to bind for 10 minutes at room temperature. The sample is spun at ~3,000 rpm to remove excess supernatant, then washed once with 0.01% Triton X-100 and at least five times with purified water, spinning the tube in-between to remove solution. For each wash, sufficient wash solution is added to fill the bio-spin tube.

The purified beads are then treated with 30 mcL purified water, followed by 10 mcL of a 4 mM biotin solution. The tubes are capped at the bottom to prevent leakage and allowed to incubate at 2–8° C. for 2–12 hours. The samples are spun at ~3,000 rpm to elute the sample into a clean Eppendorf tube.

The sample is then diluted with 60 mcL of 50% methanol/water and infused into the ion-trap mass spectrometer. The ESI-MS spectrum is tuned to reduce non-specific cleavage of the samples by first analyzing a blank sample (cell lysate added after reaction quench). The infused sample is analyzed by ion chromatogram integration of a 1 amu-wide window about the $(M+H+)^+$ ions of product and internal standard.

Results are reported in nmol product formed/hour of incubation/milligrams total protein in reaction mixtures Clinical Analysis of Patient Samples for GM1 and SFB Patient skin fibroblasts were obtained as frozen pellets, and stored at N20 deg C. until use. Two GM1 affected samples and six normal controls were analyzed.

50 mcL of 0.9% NaCl was added to each patient cell pellet. The pellets were lysed by sonication in ice water 5× for 2 seconds each at moderate sonication power, chilling the microtip in ice water in between sonications.

Samples were quantitated by BCA (Pierce) assay as follows:

Reagent A and B were mixed in 50:1 ratio as described. A protein standard curve was prepared using bovine serum albumin as a standard at concentrations of 2, 1, 0.5, 0.2, and 0.05 mg/mL. A portion of the patient sonicates were diluted 1:15 in water, and 5 mcL of each diluted patient sample and standard curve point was added to separate glass culture tubes containing 200 mcL water, in duplicate. The samples were then diluted with 1 mL of the mixed BCA reagent, vortexed to mix, and incubated at 37 deg C. for 60 minutes. The samples were allowed to cool to room temperature, and analyzed against a blank containing only 200 mcL water. The samples were analyzed by monitoring absorbance at 562 nm in polystyrene cuvettes. Average patient absorbance values were blank corrected and compared to standards via linear regression.

The patient protein concentrations were determined to be:
1. (Affected) 12.2 mg/mL, 2. (Normal) 10.8 mg/mL, 3. (Normal) 11.9 mg/mL, 4. (Normal) 12.1 mg/mL, 5. (Normal) 10.3 mg/mL, 6. (Normal) 7.79 mg/mL, 7. (Normal) 15.7 mg/mL, 8. (Affected) 11.4 mg/mL Incubations were performed in a total of 30 mcL of total volume. The amount of reaction buffer (200 mM sodium citrate, pH 4.25) added to blank Eppendorf tubes was the difference of the substrate volume (3 mcL of each substrate stock solution, 2 mM for GM1 and 3 mM for SFB, for a total of 6 mcL) plus the volume of cell lysate required to equal 75 mcg total protein, from 30 mcL. For example, patient 1. incubation mixture initially contained 3 mcL of SFB substrate solution, 6.14 mcL patient cell lysate, and 17.86 mcL reaction buffer. The GM1 substrate was added later in the incubation (see below).

Each patient sample was analyzed in triplicate. The reaction mixtures were kept on ice during preparation, and the reaction was initiated by transfer to a 37 deg C. water bath. 5.5 hours into the incubation, 3 mcL GM1 substrate was added to each reaction, and after an additional 0.5 hours the reactions were placed on ice and quenched with 200 mcL The purification and analysis procedures are as described in Clinical Enzymology Assay (Typical).

The resultant enzyme activities, as an average standard deviation nmol product/hour incubation/mg total protein:

|  | B-Gal | | SFB | |
| --- | --- | --- | --- | --- |
|  | RATE | +/− SD | Rate | +/− SD |
| Normals |  |  |  |  |
| Patient 2 | 68.0 | 2.6 | 0.90 | 0.05 |
| Patient 3 | 35.5 | 3.9 | 1.54 | 0.38 |
| Patient 4 | 51.1 | 2.7 | 1.36 | 0.26 |
| Patient 5 | 38.8 | 8.3 | 1.01 | 0.12 |
| Patient 6 | 51.4 | 9.9 | 2.25 | 0.36 |
| Patient 7 | 40.9 | 3.7 | 1.12 | 0.20 |
| Affecteds |  |  |  |  |
| $GM_1$ (#1) | 0.9 | 0.9 | 0.80 | 0.21 |
| $GM_1$ (#8) | 0.8 | 0.6 | 0.70 | 0.20 |

The following synthetic method refer to Schemes 14–23

Synthesis for GM1-gangliosidosis (beta-D-galactosidase deficiency)

1. 2,3,5,6-Tetrafluorophenyl trifluoroacetate (1)

25 g (0.15 mol) 2,3,5,6-tetrafluorophenol, 35 mL (0.2 mol) trifluoroacetic anhydride and 0.5 mL boron trifluoride etherate were refluxed for 18 hours under argon atmosphere. Trifluoroacetic anhydride and trifluoroacetic acid were removed by distillation at room temperature. The trifluoroacetic anhydride fraction was returned to the mixture, and the reaction was refluxed for 24 hours. This was repeated twice. After final distillation at room temperature, the desired product 1 was distilled at reduced pressure (62° C./45 mmHg) to produce a colorless liquid (30 g, 82%). 1H-NMR. (Ref. Gamper, H. B., Nucl. Acids Res., v21 pp145–150)

2. Biotin-2,3,5,6-tetrafluorophenyl ester (2)

A 2.5 g (10.3 mmol) quantity of d-biotin in 20 mL anhydrous DMF under argon atmosphere was warmed to 60° C. with stirring to effect dissolution. 1.7 mL (12.5 mmol) triethylamine was added, followed by 3.4 g (12.5 mmol) 1. The mixture was stirred for 2 hours, after which the solvent was removed by rotary evaporation. The resultant semi-solid was triturated with 15 mL ether twice to produce a white solid (2.6 g, 65%). 1H-NMR. (Ref. Wilbur, D. S., Bioconj. Chem., v8 pp572–584)

3. N-methylglycylbiotinamide-methyl ester (3)

A 2.5 g (6.4 mmol) quantity of biotin tetrafluorophenyl ester in 30 mL anhydrous DMF under argon atmosphere was added to a mixture of 1.1 g (7.7 mmol) N-methylglycine methyl ester hydrochloride dissolved in 10 mL anhydrous DMF and 1.25 mL (9.0 mmol) triethylamine. The reaction mixture was stirred at room temperature for 2 hours, then the solvent was removed by rotary evaporation. The residue was extracted with choroform (2×100 mL), washed with water (2×20 mL), and dried with anhydrous sodium sulfate. The solvent was removed under vacuum to yield 2.1 g (98%) of methyl ester of N-methylglycine biotinamide as an oil. 1H-NMR. (Ref. Wilbur, D. S., Bioconj. Chem., v8 pp572–584)

4. N-methylglycylbiotinamide acid (4)

N-Methylglycylbiotinamide methyl ester was hydrolyzed in a mixture of 31 mL MeOH and 10 mL of 1N NaOH at room temperature with stirring for 1 hour. The mixture was diluted with 50 mL 50% MeOH/water and neutralized with cation exchange resin, hydrogen form (AG MP-50, BioRad). The solution was filtered, the resin washed (3×50 mL) with 50% MeOH/water, and the solvents removed by rotary evaporation to yield 1.6 g (90%) of N-methylglycylbiotinamide acid as an off-white solid. 1H-NMR. (Ref. Wilbur, D. S., Bioconj. Chem., v8 pp572–584)

5. p-Acrylamidophenyl-B-D-galactopyranoside (5)

40 mg (0.15 mmol) p-aminophenyl o-D-galactopyranoside was added to 25 mL methanol and 200 mcL triethylamine with stirring. The solution was chilled in an ice bath. 53.3 mg (0.6 mmol) acryloyl chloride was dissolved in 5 mL dry methylene chloride and added dropwise to the stirred solution over 5 minutes. The reaction was allowed to return to room temperature, followed by 2 hours of stirring. The solution was then treated with successive anion and cation exchange resins (AG MP-1 and AG MP-50, respectively, BioRad) until neutral pH was obtained with moist pH paper. Solvent was removed by rotary evaporation to yield a solid (43 mg, 90%). 1H-NMR. (Ref. Romanowska, A., Methods Enzymol., v242 pp90–101)

6. Michael Addition Product of 4,7,10-trioxa-1,13-tridecanediamine and 5 (6)

20 mg (0.07 mmol) 5 was added to a stirred solution of 80 mg (0.35 mmol) 4,7,10-trioxa-1,13-tridecanediamine in 5 mL 0.2M sodium carbonate, pH 10.5 at 37° C. The reaction was allowed to proceed for 3 days, after which the solution was neutralized with dilute trifluoroacetic acid and purified by reverse-phase HPLC (Vydac C-18 prep-scale column, 6 mL/min. Mobile phase: $H_2O$ (0.08% TFA)/ACN (0.08% TFA)) to give 7.3 mg of product. (Ref. Romanowska, A., Methods Enzymol., v242 pp90–101)

7. GM1 Substrate Conjugate of 4 and 6 (7)

A 2.5 mg (7.4 mcmol) quantity of 4 was dissolved in 1.5 mL anhydrous DMF with stirring, under argon atmosphere. 5 mcL triethylamine was added, followed by 2.3 mg (8.8 mcmol) 1. The formation of active ester was monitored by silica TLC (5:1 CHCl3/CH3OH, Rf 0.5, UV) by briefly drying the spotted TLC plate with a stream of air. After 25 minutes, the mixture was added to 3.2 mg (5.9 mcmol) 6 in 1 mL anhydrous DMF. After 2 hours, the solvent was removed by vacuum centrifugation and the final product was purified by reverse-phase HPLC (Vydac C-18 prep-scale column, 6 mL/min. Mobile phase: H2O (0.08% TFA)/ACN (0.08% TFA)). Yield 4.6 mg. (Analogous chemistry, ref. Wilbur, D. S., Bioconj. Chem., v8 pp572–584)

8. 1,2,10,11-octadeutero-3,6,9-trioxa-1,11-undecanedinitrile (8)

1 g (9.4 mmol) of diethylene glycol was dissolved in 2 mL $D_2O$ in a 10 mL round bottom flask under argon atmosphere. The $D_2O$ was removed by rotary evaporation and the process was repeated 4 times. The d-2 diethylene glycol was additioned with 25 mL dry benzene, followed by 1.6 g (28.2 mmol) d-3 acrylonitrile with stirring under argon atmosphere. After 12 h, the solvent was removed under reduced pressure and the resultant semisolid was extracted with chloroform (2×5 mL). The solvent was removed by rotary evaporation to yield 1.85 g (89%) product. (Ref. Ashikaga, K., Bull. Chem. Soc. Jpn., v61 pp2443–2450)

9. 2,3,11,12-octadeutero-4,7,10-trioxa-1,13-tridecanediamine (9)

Raney nickel (Aldrich) was washed five times with anhydrous methanol by inversion and decantation. 50 mg of the washed catalyst was placed in 20 mL anhydrous methanol, followed by 1 g (4.6 mmol) 8 in a 50 mL screw-cap vial fitted with a Teflon-lined rubber septum. The vial headspace was flushed for a few min with H2 gas via an 18-gauge needle piercing the septum. The cap was screwed on tightly and the entire assembly was charged to 40 psi H2 and placed in a hot water bath (80° C.) for 4 hours, after which the solid catalyst was removed by filtration and the methanol evaporated. The final product was purified by reverse-phase HPLC (Vydac C-18 prep-scale column, 6 mL/min. Mobile phase: H20 (0.08% TFA)/ACN (0.08% TFA)). Yield 180 mg. (Ref. Ashikaga, K., Bull. Chem. Soc. Jpn., v61 pp2443–2450)

10. Deuterated analog of 6 (10)

25 mg (0.09 mmol) 5 was added to a stirred solution of 90 mg (0.4 mmol) 9 in 5 mL 0.2M sodium carbonate, pH 10.5 at 37?C. The reaction was allowed to proceed for 3 days, after which the solution was neutralized with dilute trifluoroacetic acid and purified by reverse-phase HPLC (Vydac C-18 prep-scale column, 6 mL/min. Mobile phase: H2O (0.08% TFA)/ACN (0.08% TFA)). Yield 6 mg.

11. Deuterated analog of 7 (11)

A 3 mg (8.4 mcmol) quantity of 4 was dissolved in 0.7 mL anhydrous DMF with stirring, under argon atmosphere. 5 mcL triethylamine was added, followed by 2.4 mg (8.9 mcmol) 1. The formation of active ester was monitored by silica TLC (5:1 $CHCl_3/CH_3OH$, Rf 0.5, UV) by briefly drying the spotted TLC plate with a stream of air. After 25 minutes, the mixture was added to 6 mg (11 mcmol) 10 in 1 mL anhydrous DMF. After 2 hours, the solvent was removed by vacuum centrifugation and the final product was purified by reverse-phase HPLC (Vydac C-18 prep-scale column, 6 mL/min. Mobile phase: H2O (0.08% TFA)/ACN (0.08% TFA)). Yield 1.8 mg.

12. GM1 Internal Standard Conjugate (12)

1.8 mg 11 was added to 2 mL 100 mM Tris/10 mM MgCl2, pH 7.3 buffer with stirring. 15 units recombinant B-D-galactosidase (Sigma) was added, and after 12 hours the mixure was purified by reverse-phase HPLC (Vydac C-18 prep-scale column, 6 mL/min. Mobile phase: H2O (0.08% TFA)/ACN (0.08% TFA)). Yield 1.5 mg.

Polyether diamine linker synthesis (Second Generation)

Synthesis is based on chemistry previously described (Kataky, R. et. al. J CHEM SOC PERK T 2 (2) 321–327 FEB 1990), with minor modifications and an additional two steps. As an example, deviations from the established procedure as well as exact details for the additional steps are outlined below for the starting material diethylene glycol.

1,11-Dicyano-3,6,9-trioxaundecane (13)

To a stirred solution of 2% (w/v) sodium hydroxide (5 mL) and diethylene glycol (5.3 g, 50 mmol) was added acrylonitrile (7.95 g, 150 mmol). The mixture was stirred at room temperature overnight and additioned with 50 mL dichloromethane. The organic layer was washed 2× with brine and dried (MgSO4). The solvent was removed by rotary evaporation. The oily residue was treated with 200 proof ethanol, and the solvent was removed by rotary evaporation. This was repeated 2× to remove excess unreacted acrylonitrile. The product was used without further purification

Diethyl 4,7,10-trioxatridecane-1,13-dioate (14)

2 g (9.4 mmol) 13, was dissolved in 5 mL ethanol. 1 g conc. sulfuric acid was added slowly, over 5 minutes. The reaction was heated to reflux overnight. The reaction was extracted with 40 mL methylene chloride, washed once with 10 mL water and 3× with 10 mL dilute brine solution. The organic layer was dried ($MgSO_4$) and solvent was removed to yield an oil. The final product was purified by silica chromatography (methylene chloride/ethyl acetate).

1,13-dihydroxy-4,7,10-trioxatridecane (15)

Prepared exactly as described, using tetrahydrofuran as solvent. (1.7 g, 5.5 mmol 14, 50 mL distilled [$CaH_2$] THF, 0.66 g, 16.5 mmol lithium aluminum hydride). Once addition was complete, excess LAH was quenched with ethanol, and the salts precipitated by dropwise addition of saturated sodium sulfate solution until a white precipitate formed. The solvent was removed, the precipitate washed 6×30 mL with THF and the combined organic extracts were evaporated to yield an oil. Final product is purified by silica chromatography (first with methylene chloride then with ethyl acetate and finally with acetone).

1,13-dichloro-4,7,10-trioxatridecane (analog using P2) (16)

1.1 g, (4.9 mmol) 15 was added to 1.15 g (14.6 mmol) distilled pyridine in 30 mL dry benzene with stirring, followed by 1.8 g (14.6 mmol) thionyl chloride. The mixture was heated to reflux for 6 hours. After cooling in an ice bath, 5 mL 3M HCl was added with vigorous stirring. The organic layer was separated, washed 3× with a dilute brine solution, and dried (MgSO$_4$) to yield a yellowish oil. After washing and removal of solvent, the dichloride was used without further purification.

Additional steps

1,13-dicyano-4,7,10-trioxatridecane) (17)

To a stirred solution of 0.78 g (15.5 mmol) sodium cyanide in 4 mL dimethyl sulfoxide at 80° C. was added 1 g (3.9 mmol) of 16. After 2 hours, the reaction was additioned with 10 mL of saturated sodium chloride solution, 5 mL of water, and 50 mL ethyl acetate. The organic layer was washed 3× with a brine solution as before, after which the organic layer was dried (Na2SO4) and the solvents removed. The final product was purified by silica chromatography (methlyene chloride/ethyl acetate). ESI-MS: predicted, 240.1; observed, 241.1 (M+H+)$^+$

1,15-diamino-5,8,11-trioxapentadecane (18)

A stirred solution of 50 mL dry THF containing 0.42 g (10.4 mmol) fresh LAH was heated to gentle reflux under argon for 15 minutes. 0.5 g (2 mmol) 17 in 15 mL dry THF was added dropwise over 20 minutes, maintaining a gentle reflux. The unreacted LAH was quenched with ethanol, and the mixture was treated with dropwise addition of saturated sodium sulfate under efficient stirring until a white precipitate formed. The mixture was filtered, and the precipitate was washed 6×30 mL with THF. The organic extracts were combined and the solvent was removed by rotary evaporation to yield an oil. ESI-MS: predicted, 248.1; observed, 249.1 (M+H+)$^+$ Deuteration Deuterium has been incorporated into the diamine linker by reduction of 14 and 17 using lithium aluminum deuteride (98% D) to achieve a d-8 deuterated diamine. No other aspects of the synthesis were changed for this procedure. These diols are used in the construction of the SFD conjugates as described later.

Clinical Substrate Synthesis for Sanfilippo Syndrome, type B (N-B-D-glucosaminidase deficiency)

13. p-Aminophenyl-beta-D-N-acetylglucosamine (19)

20 mg (0.07 mmol) p-Nitrophenyl-?-D-N-acetylglucosamine (Sigma) was added to 5 mg washed palladium catalyst on activated carbon in 3 mL methanol with stirring in a 5 mL septa-lined vial. The septum was pierced by a 16-gauge needle and the vial headspace was flused with H2 gas. H2 gas was allowed to slowly bubble through the solution for 2 hours, after which the catalyst was removed by filtration over diatomaceous earth (Celite). The solvent was removed by rotary evaporation to yield a semi-solid 18 mg (90%).

14. p-Acrylamidophenyl-?-D-N-acetylglucosamine (20)

10 mg (0.03 mmol) 19 was added to 15 mL methanol and 100 mcL triethylamine with stirring. The solution was chilled in an ice bath. 15 mg (0.17 mmol) acryloyl chloride was dissolved in 2 mL dry methylene chloride and added dropwise to the stirred solution over 5 minutes. The reaction was allowed to return to room temperature, followed by 2 hours of stirring. The solution was then treated with successive anion and cation exchange resins (AG MP-1 and AG MP-50, respectively, BioRad) until neutral pH was obtained with moist pH paper. Solvent was removed by rotary evaporation to yield a solid (11 mg, 95%). 1H-NMR. Yield 11 mg.

15. 3,6-dioxa-1,9-nonanedinitrile (21)

2 g (0.032 mol) ethylene glycol was added to 0.5 g dry potassium hydroxide in 30 mL dry benzene, followed by 5 g (0.096 mmol) acrylonitrile with stirring overnight at room temperature. The reaction was filtered and the solvent was removed by rotary evaporation to yield an oil. Final product was purified by silica chromatography (chloroform/methanol) to yield a colorless oil 3.2 g (60%).

16. 4,7-dioxa-1,10-decanediamine (22)

Raney nickel (Aldrich) was washed five times with anhydrous methanol by inversion and decantation. 50 mg of the washed catalyst was placed in 20 mL anhydrous methanol, followed by 1 g (6 mmol) 21 in a 50 mL screw-cap vial fitted with a Teflon-lined rubber septum. The vial headspace was evacuated with H2 gas via an 16-gauge needle piercing the septum. The cap was screwed on tightly and the entire assembly was charged to 40 psi H2 and placed in a hot water bath (80 C.) for 4 hours, after which the solid catalyst was removed by filtration and the methanol evaporated. The final product was purified by reverse-phase HPLC (Vydac C-18 prep-scale column, 6 mL/min. Mobile phase: H2O (0.08% TFA)/ACN (0.08% TFA)).

17. Michael Addition Product of 20 and 22 (23)

5 mg (0.015 mmol) 20 was added to a stirred solution of 13 mg (0.06 mmol) 22 in 5 mL 0.2M sodium carbonate, pH 10.5 at 37?C. The reaction was allowed to proceed for 3 days, after which the solution was neutralized with dilute trifluoroacetic acid and purified by reverse-phase HPLC (Vydac C-18 prep-scale column, 6 mL/min. Mobile phase: H2O (0.08% TFA)/ACN (0.08% TFA)). Yield 6 mg.

18. SFB Substrate Conjugate of 4 and 23 (24)

A 4 mg (0.013 mmol) quantity of 4 was dissolved in 1.5 mL anhydrous DMF with stirring, under argon atmosphere. 10 mcL dry triethylamine was added, followed by 4 mg (0.015 mmol) 1. The formation of active ester was monitored by silica TLC (5:1 CHCl3/CH3OH, Rf 0.5, UV) by briefly drying the spotted TLC plate with a stream of air. After 25 minutes, the mixture was added to 6 mg (0.012 mmol) 23 in 1 mL anhydrous DMF. After 2 hours, the solvent was removed by vacuum centrifugation and the final product was purified by reverse-phase HPLC (Vydac C-18 prep-scale column, 6 mL/min. Mobile phase: H2O (0.08% TFA)/ACN (0.08% TFA)). Yield 4.2 mg.

19. 1,9-tetradeutero-3,6-dioxa-1,9-nonanedinitrile (25)

0.5 g (8 mmol) ethylene glycol was added to 0.1 g dry potassium hydroxide in 20 mL acetonitrile, followed by 1.4 g (24 mmol) d-3 acrylonitrile with stirring overnight at room temperature. The reaction was filtered and the solvent was removed by rotary evaporation to yield an oil. Final product was purified by silica chromatography (chloroform/methanol) to yield a colorless oil 0.9 g (65%).

20. 1,9-tetradeutero-3,6-dioxa-1,9-nonanediamine (26)

Raney nickel (Aldrich) was washed five times with anhydrous methanol by inversion and decantation. 20 mg of the washed catalyst was placed in 30 mL anhydrous methanol, followed by 0.5 g (3 mmol) 25 in a 50 mL screw-cap vial fitted with a Teflon-lined rubber septum. The vial headspace was evacuated with H2 gas via an 18-gauge needle piercing the septum. The cap was screwed on tightly and the entire assembly was charged to 40 psi H2 and placed in a hot water bath (80 C.) for 4 hours, after which the solid catalyst was removed by filtration and the methanol evaporated. The final product was purified by reverse-phase HPLC (Vydac C-18 prep-scale column, 6 mL/min. Mobile phase: H2O (0.08% TFA)/ACN (0.08% TFA)).

21. Deuterated Analog of 23 (27)

20 mg (0.07 mmol) p-acrylamidophenyl ?-D-galactoside was added to a stirred solution of 90 mg (0.4 mmol) 26 in 5 mL 0.2M sodium carbonate, pH 10.5 at 37?C. The reaction was allowed to proceed for 3 days, after which the solution was neutralized with dilute trifluoroacetic acid and purified by reverse-phase HPLC (Vydac C-18 prep-scale column, 6 mL/min. Mobile phase: H2O (0.08% TFA)/ACN (0.08% TFA)). Yield 2 mg.

22. Deuterated Analog of 24 (28)

A 2 mg (6.3 mcmol) quantity of 4 was dissolved in 1.5 mL anhydrous DMF with stirring, under argon atmosphere. 5 mcL triethylamine was added, followed by 2.1 mg (7.6 mcmol) 1. The formation of active ester was monitored by silica TLC (5:1 CHCl3/CH3OH, Rf 0.5, UV) by briefly drying the spotted TLC plate with a stream of air. After 35 minutes, the mixture was added to 4 mg (7 mcmol) 27 in 1 mL anhydrous DMF. After 2 hours, the solvent was removed by vacuum centrifugation and the final product was purified by reverse-phase HPLC (Vydac C-18 prep-scale column, 6 mL/min. Mobile phase: H2O (0.08% TFA)/ACN (0.08% TFA)). Yield 1.2 mg.

23. SFB Internal Standard Conjugate (29)

1.2 mg 28 was added to 2 mL 100 mM Tris/10 mM MgCl2, pH 7.3 buffer with stirring. 15 units recombinant ?-D-galactosidase (Sigma) was added, and after 12 hours the mixture was purified by reverse-phase HPLC (Vydac C-18 prep-scale column, 6 mL/min. Mobile phase: H2O (0.08% TFA)/ACN (0.08% TFA)). Yield 0.7 mg.

Clinical Substrate Synthesis for Sanfilippo Syndrome, type D (a sulfatase deficiency)

24. p-Acrylamidophenyl-?-D-N-acetylglucosamine-6-sulfate (30)

100 mg (0.28 mmol) 20 was added to 10 mL dry DMF under argon atmosphere with stirring at room temperature. 89 mg (0.56 mmol) sulfur trioxide-pyridine complex was dissolved in 2 mL dry DMF and was added to the reaction in 0.7×, 1.1×, 1.3× and 1.9× equivalents (+700 mcL, +400 mcL, +200 mcL, and +600 mcL). The reaction progress was monitored by 1H-NMR shift of the anomeric (C1) proton chemical shift from 5.29 to 5.24 ppm by removal of 15 mcL of solution 1 hour after addition of each amount of sulfating reagent. The removed mixture was dried by vacuum centrifugation and redissolved in d-6 DMSO and analyzed. Upon the appearance of more than two forms (starting material and C-6 sulfate) of the C1 anomeric proton, the reaction was removed to−20?C. and stored. The product was purified by vacuum centrifugation to remove solvent, followed by reverse-phase HPLC (Vydac C-18 prep-scale column, 6 mL/min. Mobile phase: H2O (0.08% TFA)/ACN (0.08% TFA)). Yield 72%.

25. Michael Addition Product of 18 and 30 (31)

25 mg (0.058 mmol)30 was added to a stirred solution of 83 mg (0.35 mmol) 18 in 5 mL 0.2M sodium carbonate, pH 10.5 at 37?C. The reaction was allowed to proceed for 3 days, after which the solution was neutralized with dilute trifluoroacetic acid and purified by reverse-phase HPLC (Vydac C-18 prep-scale column, 6 mL/min. Mobile phase: H2O (0.08% TFA)/ACN (0.08% TFA)). Yield 10 mg.

26. SFD Substrate Conjugate of 4 and 31 (32)

A 5.7 mg (0.018 mmol) quantity of 4 was dissolved in 1.0 mL anhydrous DMF with stirring, under argon atmosphere. 20 mcL dry triethylamine was added, followed by 5.5 mg (0.020 mmol) 1. The formation of active ester was monitored by silica TLC (5:1 CHCl3/CH3OH, Rf 0.5, UV) by briefly drying the spotted TLC plate with a stream of air. After 25 minutes, the mixture was added to 10 mg (0.015 mmol) 31 in 1 mL anhydrous DMF. After 2 hours, the solvent was removed by vacuum centrifugation and the final product was purified by reverse-phase HPLC (Vydac C-18 prep-scale column, 6 mL/min. Mobile phase: H2O (0.08% TFA)/ACN (0.08% TFA)). Yield 5.4 mg.

27. 1,2,14,15-octadeutero-1,15-diamino-5,8,11-trioxapentadecane (33)

As referenced in ôPolyether Diamine Linker Synthesis, Second Generation

28. Deuterated Analog of 31 (34)

25 mg (0.07 mmol) 20 was added to a stirred solution of 100 mg (0.4 mmol) 11 in 5 mL 0.2M sodium carbonate, pH 10.5 at 37?C. The reaction was allowed to proceed for 3 days, after which the solution was neutralized with dilute trifluoroacetic acid and purified by reverse-phase HPLC (Vydac C-18 prep-scale column, 6 mL/min. Mobile phase: H2O (0.08% TFA)/ACN (0.08% TFA)). Yield 7 mg.

29. SFD Internal Standard Conjugate (35)

A 4 mg (12.6 mcmol) quantity of 4 was dissolved in 1 mL anhydrous DMF with stirring, under argon atmosphere. 20 mcL triethylamine was added, followed by 4 mg (14 mcmol) 1. The formation of active ester was monitored by silica TLC (5:1 CHCl3/CH3OH, Rf 0.5, UV) by briefly drying the spotted TLC plate with a stream of air. After 20 minutes, the mixture was added to 7 mg (11 mcmol) 34 in 1 mL anhydrous DMF. After 4 hours, the solvent was removed by vacuum centrifugation and the final product was purified by reverse-phase HPLC (Vydac C-18 prep-scale column, 6 mL/min. Mobile phase: H2O (0.08% TFA)/ACN (0.08% TFA)). Yield 2.7 mg.

N-(d-Biotinyl-sarcosinyl)-12-aminododecanoic acid (36)

Compound 4 (32.2 mg, 0.102 mmole) was dried overnight in vacuo (with P2O5). Dry DMF (2 mL) was added and the mixture was stirred with warming to affect dissolution under nitrogen. Triethylamine (34 mcL) was added followed by 1 (20.4 mcL, 0.115 mmole) added in two 10.2 mcL portions, 5 min apart. The mixture was stirred for 1 hr at room temperature under nitrogen. 12-Aminododecanic acid (24.1 mg, 0.112 mmole, Sigma) was added in one portion, and the mixture was stirred at room temperature for 2 hr under nitrogen. CHCl3 (80 mL) was added, and the organic solution was washed with two 10 mL portions of 1 M HCl.

CHCl3 was removed by rotary evaporation, and residual DMF was removed by vacuum centrifugation. The compound was dissolved in methanol and purified by HPLC (Vydac 218TP prep column). Solvent program is: 0–10 min, water with 0.06% TFA; 10–55 min, 0–100% methanol with 0.06% TFA, flow rate is 6 mL/min. Yield 31.7 mg. 1H-NMR. ESI-MS, calculated 513.4, observed 513.4 (M+H)+

N-hydroxysuccinimidyl ester of 36 (37)

Compound 36 (9.8 mg, 19 mcmole) is dissolved in 100 mcL of dry DMF under nitrogen. N-hydroxysuccinimide (2.2 mg, 19 mcmole) was added followed by dicyclohexylcarbodiimide (3.9 mg, 19 mcmole). The mixture was stirred at room temperature for 60 h in the dark. Solvent was removed by vacuum centrifugation, and the residue was submitted to flash chromatography on silica gel using a gradient of CHCl3/CH3OH (15/1) to CHCl3/CH3OH (12/1). Yield 9.8 mg. 1H-NMR. ESI-MS, calculated 610.8, observed 609.7 (M+H)+

N-(N-(d-Biotinyl-sarcosinyl)-12-aminododecanoyl)-pyschosine (38)

Compound 37 (6.2 mg, 10 mcmole) and pyschosine (4.7 mg, 10 mcmole, Sigma) were dissolved in 200 mcL of dry DMF under nitrogen. Diisoproylethylamine (5 mcL) was added, and the mixture was stirred under nitrogen for 2 days in the dark. The compound was injected directly onto the HPLC column (Vydac 218TP semi-prep), and the column was developed at 2 mL/min with 0–20 min, water with 0.06% TFA, then 20–80 min, 0–100% methanol with 0.06% TFA. Yield 3.8 mg. 1H-NMR. ESI-MS, calculated 957.3, observed 956.8 (M+H)+

N-(N-(d-Biotinyl-sarcosinyl)-12-aminododecanoyl)-sphingosylphosphorylcholine (39)

Sphingosylphosphorylcholine (4.0 mg, Sigma) was mixed with 1 mL dry DMF and solvent was removed by vacuum centrifugation. This was repeated two more times. The final dried residue weighed 2.5 mg (5.4 mcmole). To this residue was added 3.3 mg of 37 (5.4 mcmole), 150 mcL of dry DMF, and 2.5 mcL of diisoproylethylamine. The mixture was stirred under nitrogen in the dark for 3 days. The compound was injected directly onto the HPLC column (Vydac 218TP semi-prep), and the column was developed at 2 mL/min with 0–20 min, water with 0.06% TFA, then 20–80 min, 0–100% methanol with 0.06% TFA. Yield 3.8 mg. 1H-NMR. ESI-MS, calculated 960.3, observed 958.7 (M+H)+

Conjugate of d-biotin with 1,13-diamino-4,7,10-trioxatridecane (40)

Compound 2 was reacted with 1,13-diamino-4,7,10-trioxatridecane (Fluka) essentially as described for the synthesis of 3. The product was purified by HPLC (Vydac 218TP, semi-prep) using 0–100% methanol with 0.06% TFA over 30 min at 1.5 mL/min.

Iodoacetylated 40 (41)

Compound 40 was treated with 5 equivalents of iodoacetic anhydride (Aldrich) in dry DMF with stirring under nitrogen for 4 h at room temperature. The product was purified on HPLC as for 40. The structure was confirmed by ESI-MS.

Octadeuterated 41 (42)

The title compound was prepared as for the 40 using 9 instead of 1,13-diamino-4,7,10-trioxatridecane.

Octadeuterated 42 (43)

The title compound was prepared from 42 as for 41. The structure was confirmed by ESI-MS.

Exemplary $MS^N$ Techniques and Instrumentation

Figure 7:
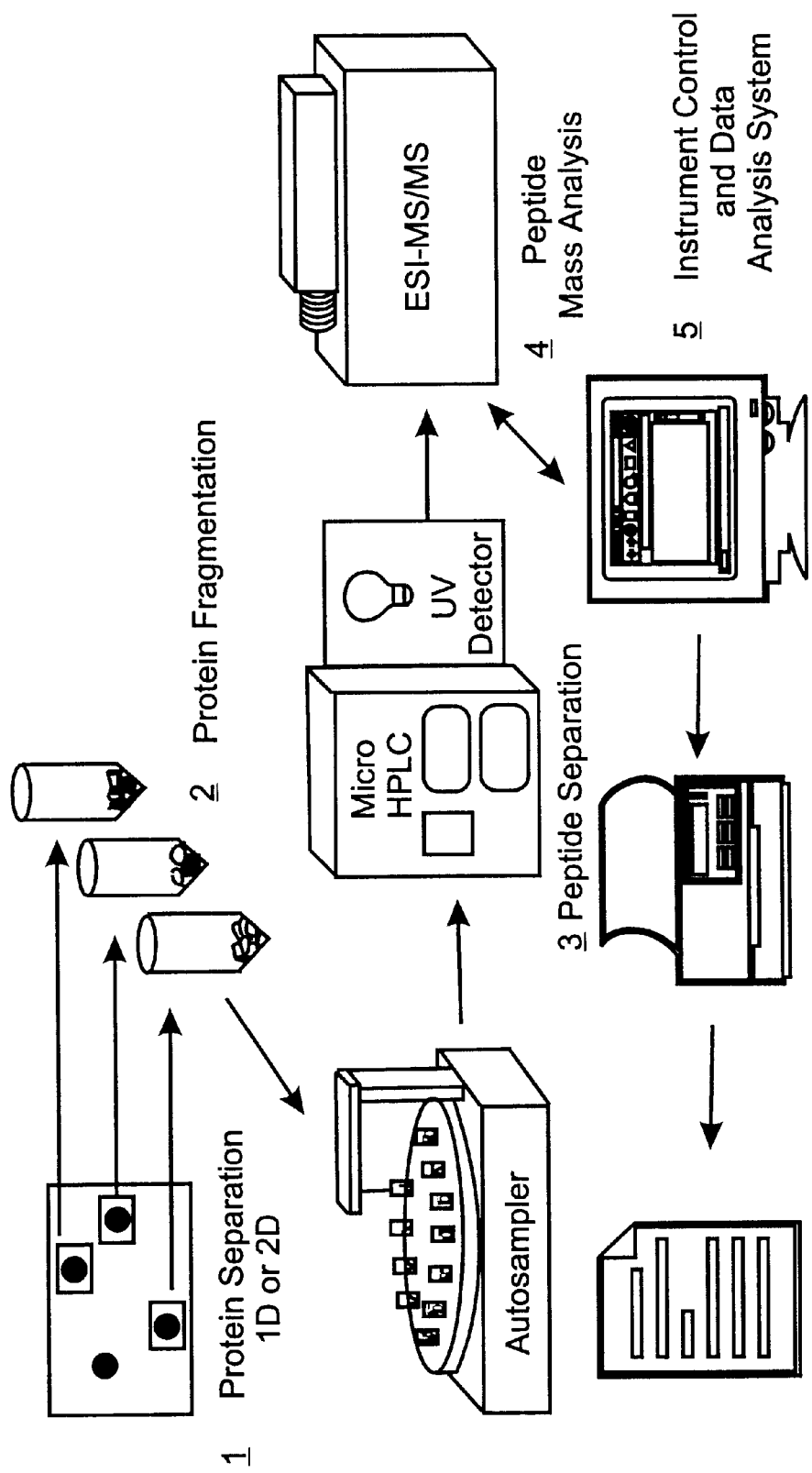
FIG. 7 is a schematic representation of the automated LC-MS/MS system.

An automated LC-MS/MS system for the identification of proteins by their amino acid sequence has been developed. A schematic representation is shown in FIG. 7 The system, which consists of an autosampler, a capillary HPLC system connected on-line to an ESI triple quadrupole MS/MS instrument and a data system is operated in the following way: Proteins (typically separated by 1D or 2D gel electrophoresis) are cleaved with a specific protease, usually trypsin. the resulting cleavage fragments are placed in an autosampler. Every 37 minutes the autosampler injects one sample into the HPLC system and the peptides are separated by capillary reverse-phase chromatography. As separated peptides elute from the chromatography column, they are ionized by the ESI process, enter the MS and the mass to charge ratio (m/z) is measured. Any peptide ion whose intensity exceeds a predetermined intensity threshold is automatically selected by the instrument and collided in the collision cell with inert gas. These collisions result in peptide fragmentation, primarily at the bonds of the peptide backbone (collision induced dissociation, CID). The masses of the CID fragments are measured and recorded in the data system. The CID spectrum of a peptide contains sufficient information to identify the protein by searching sequence databases with the uninterpreted MS/MS spectra. This is accomplished with the Sequent program. The program identifies each peptide in a sequence database which has the same mass as the peptide that was selected in the MS for CID and predicts the MS/MS spectrum for each one of the isobaric peptides. By matching the experimentally determined CID spectrum with computer generated theoretical CID spectra, the protein from which the observed peptide originated is identified. The system is capable of analyzing protein samples in a fully automated fashion at a pace of less than 40 min. per sample. Since each peptide represents an independent protein identification and usually multiple peptides are derived from one protein, protein identification by this method is redundant and tolerant to proteins co-migrating in a gel. The system is well suited for the detection and characterization of modified residues within polypeptide chains. The LC-MS/MS technique and automated analysis of the generated CID spectra can be used for the methods of this invention.

Identification of Proteins at Sub-femtomole Sensitivity by Solid-phase Extraction Capillary Electrophoresis Tandem Mass Spectrometry (SPE-CE-MS/MS)

Protein identification by this method is based on the same principle as described above, except that peptide separation and ionization are performed at significantly higher sensitivity. FIG. 8 shows a schematic representation of the key design elements. The design of the system and its mode of operation have been published. Peptides derived from protein digests are concentrated by SPE, separated by CE and analyzed by ESI-MS/MS. The resulting uninterpreted CID spectra are used to search sequence databases with the Sequest software system. The SPE extraction device is a small reversed-phase chromatography column of the dimensions 0.18×1 mm which is directly packed in a fused silica separation capillary. Peptides contained in a sample solution are adsorbed and concentrated on the SPE device, eluted in an estimated 100–300 nl of organic solvent and further concentrated by electrophoretic stacking and/or isotachophoresis to an estimated volume of 5–30 nl. The peptides are then separated by CE in a 20 $\mu$m or 50 $\mu$m i.d. capillary and directly ionized by ESI as they leave the capillary (see reference 13 for design of the microspray ionization source). With this system, peptide masses can be determined at a sensitivity of 660 attomoles (approx. 500 fg for a 20 residue peptide) at a concentration limit of 33 amol/µl and that proteins can be identified by the CID spectra of automatically selected peptides at less than 10 fmol (0.5 ng for a protein of 50 kDa) of sample at a concentration limit of less than 300 amol/µl. this technique is used for the analysis at very high sensitivity of the peptide samples generated by the experiments. It has also been demonstrated that the analysis time available for automated CID experiments can be significantly extended by data-dependent modulation of the CE voltage. If several peptide ions are detected coincidentally in the MS, the CE voltage is automatically dropped. This results in a reduction of the electroosmotic flow out of the capillary and therefore in an extension of the time period available for selecting peptide ions for CID. The net effect of this peak parking technique is an extension of the dynamic range of the technique because the increased time available is used for CID of ions with a low ion current. Once all the peptide ions are analyzed, electrophoresis is automatically reaccelerated by increasing the CE voltage to the original value.

TABLE 1

Relative, redundant quantitation of α-lactalbumin abundance (after mixing with known amount of the same protein with cysteines modified with isotopically heavy biotinylating reagent)

| Peptide # | m/z (light) | Charge state | Peptide Sequence | Ratio heavy: light |
|---|---|---|---|---|
| 1 | 518.4 | 2+ | (K) IWCK | 2.70 |
| 2 | 568.4 | 2+ | (K) ALCSEK (SEQ ID NO: 2) | 2.68 |
| 3 | 570.4 | 2+ | (K) CEVFR (SEQ ID NO: 3) | 2.90 |
| 4 | 760.5 | 2+ | (K) LDQWLCEK (SEQ ID NO: 4) | 2.82 |
| 5 | 710.1 | 3+ | (K) FLDDDLTDDIMCVK (SEQ ID NO: 5) | 2.88 |
| 6 | 954.2 | 3+ | (K) DDQNPHSSNICNISCDK (SEQ ID NO: 6) | 2.90 |
| 7 | 1286.9 | 4+ | (K) GYGGVSLPEWVCTTFHTSGYDT QAIVQNNDSTEYGLFQINNK (SEQ ID NO: 7) | NA[a] |

[a]Isotope ratio was not analyzed because on a 4 peptide the isotope patterns were highly overlapping due to differences of only 2 amu between heavy and light ions.

TABLE 2

Sequence identification and quantitation of the components of a protein mixture in a single analysis.

| Gene Name* | Peptide sequence identified | Observed ratio (d0/d8)[†] | Mean ± SD | Expected ratio (d0/d8)[⁻] | % error |
|---|---|---|---|---|---|
| LCA_BOVIN | ALC#SEK (SEQ ID NO: 8) | 0.94 | | | |
| | C#EVFR | 1.03 | 0.96 ± 0.06 | 1.00 | 4.2 |
| | FLDDLTDDIMC#VK (SEQ ID NO: 9) | 0.92 | | | |
| OVAL_CHICK | ADHPFLFC#IK (SEQ ID NO: 10) | 1.88 | | | |
| | YPILPEYLQC#VK (SEQ ID NO: 11) | 1.96 | 1.92 ± 0.06 | 2.00 | 4.0 |
| BGAL_ECOLI | LTAAC#FDR (SEQ ID NO: 12) | 1.00 | | | |
| | IGLNC#QLAQVAER (SEQ ID NO: 13) | 0.91 | 0.98 ± 0.07 | 1.00 | 2.0 |
| | IIFDGVNSAFHLWC#NGR (SEQ ID NO: 14) | 1.04 | | | |
| LACB_BOVIN | WENGEC#AQK (SEQ ID NO: 15) | 3.64 | | | |
| | LSFNPTQLEEQC#HI (SEQ ID NO: 16) | 3.45 | 3.55 ± 0.13 | 4.00 | 11.3 |
| G3P_RABIT | VPTPNVSVVDLTC#R (SEQ ID NO: 17) | 0.54 | | | |
| | IVSNASC#TTNC#LAPLAK (SEQ ID NO: 18) | 0.57 | 0.56 ± 0.02 | 0.50 | 12.0 |
| PHS2_RABIT | IC#GGWQMEEADDWLR (SEQ ID NO: 19) | 0.32 | | | |
| | TC#AYTNHTVLPEALER (SEQ ID NO: 20) | 0.35 | 0.32 ± 0.03 | 0.33 | 3.1 |
| | WLVLC#NPGLAEIIAER (SEQ ID NO: 21) | 0.30 | | | |

*Gene names are according to Swiss Prot nomenclature (www.expasy.ch).
[†]Ratios were calculated for each peptide as shown in FIG. 3.
[⁻]Expected ratios were calculated from the known amounts of proteins present in each mixture.
190 ICAT-labeled cysteinyl residue.

TABLE 3

Protein profiles from yeast growing on galactose or ethanol as a carbon source.

| Gene name* | Peptide sequence identified | Observed ratio[†] (Eth:Gal)[⁻] | Galactose-repressed[§] | Glucose-repressed[§] |
|---|---|---|---|---|
| ACH1 | KHNC#LHEPHMLK (SEQ ID NO: 22) | >100:1 | ✓ | |
| ADH1 | YSGVC#HTDLHAWHGDWPLPVK (SEQ ID NO: 23) | 0.57:1 | | |
| | C#C#SDVFNQVVK (SEQ ID NO: 24) | 0.48:1 | | |

TABLE 3-continued

Protein profiles from yeast growing on galactose or ethanol as a carbon source.

| Gene name* | Peptide sequence identified | Observed ratio† (Eth:Gal)⁻ | Galactose-repressed§ | Glucose-repressed§ |
|---|---|---|---|---|
| ADH2 | YSGVC#HTDLHAWHGDWPLPTK (SEQ ID NO: 25) | >200:1 | ✓ | ✓ |
|  | C#SSDVFNHWK (SEQ ID NO: 26) | >200:1 |  |  |
| ALD4 | TFEVINPSTEEEIC#HIYEGR (SEQ ID NO: 27) | >100:1 | ✓ | ✓ |
| BMH1 | SEHQVELIC#SYR (SEQ ID NO: 28) | 0.95:1 |  |  |
| CDC19 | YRPNC#PIILVTR (SEQ ID NO: 29) | 0.49:1 |  |  |
|  | NC#TPKPTSTTETVAASAVAAVFEQK3 (SEQ ID NO: 30) | 0.65:1 |  |  |
|  | AC#DDK | 0.67:1 |  |  |
| FBA1 | SIAPAYGIPVVLHSDHC#AK (SEQ ID NO: 31) | 0.60:1 |  |  |
|  | EQVGC#K (SEQ ID NO: 32) | 0.63:1 |  |  |
| GAL1 | LTGAGWGGC#TVHLVPGGPNGNIEK (SEQ ID NO: 33) | 1:>200 |  | ✓ |
| GAL10 | HHIPFYEVDLC#DR (SEQ ID NO: 34) | 1:>200 |  | ✓ |
|  | DC#VTLK (SEQ ID NO: 35) | 1:>200 |  |  |
| GCY1 | LWC#TQHHEPEVALDQSLK (SEQ ID NO: 36) | 0.34:1 |  | ✓ |
| GLK1 | IC#SVNLHGDHTFSMEQMK (SEQ ID NO: 37) | 0.65:1 |  |  |
| GPD1 | IC#SQLK (SEQ ID NO: 38) | 0.54:1 |  | ✓ |
| ICL1 | GGTQC#SIMR (SEQ ID NO: 39) | >100:1 |  | ✓ |
| IPP1 | NC#FPHHGYIHNYGAFPQTWEDPNVS-HPETK (SEQ ID NO: 40) | 0.76:1 |  |  |
| LPD1 | VC#HAHPTLSEAFK (SEQ ID NO: 41) | 1.30:1 |  | ✓ |
| PEP4 | KGWTGQYTLDC#NTR (SEQ ID NO: 42) | 2.60:1 |  | ✓ |
| PSA1 | SVVLC#NSTIK (SEQ ID NO: 43) | 0.56:1 |  |  |
| PGM2 | C#TGGIILTASHNPGGPENDMGIK (SEQ ID NO: 44) | 0.58:1 |  | ✓ |
|  | LSIC#GEESFGTGSNHVR (SEQ ID NO: 45) | 0.62:1 |  |  |
| PCK1 | C#PLK | 1.59:1 |  |  |
|  | IPC#LADSHPK (SEQ ID NO: 46) | 1.47:1 |  |  |
|  | C#INLSAEKEPEIFDAIK (SEQ ID NO: 47) | 1.52:1 |  | ✓ |
|  | C#AYPIDYIPSAK (SEQ ID NO: 48) | 1.41:1 |  |  |
|  | IVEEPTSKDEIWWGPVNKPC#SER (SEQ ID NO: 49) | 1.85:1 |  |  |
| QCR6 | ALVHHYEEC#AER (SEQ ID NO: 50) | 1.30:1 |  | ✓ |
| RPL1A¶ | SC#GVDAMSVDDLKK (SEQ ID NO: 51) | 0.82:1 |  |  |
| SAH1 | HPEMLEDC#FGLSEETTTGVHHLYR (SEE ID NO: 52) | 0.62:1 |  |  |
|  | EC#INIKPQVDR (SEQ ID NO: 53) | 0.74:1 |  |  |
| SOD1 | GFHIHEFGDATNGC#VSAGPHFNPFK (SEQ ID NO: 54) | 0.46:1 |  | ✓ |
| TEF1 | RGNVC#GDAK (SEQ ID NO: 55) | 0.81:1 |  |  |
|  | C#GGIDK (SEQ ID NO: 56) | 0.70:1 |  |  |
|  | FVPSKPMC#VEAFSEYPPLGR (SEQ ID NO: 57) | 0.74:1 |  |  |
| VMA2 | IPIFSASGLPHNEIAAQIC#R (SEQ ID NO: 58) | 0.70:1 |  |  |
| YHB1 | HYSLC#SASTK (SEQ ID NO: 59) | 0.69:1 |  |  |

*Gene names are according to the Yeast Proteome Database (YPD) (19).
Cysteinyl residue is ICAT-labeled.
†Protein expression ratios were calculated as described in FIG. 3.
⁻Carbon source for yeast growth was 2% ethanol (Eth) or 2% galactose (GAL0.
§Gene is known to be galactose- or glucose-repressed (19).
¶Eight other ribosomal proteins were detected at similar gene expression levels.

TABLE 4

| Disease | Enzyme | Dysfunction |
|---|---|---|
| Butyrylcholinesterase deficiency | BCHE | Decreased or absent enzyme activity |
| Essential fructosuria hepatic fructokinase deficiency | Fructokinase | Deficient enzyme activity |
| Hereditary fructose intolerance | Fructose 1,6-bisphosphate aldolase B | Deficient enzyme activity |
| Hereditary fructose 1,6-diphosphatase deficiency | Fructose 1,6-bisphosphatase | Deficient enzyme activity |
| Erythrocyte aldolase deficiency with nonspherocytic hemolytic anemia (aldolase A deficiency) | Fructose 1,6-bisphosphate aldolase A | Deficient enzyme activity |
| Glycogen storage disease type Ia (von Gierke disease) | Glucose 6-phosphatase | Absent or deficient enzyme activity |
| Glycogen storage disease type Ib | Glucose 6-phosphate translocase | Deficient transport of glucose 6-phosphate across the membrane of endoplasmic reticulum |
| Glycogen storage disease type III | Amylo-1,6-glucosidase (debrancher enzyme) | Absent or deficient enzyme activity |
| Glycogen storage disease type IV (Andersen disease) | α-1, 4 glucan-6-α-glucosyltransferase | Deficient enzyme activity |

TABLE 4-continued

| Disease | Enzyme | Dysfunction |
| --- | --- | --- |
| Glycogen storage disease type V (McArdle disease) | Muscle glycogen phosphorylase | Absent or deficient enzyme |
| Glycogen storage disease X-linked phosphorylase kinase deficiency | Phosphorylase b-kinase | Deficient or absent enzyme activity function |
| Glycogen storage disease autosomal phosphorylase kinase deficiency | Phosphorylase b-kinase | Deficient enzyme activity |
| Glycogen storage disease liver phosphorylase deficiency | Liver phosphorylase | Deficient enzyme activity |
| Glycogen storage disease type VII (Tarui disease) | Muscle phosphofructokinase 1 | Deficient enzyme activity |
| Liver glycogen synthase deficiency | Liver glycogen synthase | Unknown |
| Phosphoglycerate kinase deficiency | Phosphoglycerate kinase | Deficient enzyme |
| Phosphoglycerate mutase deficiency | Phosphoglycerate mutase | Deficient enzyme |
| Muscle lactate dehydrogenase deficiency | Muscle-specific subunit of lactate dehydrogenase (LDH) | Absence of M subunit of LDH. Muscle LDH is a tetramer of the heart-specific subunit |
| Glucose phosphate isomerase deficiency | Glucose phosphate isomerase | Unknown |
| Transferase deficiency galactosemia | Galactose 1-phosphate uridyltransferase | Deficient enzyme activity |
| Galactokinase deficiency galactosemia | Galactokinase | Deficient enzyme activity |
| Epimerase deficiency galactosemia | Uridine diphosphate galactose-4-epimerase | Deficient enzyme action in blood cells only (benign) or, more rarely, in all tissues (generalized) |
| Phenylketonuria (PKU) due to PAH deficiency | Phenylalanine hydroxylase (PAH) | Deficient or absent PAH activity (<1% normal) |
| Hyperphenylalaninemia due to DHPR-deficiency | Dihydropteridine reductase (DHPR) | Deficient or absent DHPR activity |
| Hyperphenylalaninemia due to GTP-CH-deficiency | Guanosine triphosphate cyclohydrolase (GTP-CH) | Deficient enzyme activity |
| Hyperphenylalaninemia due to 6-PTS-deficiency | 6-Pyruvoyl tetrahydropterin synthase (6-PTS) | Deficient enzyme activity |
| Oculocutaneous tyrosinemia (tyrosinemia type II, tyrosine amino-transferase deficiency) | Tyrosine aminotransferase | Decreased activity |
| 4-Hydroxyphenylpyruvic acid dioxygenase (tyrosinemia type III) | 4-Hydroxy-phenylpyruvic acid dioxygenase | Decreased activity |
| Maleylacetoacetate isomerase deficiency (tyrosinemia type Ib) (tentative) | Maleylacetonacetate isomerase | Presumably decreased enzyme activity |
| Hepatorenal tyrosinemia (tyrosinemia type I: fumarylacetoacetate hydrolase deficiency) | Fumarylacetoacetate hydroxylase | Deficient enzyme activity |
| Carbamyl phosphate synthetase deficiency | Carbamyl phosphate synthetase I | Absent or deficient enzyme activity |
| Ornithine transcarbamylase deficiency | Ornithine transcarbamylase | Absent or reduced enzyme activity |
| Argininosuccinic acid synthetase deficiency | Argininosuccinic acid synthetase | Deficient enzyme activity |
| Argininosuccinase deficiency | Argininosuccinate lyase | Deficient enzyme activity |
| Arginase deficiency | Liver arginase | Deficient enzyme activity |
| Familial hyperlysinemia (variant: saccharopinuria) | α-Aminoadipic semialdehyde synthase | Deficient enzyme activity |
| Maple syrup urine disease (MSUD) or branched chain ketoacidemia | Branched-chain α-keto acid dehydrogenase | Deficient or absent (<2%) BCKAD complex activity in mitochondria; immunologic absence or reduced levels of enzyme subunits; impairment of E1 subunit assembly |
| Cystathionine β-synthase deficiency | Cystathionine β-synthase | Deficient enzyme activity |
| α-Cystathionase deficiency | α-Cystathionase | Deficient enzyme activity |
| Hepatic methionine adenosyltransferase deficiency | Isoenzyme of methionine adenosyltransferase | Deficient enzyme activity |

TABLE 4-continued

| Disease | Enzyme | Dysfunction |
|---|---|---|
| Sarcosinemia | Sarcosine dehydrogenase? | Deficient enzyme activity |
| Nonketotic hyperglycinemia | Glycine cleavage system | Deficient enzyme activity |
| Hyperuracil thyminuria | Dihydropyrimidine dehydrogenase | Deficient enzyme activity |
| Dihydropyrimidinuria | Dihydropyrimidinase | Unknown |
| Pyridoxine dependency with seizures | Brain glutamic acid decarboxylase-1 | Deficient coenzyme binding? (brain) |
| GABA aminotransferase deficiency | GABA-α-ketoglutarate transaminase | Deficient enzyme activity |
| 4-Hydroxybutyric aciduria | Succinic semialdehyde dehydrogenase | Deficient enzyme activity |
| Serum carnosinase deficiency and homocarnosinosis | Serum carnosinase | Deficient enzyme |
| Alkaptonuria | Homogentisic acid oxidase | Absent or deficient enzyme activity |
| Isovaleric acidemia | Isovaleryl-CoA dehydrogenase | Deficient enzyme activity, deficient protein, abnormal peptide size |
| Isolated 3-methylcrotonyl-CoA carboxylase deficiency | 3-Methylcrotonyl-CoA carboxylase | Deficient enzyme activity |
| 3-Methylglutaconic aciduria Mild form: | 3-Methylglutaconyl-CoA hydratase | Deficient enzyme activity |
| 3-Hydroxy-3-methylglutaryl-CoA lyase deficiency | 3-Hydroxy-3-methylglutaryl-CoA lyase | Deficient enzyme activity |
| Mevalonic aciduria | Mevalonate kinase | Deficient enzyme activity |
| Mitochondrial acetoacetyl-CoA thiolase deficiency | Mitochondrial acetoacetyl-CoA thiolase (T2) | Deficient enzyme activity, decreased protein, unstable protein |
| Propionic acidemia (2 nonallelic forms designated pccA and pccBC) | Propionyl-CoA carboxylase (PCC) | Deficient enzyme activity (nonallelic forms reflect mutations in nonidentical subunits of PCC) |
| Methylmalonic acidemia (2 allelic variants designated mut° and mut | Methyldmalonyl-CoA mutase (MUT) apoenzyme | Absent MUT activity in mut°, deficient MUT activity due to reduced affinity for cofactor (adenosylcobalamin) in mut |
| Glutaric acidemia type I | Glutaryl-CoA dehydrogenase | Deficient enzyme activity |
| Cytochrome oxidase deficiency | Cytochrome oxidase polypeptides | Decreased activity of the cytochrome oxidase complex |
| Pyruvate dehydrogenase complex deficiency-$E_1$ decarboxylase component | Pyruvate decarboxylase, $E_1\alpha$ | Decreased enzyme activity, decreased protein |
| Pyruvate dehydrogenease $E_2$ transacylase | Dihydrolipoamide transacylase | Decreased enzyme activity; abnormal protein electrophoretic mobility |
| Combined α-ketoacid dehydrogenase deficiency/lipoamide dehydrogenase deficiency | Lipoamide dehydrogenase | Decreased enzyme activity |
| Pyruvate carboxylase deficiency | Pyruvate carboxylase | Absent enzyme activity; 7 cases absent enzyme, protein, and mRNA |
| Carnitine palmitoyl transferase I (CPT I) deficiency | Carnitine palmitoyl transferase I | Deficient enzyme |
| Carnitine/acylcarnitine translocase deficiency | Carnitine/acylcarnitine translocase | Deficient translocase |
| Carnitine palmitoyl transferase II (CPT II) deficiency | Carnitine palmitoyl transferase II | Deficient enzyme |
| Very long-chain acyl-CoA dehydrogenase (VLCAD) deficiency | Very long-chain acyl-CoA dehydrogenase | Deficient enzyme |
| Long-chain acyl-CoA dehydrogenase (LCAD) | Long-chain acyl-CoA dehydrogenase | Deficient enzyme |
| Long-chain L-3-hydroxyacyl-CoA dehydrogenase (LCHAD) deficiency | L-3-hydroxyacyl-CoA dehydrogenase | Deficient enzyme |
| Trifunctional enzyme (TFE) deficiency | Trifunctional enzyme | Deficient enzyme |
| Dienolyl-Co reductase deficiency | 2,4-dienoyl-CoA reductase | Deficient enzyme |

TABLE 4-continued

| Disease | Enzyme | Dysfunction |
| --- | --- | --- |
| Medium-chain acyl-CoA dehydrogenase (MCAD deficiency | Medium-chain acyl-CoA dehydrogenase | Deficient enzyme |
| Short-chain acyl-CoA dehydrogenase (SCAD) deficiency | Short-chain acyl-CoA dehydrogenase | Deficient enzyme |
| Glutaric acidemia type II | Electron transfer flavoprotein (ETF); ETF: ubiquinone oxidoreductase | In some cases, no enzyme antigen; in others, no enzyme activity |
| Glycerol kinase deficiency (Gkd) | Glycerol kinase | The microdeletion involves not only GK but also the other deleted loci: AHC, DMD, OTC, and other linked loci |
| Primary gout: superactive variant of phosphoribosylpyrophosphate (PP-ribose-P) synthetase | PP-ribose-P synthetase | Enhanced enzyme activity |
| Primary gout: partial deficiency of hypoxanthine guanine phosphoribosyltransferase (HPRT) | Hypoxanthine guanine phosphoribosyl transferase (HPRT) | Absent or deficient enzyme activity |
| Lesch-Nyhan syndrome: deficiency of hypoxanthine guanine phosphoribosyltransferase (HPRT) | Hypoxanthine guanine phosphoribosyltransferase (HPRT) | Absent or deficient enzyme activity |
| 2,8-Dihydroxyadenine lithiasis (adenine phosphoribosyltransferase deficiency) | Adenine phosphoribosyltransferase | Type I: absent enzyme activity; type II: reduced affinity for PP-ribose-P |
| Adenosine deaminase deficiency with severe combined immunodeficiency disease | Adenosine deaminase | Absent or greatly diminished enzyme activity |
| Purine nucleoside phosphorylase deficiency with cellular immunodeficiency | Purine nucleoside phosphorylase | Absent or greatly diminished enzyme activity |
| Myoadenylate deaminase deficiency | Myoadenylate deaminase (AMPDI) | No enzyme activity; on immunoreactive protein |
| Xanthinuria | Xanthine dehydrogenase (xanthine oxidase) | Type I: absent xanthine dehydrogenase activity; type II: absent xanthine dehydrogenase and aldehyde oxidase activity |
| Hereditary orotic aciduria | UMP synthase (unstable protein) | Deficient enzyme activity |
| Pyrimidine 5′-nucleotidase deficiency | Pyrimidine 5′-nucleotidase | Absent or unstable enzyme |
| Dihydropyrimidine dehydrogenase deficiency | Dihydropyrimidine dehydrogenase | Absent or unstable enzyme |
| Dihydropryimidase deficiency | Dihydropyrimidase | Absent or unstable enzyme |
| Familial lipoprotein lipase deficiency | Lipoprotein lipase | Nonfunctional protein in some, nondectable enzyme activity and protein in others |
| Familial lecithin: chloesterol acyltransferase deficiency | Lecithin: cholesterol acyltransferase | Absent enzyme protein or deficient enzyme activity |
| δ-Aminolevulinic acid dehydratase porphyria | δ-Aminolevulinic acid dehydratase | Minimal enzyme activity |
| Acute intermittent porphyria | Porphobilinogen deaminase | Decreased enzyme activity (~50%) |
| Congenital erythropoietic porphyria | Uroporphyrinogen III cosynthase | Minimal enzyme activity |
| Porphyria cutanea tarda (familial form) | Uroporphyrinogen decarboxylase | Decreased enzyme activity (~50%) |
| Hepatoerythropoietic porphyria | Uroporphyrinogen decarboxylase | Minimal enzyme activity |
| Hereditary coproporphyria | Coproporphyrinogen oxidase | Decreased enzyme activity (~50%) |
| Variegate porphyria | Protoporphyrinogen oxidase | Decreased enzyme activity (~50%) |
| Erythropoietic protophorphyria | Ferrochelatase | Decrease enzyme activity (~50%) |
| Crigler-Najjar syndrome, type I | Bilirubin UDP-glucuronosyltransferase | Absent enzyme activity |

TABLE 4-continued

| Disease | Enzyme | Dysfunction |
| --- | --- | --- |
| Crigler-Najjar syndrome, type II | Bilirubin UDP-glucuronosyltransferase | Markedly reduced enzyme activity |
| Gilbert syndrome | Bilirubin UDP-glucuronosyltransferase activity | Reduced enzyme activity |
| Refsum disease | Phytanic acid α-hydroxylase | Deficient enzyme activity |
| Primary hyperoxaluria type 1 | Alanine-glyoxylate aminotransferase | Loss of enzyme catalytic activity and aberrant subcellular distribution |
| Primary hyperoxaluria type 2 | Glyoxylate reductase/D-glycerate dehydrogenase | Loss of enzyme catalytic activity |
| $G_{M2}$ gangliosidosis: hexosaminadase α-subunit deficiency (variant B, Tay-Sachs disease) | β-hexosaminidase | Absent or defective hexosamininidase A (αβ) activity |
| Glycogen storage disease type II | α-glucosidase | Absent or deficient enzyme activity |
| Mucopolysaccharidosis I (Hurler, Scheie, and Hurler-Sheie syndromes, MPS, MPS IS,MPS IH/S) | αa-L-iduronidase | Absent enzyme activity |
| Mucopolysaccharidosis II (Hunter syndrome) | Iduronate sulfatase | Absent enzyme activity |
| Mucopolysaccharidosis III (Saniflippo syndrome) types A, B, C and D | IIIA: Heparan N-sulfatase<br>IIIB: α-N-acetyl-glucosaminidase<br>IIIC: Acetyl-CoA: α-glucosaminide acetyltransferase<br>IIID: N-acetyl-glucosamine-6-sulfatase | Absent enzyme activity |
| Mucopolysaccharidosis IV (Morquio syndrome) types A and B | IVA: Galactose 6-sulfatase<br>IVB: βGalactosidase | Absent enzyme activity |
| Mucopolysaccharidosis VI (Maroteaux-Lamy syndrome) | N-acetyl-galactosamine 4-sulfatase | Absent enzyme activity |
| Mucopolysaccharidosis VII (Sly syndrome) | βglucuronidase | Absent enzyme activity |
| I-cell disease (ML-II) | N-acetylglucosaminyl-I-phosphotransferase | Phosphorylation of many lysosomal enzymes |
| Schindler disease (α-N-acetyl-galactosaminidase deficiency) | α-N-acetyl-galactosaminidase | Deficient activity of α-N-acetylgalactosaminidase |
| α-Mannosidosis | α-D-mannosidase enzyme activity | Deficient or unstable |
| β-Mannosidosis | β-D-mannosidase | Deficient enzyme activity |
| Sialidosis | α-neuraminidase | Deficient enzyme activity |
| Aspartylglucosaminuria | Aspartyglucosaminidase | Deficient enzyme activity |
| Fucosidosis | α-L-fucosidase | Deficient enzyme activity |
| Wolman disease and cholesteryl ester storage disease | Acid lipase | Deficient enzyme activity |
| Ceramidase deficiency (Farber lipogranulomatosis) | Ceramidase | Deficient enzyme activity |
| Niemann-Pick disease (NPD) types A and B (primary sphingomyelin storage) | Sphingomyelinase | Deficient sphingomyelinase activity |
| Gaucher disease type I (nonneuronopathic) | Glucocerebrosidase | Decreased catalytic activity and some instability of enzyme protein |
| Globoid-cell leukodystrophy (Krabbe disease) | Galactosylceramidase | Absent enzyme activity |
| Metachromatic leukodystrophy | Arylsulfatase A | Deficient enzyme activity |
| Fabry disease | α-Galactosidase A | Nonfunctional or unstable enzyme protein |
| $G_{M1}$ gangliosidosis | Acid β-galactosidase (GLBI) | Deficient enzyme activity |
| $G_{M2}$ gangliosidosis: hexosaminidase α-subunit deficiency (variant B, Tay-Sachs disease) | βhexosaminidase | Absent or defective hexosaminidase A (αβ) activity |

TABLE 4-continued

| Disease | Enzyme | Dysfunction |
| --- | --- | --- |
| Steroid 21-hydroxylase deficiency salt-losing form | Steroid 21-hydroxylase | Absent or truncated enzyme with no activity |
| Steroid 5α-reductase 2 deficiency | Steroid 5α-reductase 2 | Absent or unstable enzyme activity |
| Steroid sulfatase deficiency (X-linked ichthyosis | 3β-hydroxysteroid sulfatase | Absent immunoreactive and enzymatically active protein (both deletion and nondeletion patients |
| Methylenetetrahydrofolate reductase deficiency | Methylenetetrahydrofolate reductase | Absent or deficient enzyme activity. Thermolabile variants have been described |
| Holocarboxylase synthetase deficiency | Holocarboxylase synthetase | Deficient holocarboxylase synthetase activity |
| Biotinidase deficiency | Biotinidase | Deficient biotinidase activity |
| Hereditary methemoglobinemia secondary to cytochrome $b_5$ reductase deficiency, types I, II and III | Cytochrome $b_5$ reductase | Deficient enzyme activity in erythrocyte cytosol only (type I), in all tissues (type II), and in all hematopoetic cells (type III) |
| Pyruvate kinase deficiency hemolytic anemia | Pyruvate kinase | Deficient enzyme activity |
| Hexokinase deficiency hemolytic anemia | Hexokinase | Deficient enzyme activity |
| Glucosephosphate isomerase deficiency hemolytic anemia | Glucosephosphate isomerase | Deficient enzyme activity |
| Aldolase deficiency hemolytic anemia | Aldolase (A type) | Deficient enzyme activity |
| Triosephosphate isomerase deficiency hemolytic anemia | Triosephosphate isomerase | Enzyme activity deficient in all tissues |
| Phosphoglycerate kinase deficiency hemolytic anemia | Phospoglycerate kinase | Deficient enzyme activity in hemizygotes |
| 2,3-Diphospho-glyceromutase and phosphatase deficiency | 2,3-Diphospho-glycerate-mutase and phosphatase (1 protein) | Deficient enzyme activity |
| 6-Phosphogluconate dehydrogenase deficiency | 6-Phosphogluconate dehydrogenase | Enzyme activity deficiency |
| Glutathione peroxidase deficiency | Glutathione peroxidase | Diminished enzyme activity |
| Glutathione reductase deficiency | Glutathione reductase | Deficient enzyme activity |
| Glutathione synthetase deficiency hemolytic anemia | Glutathione synthetase | Deficient enzyme activity |
| γ-Glutamylcysteine synthetase deficiency hemolytic anemia | γ-Glutamylcysteine synthetase | Deficient enzyme activity |
| Adenosine deaminase hyperactivity hemolytic anemia | Adenosine deaminase | Overproduction of structurally normal enzyme protein mediated at mRNA translation level |
| Pyrimidine nucleotidase deficiency hemolytic anemia | Pyrimidine nucleotidase | Deficient enzyme activity |
| Myeloperoxidase deficiency | Myeloperoxidase enzyme activity | Absent or deficient |
| Carbonic anhydrase II deficiency syndrome (osteopetrosis with renal tubular acidosis) | Carbonic anhydrase II | Quantitative deficiency of carbonic anhydrase II |
| Albinism, oculocutaneous tyrosinase-negative type (OCAIA) | Tyrosinase | Absent, reduced, or unusual enzyme activity |
| Canavan disease | Aspartoacylase | Deficient enzyme activity |

TABLE 5

Molecular masses of protonated and sodiated substrate-conjugates, products, and internal standards for CDGS enzymes m/z

| Enzyme | Substrate | | Product | | Internal standard | |
|---|---|---|---|---|---|---|
| | $(M + H)^+$ | $(M + Na)^+$ | $(M + H)^+$ | $(M + Na)^+$ | $(M + H)^+$ | $(M + Na)^+$ |
| Type 1a, b | 711 | 733 | 549 | 571 | 555 | 577 |
| Manose-transferase | 725 | 747 | 563 | 585 | 570 | 592 |
| Type II | 1156 | 1178 | 1343 | 1365 | 1348 | 1370 |
| Type | 1126 | 1148 | 2362[a] | 2384[a] | 2367[a] | 2389[a] |

[a]Calculated for the GlcNAc-T II product and internal standard containing a GlcNAc-GlcNAc-Mannose-(Mannose-GlcNAc)$_2$ residue.

Scheme 1

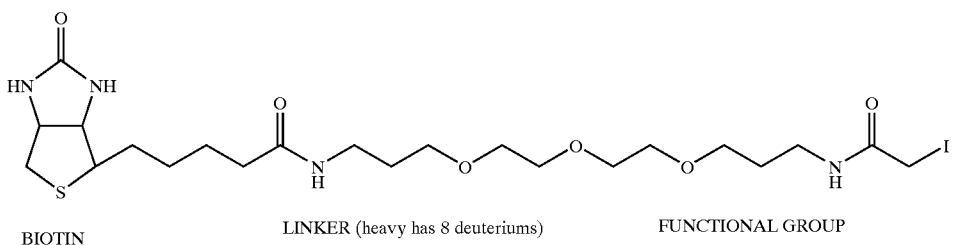

BIOTIN     LINKER (heavy has 8 deuteriums)     FUNCTIONAL GROUP

Flowchart illustration of the procedure for quantitative protein profile measurements based on stable isotope ratios by mass spectrometry

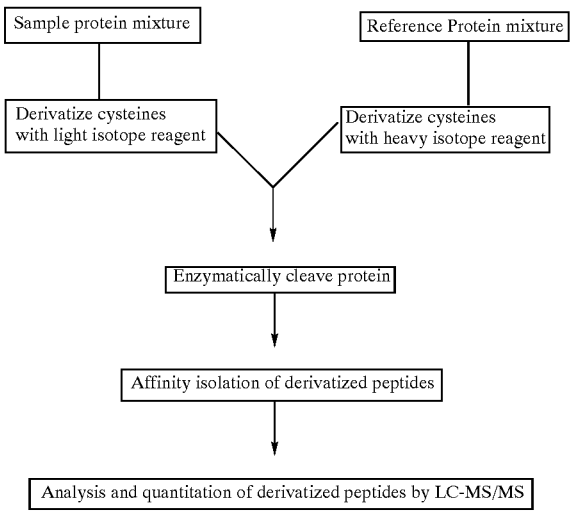

Scheme 2
Custom chemical synthesis of sulfhydryl-reactive biotinylating reagent. Linker can be made either isotopically heavy (8) or light (d0).
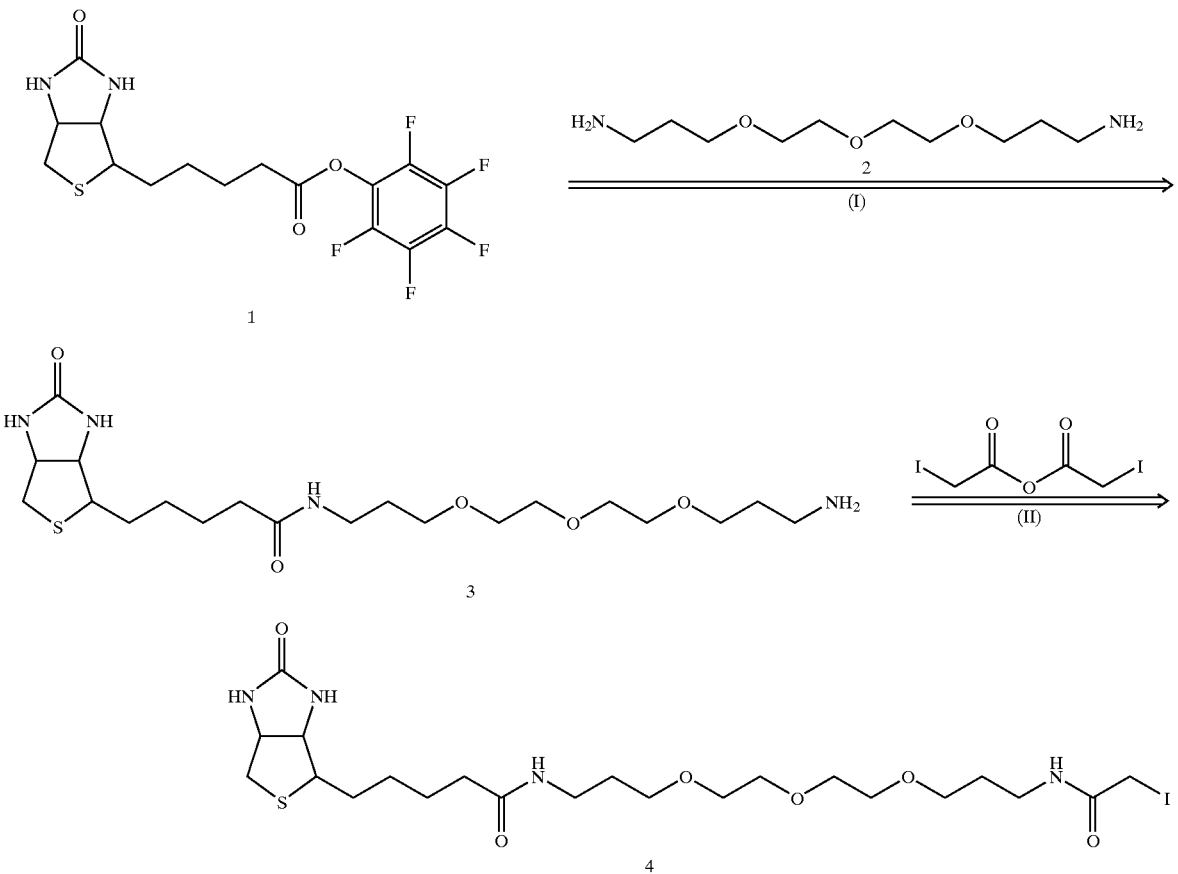
Scheme 3
Synthesis of reagent specific for biotinylation of free amino groups. The reagent is synthesized in both isotopically heavy (d8) or light (d0) form.
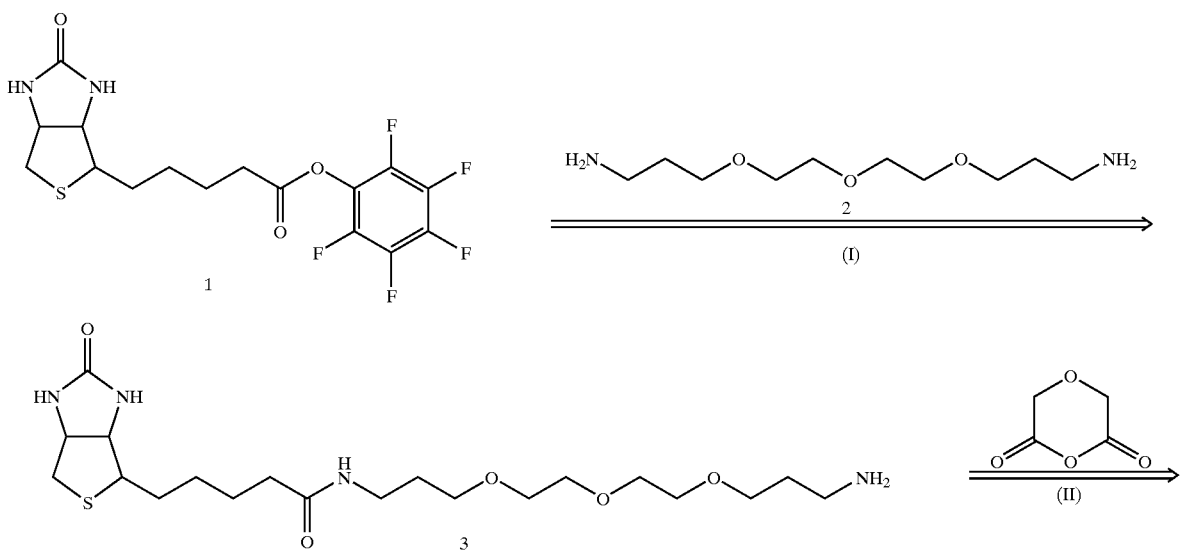

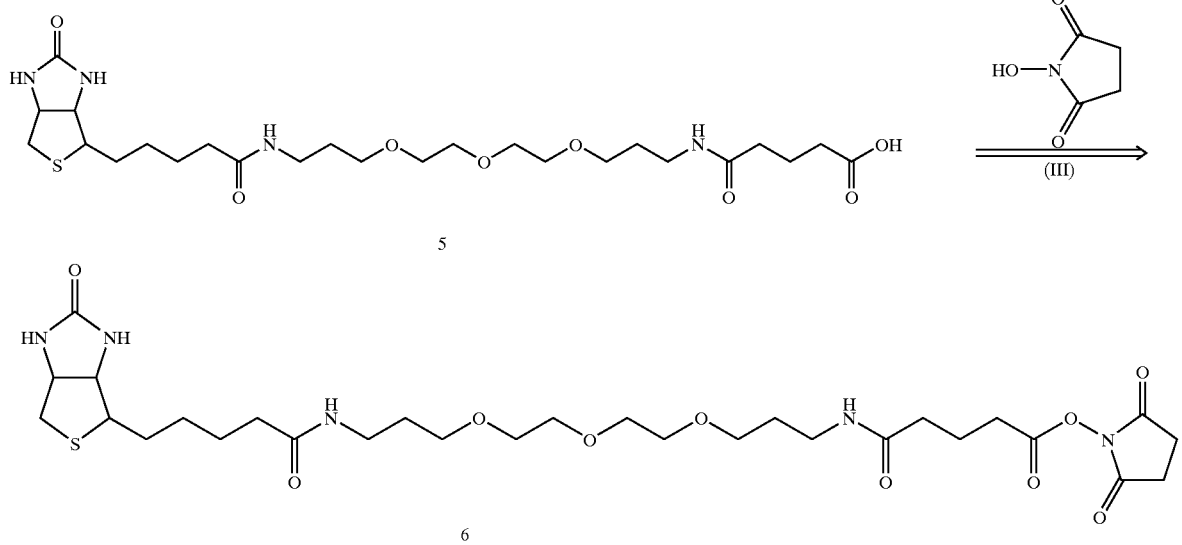
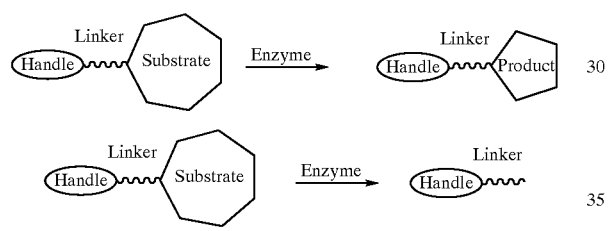
Scheme 5
Structures of Substrate Conjugates 1 and 2, Product Conjugates 3 and 4, and Internal Standards 5 and 6
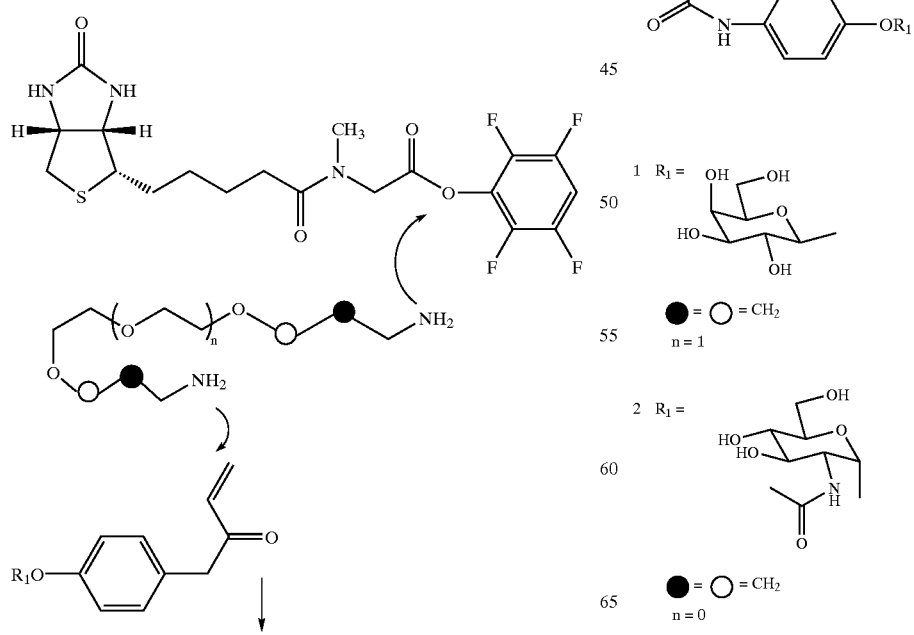

-continued
3  R₁ = H
   ● = ○ = CH₂
   n = 1
4  R₁ = H
   ● = ○ = CH₂
   n = 0
5  R₁ = H
   ● = ○ = CD₂
   n = 1
6  R₁ = H
   ● = CH₂   ○ = CD₂
   n = 0
5
10
15
Scheme 6
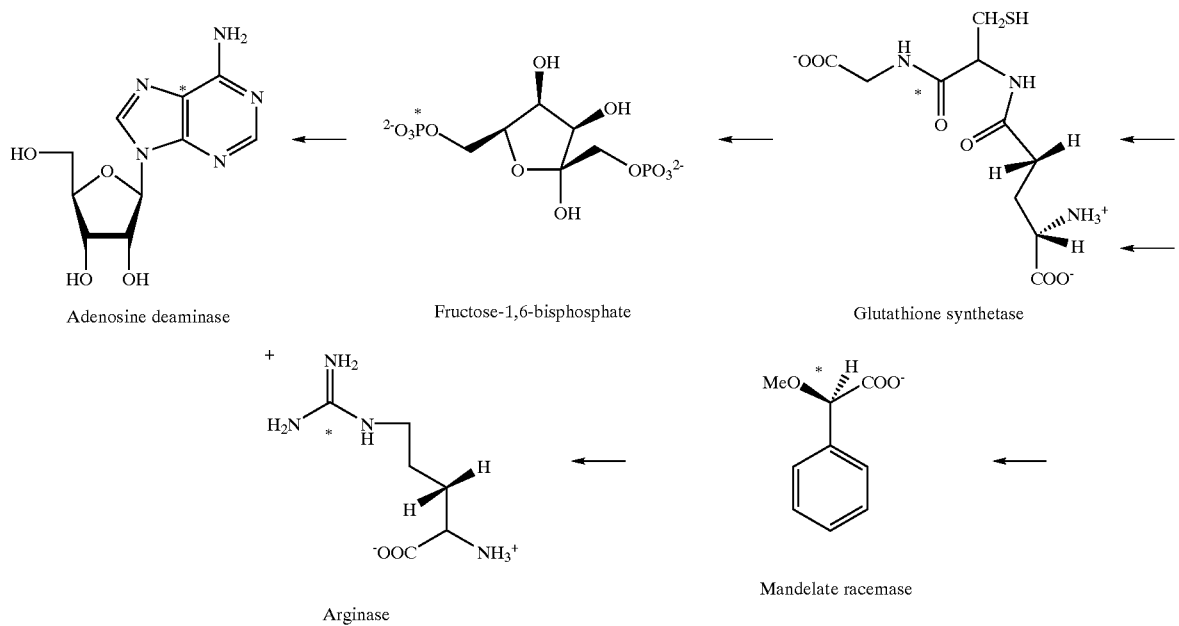
Scheme 7
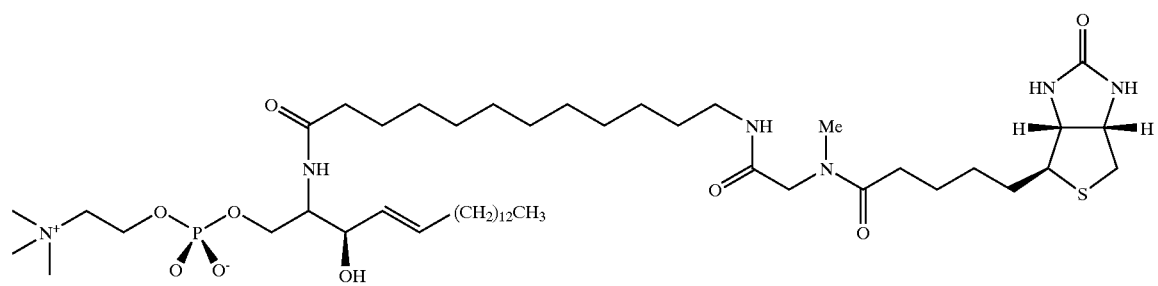

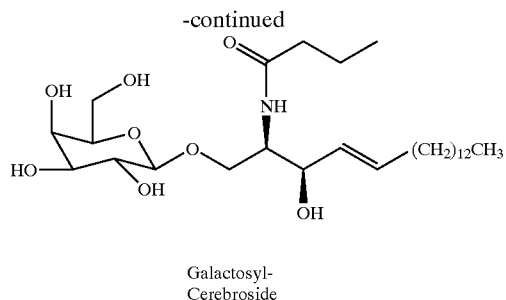
Galactosyl-
Cerebroside
Scheme 8
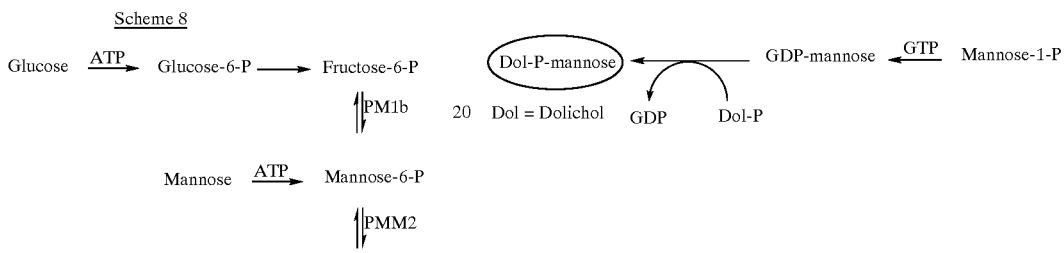
Dol = Dolichol
Scheme 9
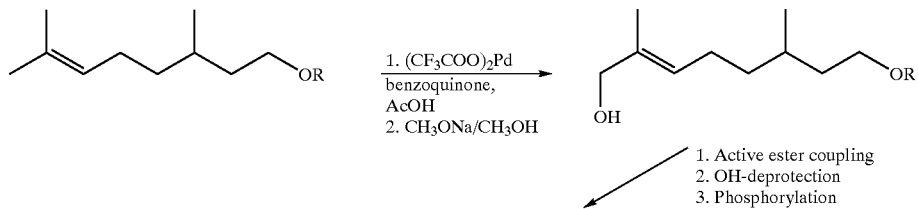
1. Active ester coupling
2. OH-deprotection
3. Phosphorylation
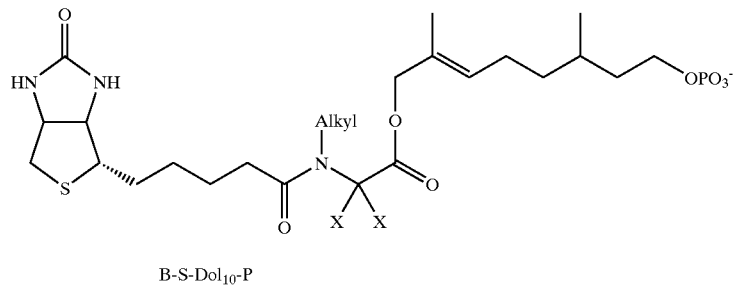
B-S-Dol$_{10}$-P
R = SiMe$_2$t-Bu
Alkyl = CH$_3$
CD$_3$
C$_2$H$_5$
C$_2$D$_5$
X = H or D Scheme 10
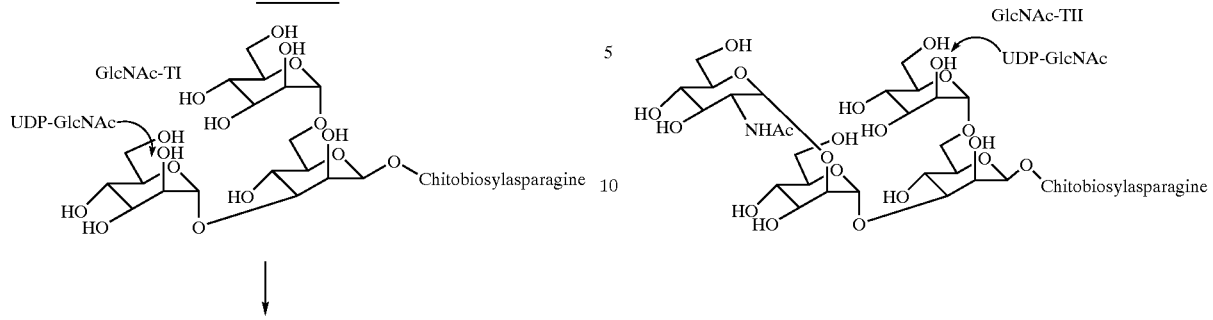
Scheme 11
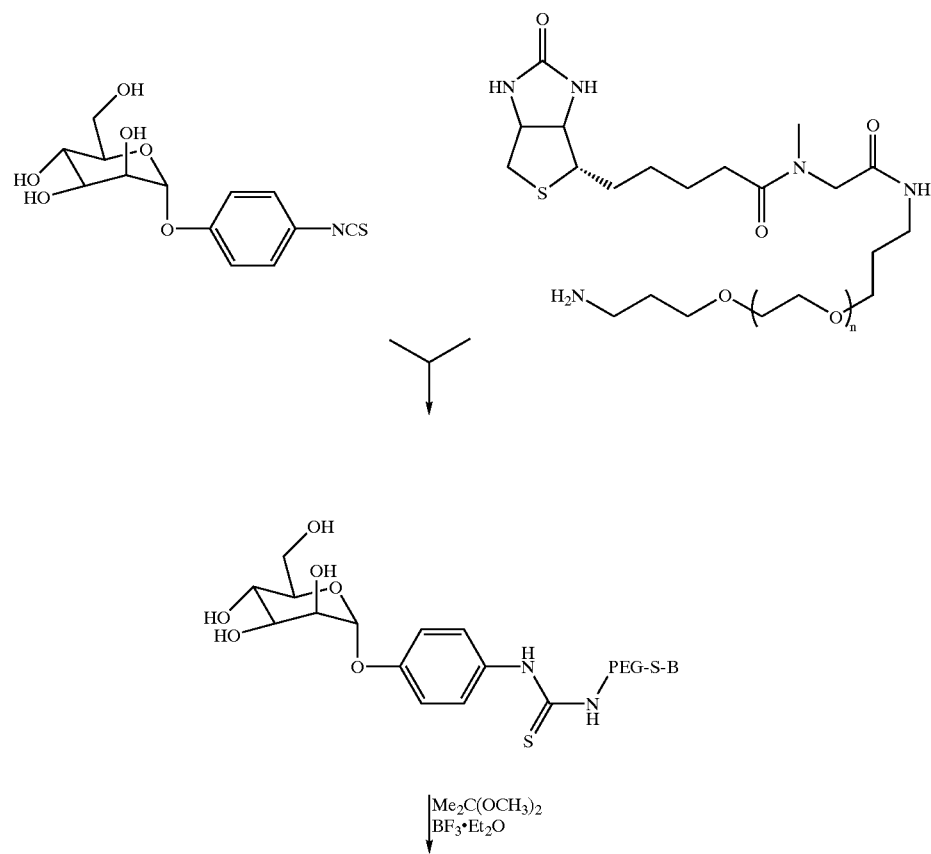
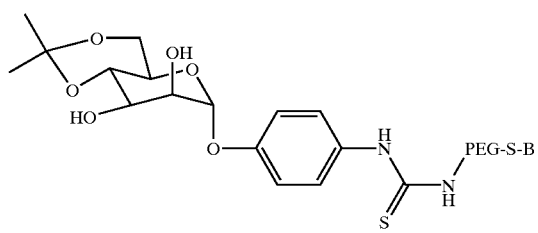

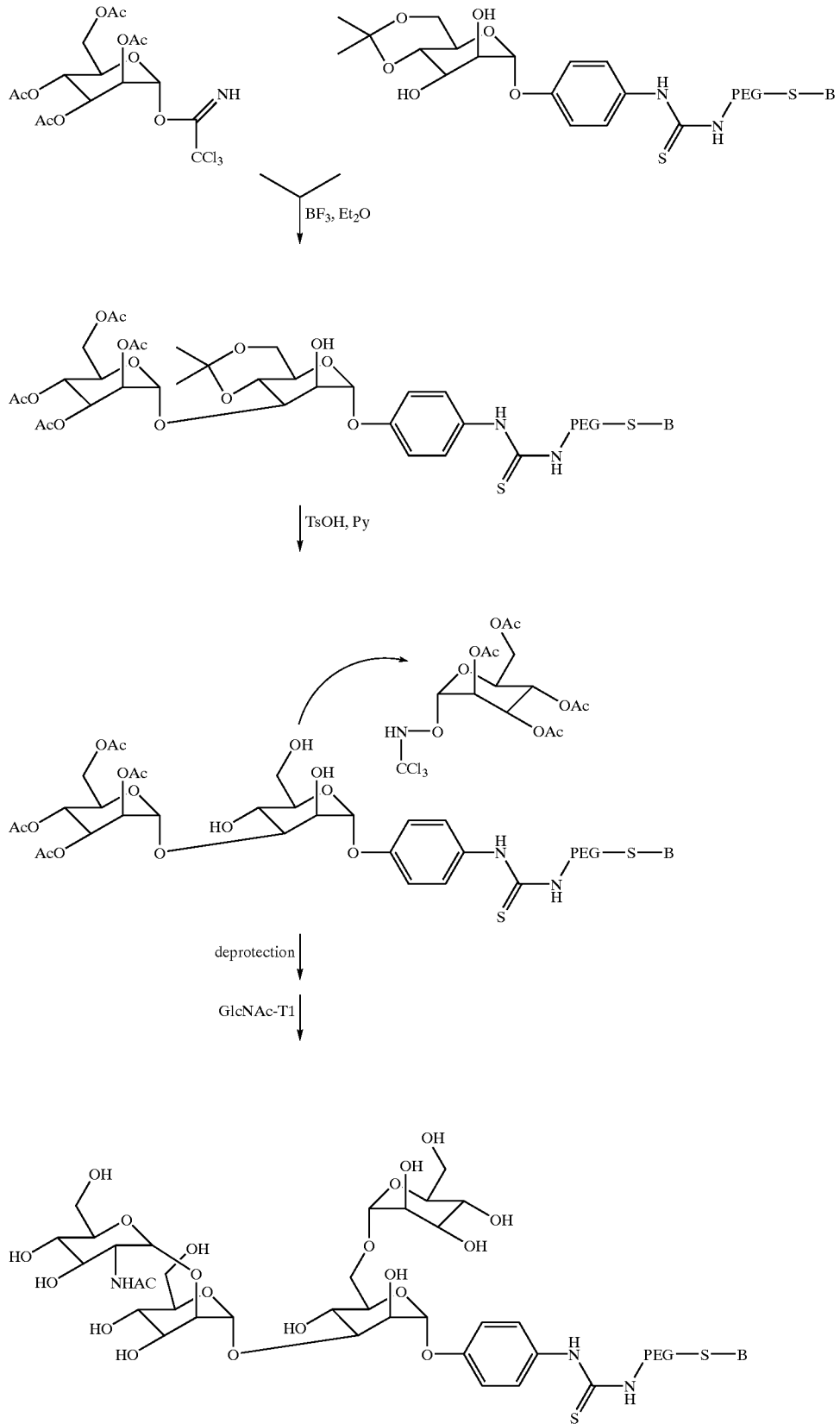
Scheme 12

Scheme 13
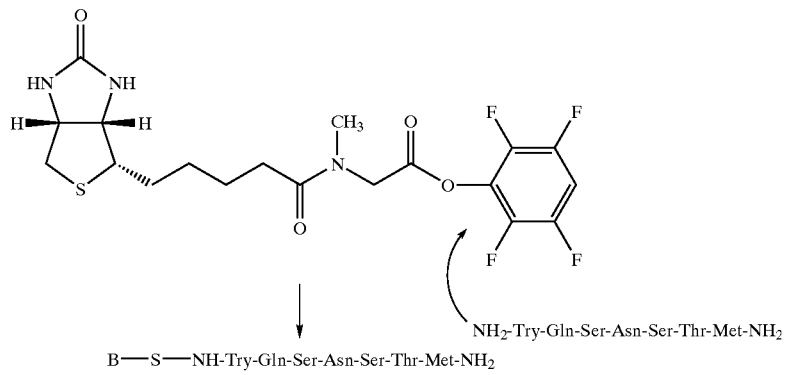
Scheme 14
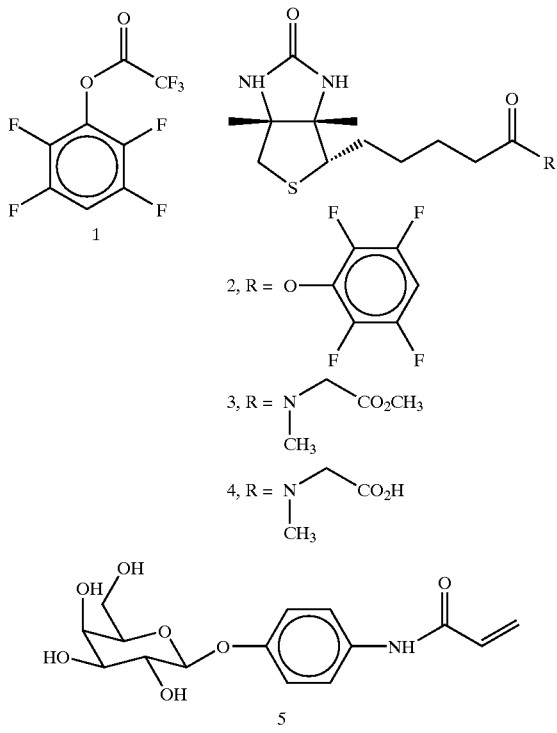
Scheme 15
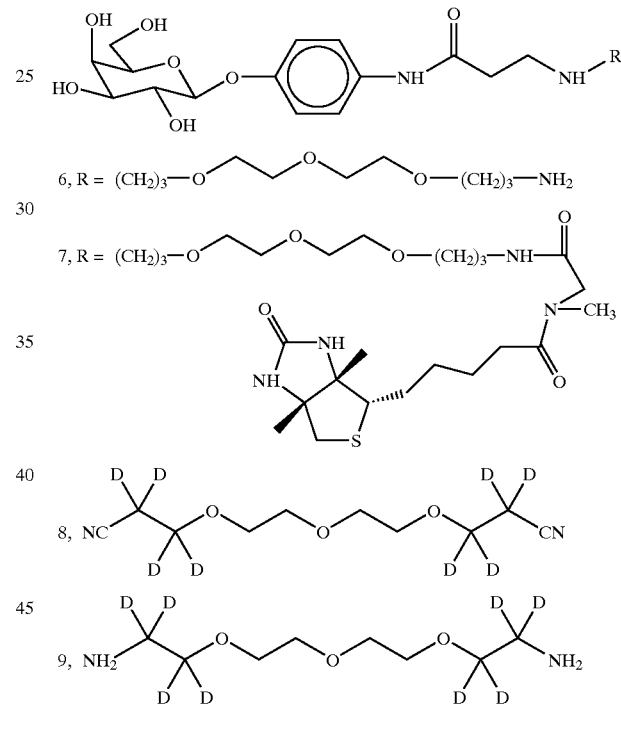
Scheme 16
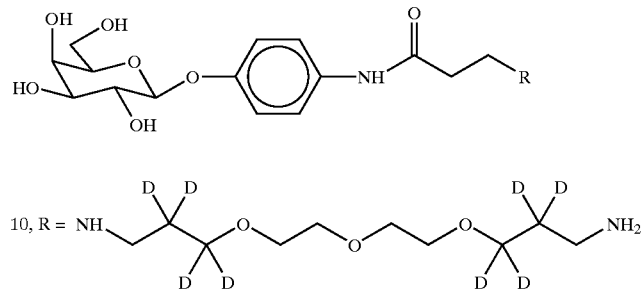

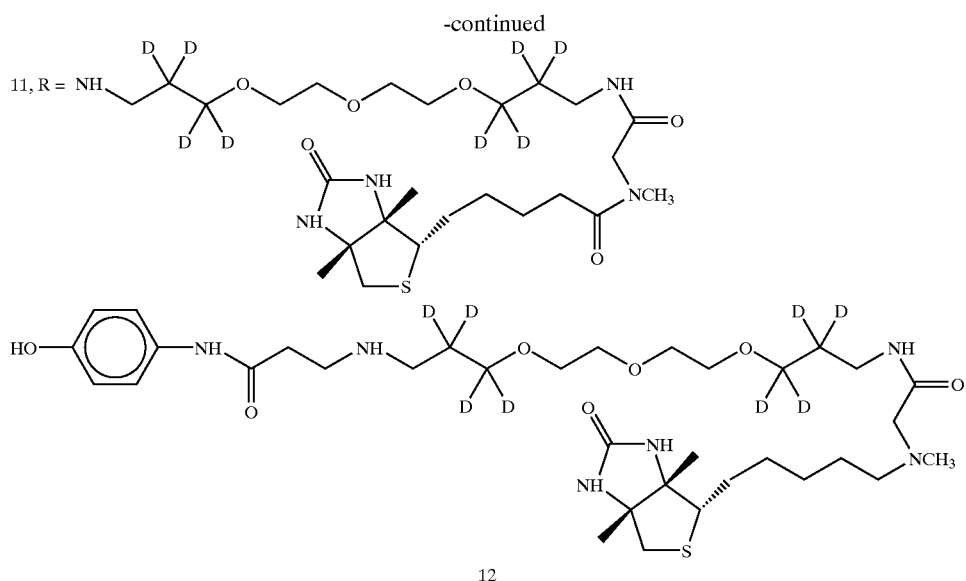
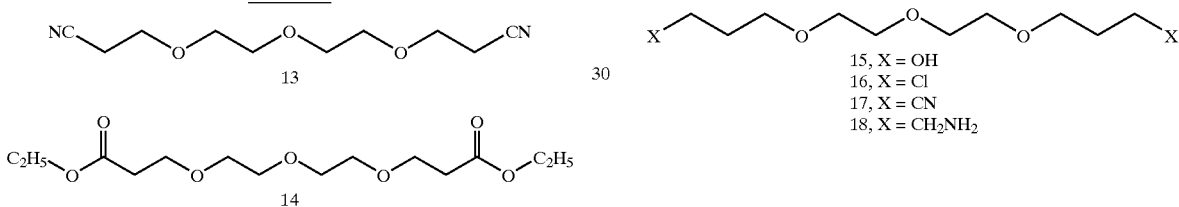
Scheme 17
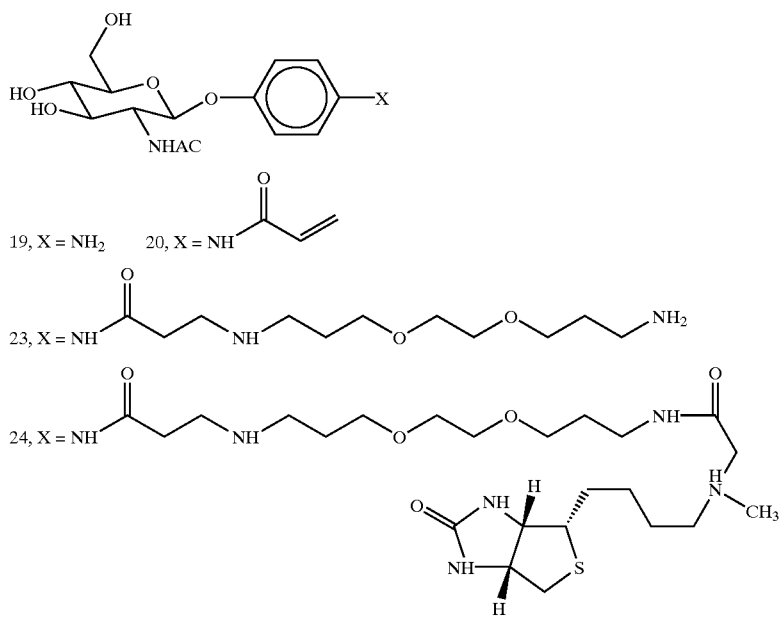
Scheme 18

-continued
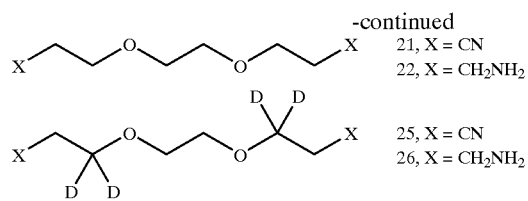
21, X = CN
22, X = CH₂NH₂
25, X = CN
26, X = CH₂NH₂
Scheme 19
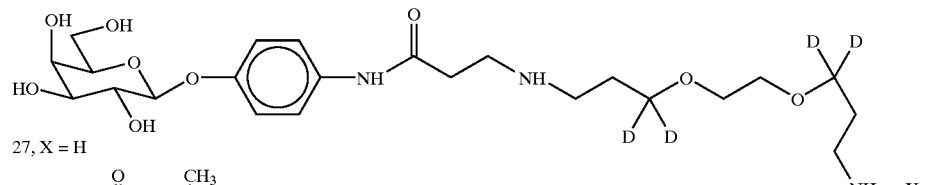
27, X = H
28, X = 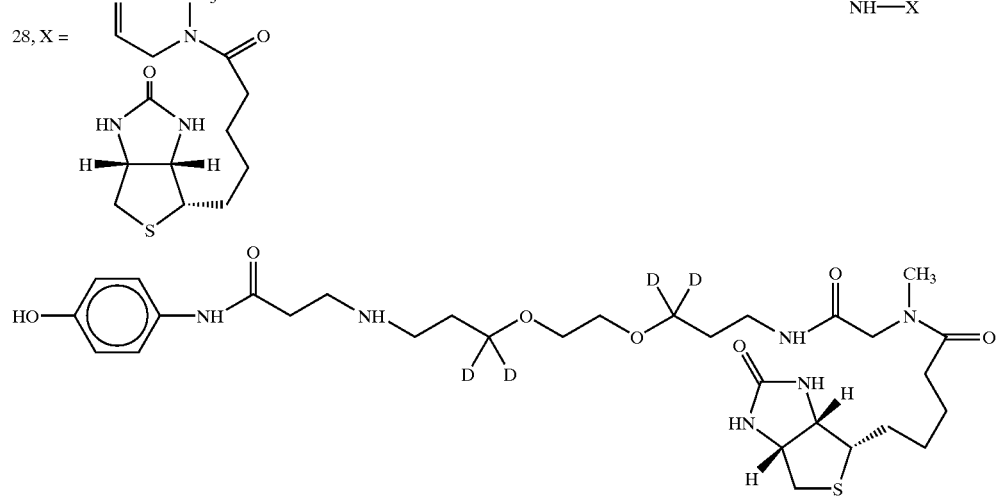
29
Scheme 20
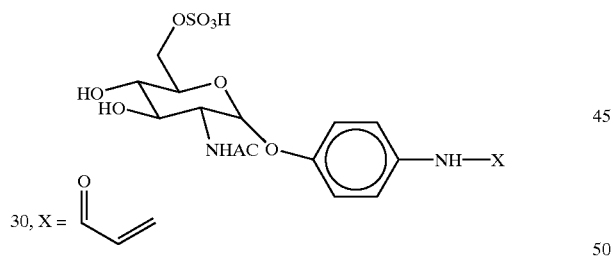
30, X = 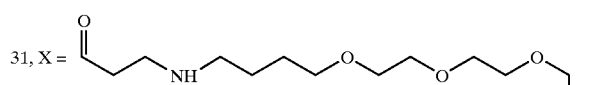
31, X =
32, X = 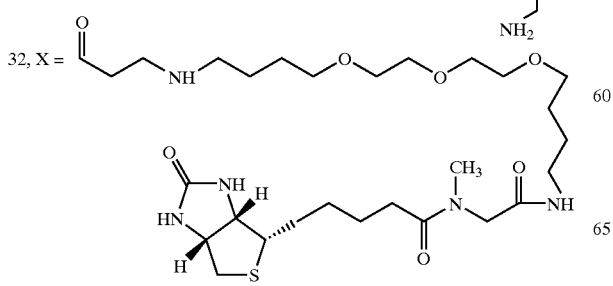

Scheme 21
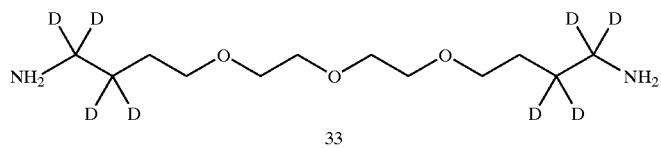
33
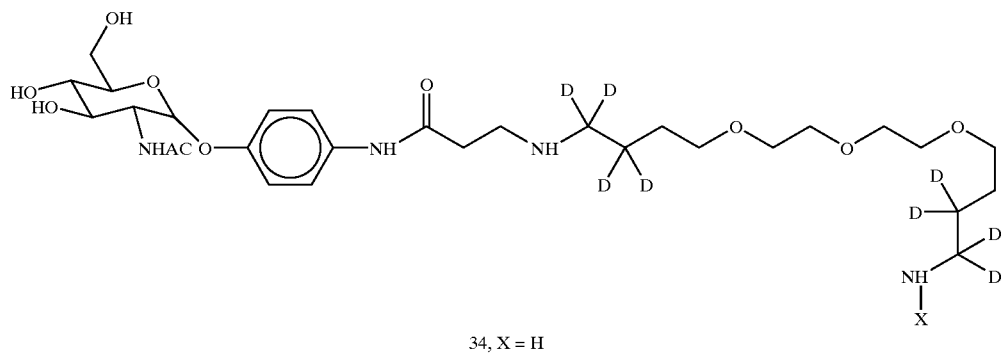
34, X = H
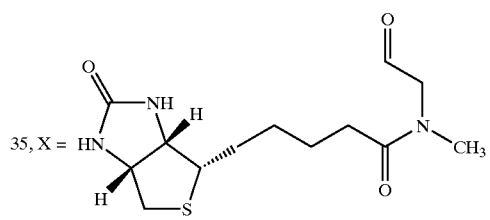
35, X =
Scheme 22
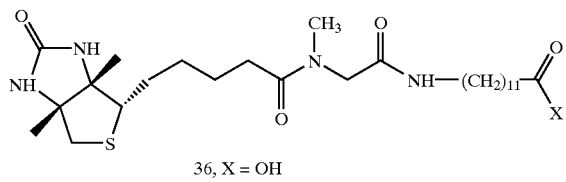
36, X = OH
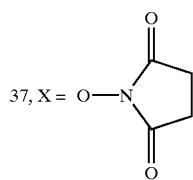
37, X =
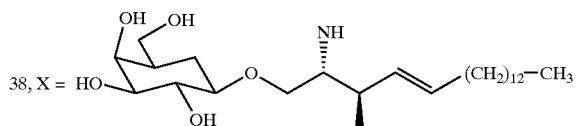
38, X = H
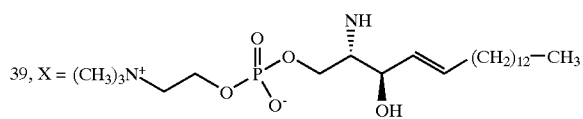
39, X = (CH₃)₃N⁺

Scheme 23

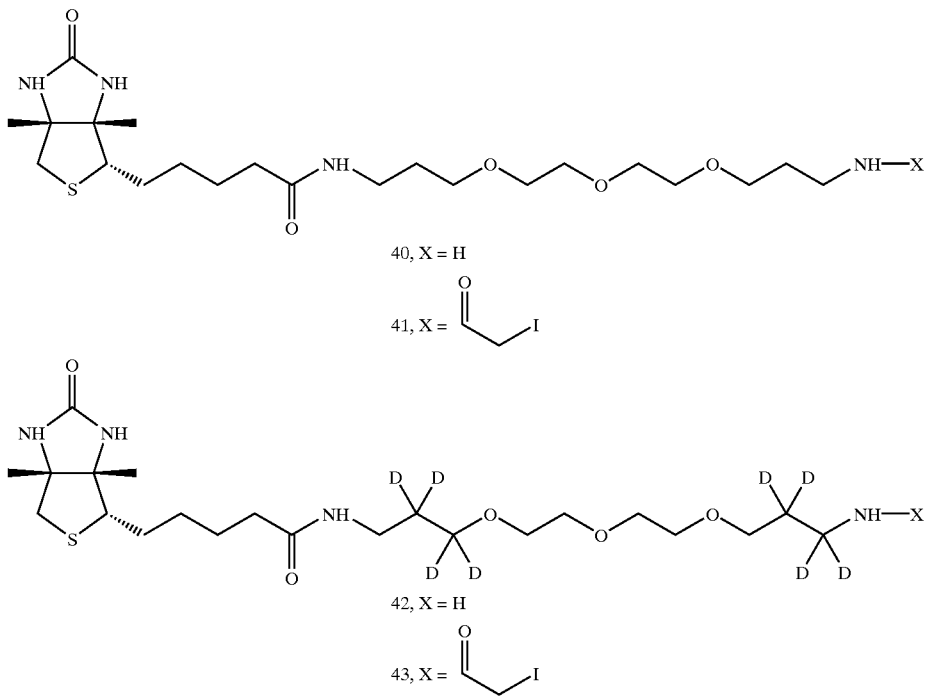

REFERENCES

Ashikaga, K. et al. (1988) Bull. Chem. Soc. Jpn. 61:2443–2450.

Bayer, E. and Wilchek, M. (1990) Methods Enzymol. 184:49–51.

Bleasby, A. J. et al. (1994), "OWL—a non-redundant composite protein sequence database," Nucl. Acids Res. 22:3574–3577.

Boucherie, H. et al. (1996), "Two-dimensional gel protein database of *Saccharomyces cerevisiae*," Electrophoresis 17:1683–1699.

Chen, Y.-T. and Burchell, A. (1995), *The Metabolic and Molecular Bases of Inherited Disease,* Scriver, C. R. et al. (eds.) McGraw-Hill, New York, pp. 935–966.

Clauser, K. R. et al. (1995), "Rapid mass spectrometric peptide sequencing and mass matching for characterization of human melanoma proteins isolated by two-dimensional PAGE," Proc. Natl. Acad. Sci. USA 92:5072–5076.

Cole, R. B. (1997) *Electrospray Ionization Mass Spectrometry: Fundamentals, Instrumentation and Practice,* Wiley, New York.

De Leenheer, A. P. and Thienpont, L. M. (1992), "Application of isotope dilution-mass spectrometry in clinical chemistry, pharmacokinetics, and toxicology," Mass Spectrom. Rev. 11:249–307.

DeRisi, J. L. et al. (1997), "Exploring the metabolic and genetic control of gene expression on a genomic scale," Science 278:680–6

Dongr'e, A. R., Eng, J. K., and Yates, J. R., 3rd (1997), "Emerging tandem-mass-spectrometry techniques for the rapid identification of proteins," Trends Biotechnol. 15:418–425.

Ducret, A., VanOostveen, I., Eng, J. K., Yates, J. R., and Aebersold, R. (1998), "High throughput protein characterization by automated reverse-phase chromatography/electrospray tandem mass spectrometry," Prot. Sci. 7:706–719.

Eng, J., McCormack, A., and Yates, J. I. (1994), "An approach to correlate tandem mass spectral data of peptides with amino acid sequences in a protein database," J. Am. Soc. Mass Spectrom. 5:976–989.

Figeys, D. et al. (1998), "Electrophoresis combined with mass spectrometry techniques: Powerful tools for the analysis of proteins and proteomes," Electrophoresis 19:1811–1818.

Figeys, D., and Aebersold, R. (1998), "High sensitivity analysis of proteins and peptides by capillary electrophoresis tandem mass spectrometry: Recent developments in technology and applications," Electrophoresis 19:885–892.

Figeys, D., Ducret, A., Yates, J. R., and Aebersold, R. (1996), "Protein identification by solid phase microextraction-capillary zone electrophoresis-microelectrospray-tandem mass spectrometry," Nature Biotech. 14:1579–1583.

Figeys, D., Ning, Y., and Aebersold, R. (1997), "A microfabricated device for rapid protein identification by microelectrospray ion trap mass spectrometry," Anal. Chem. 69:3153–3160.

Garrels, J. I., McLaughlin, C. S., Warner, J. R., Futcher, B., Latter, G. I., Kobayashi, R., Schwender, B., Volpe, T., Anderson, D. S., Mesquita, F. R., and Payne, W. E. (1997), "Proteome studies of *Saccharomyces cerevisiae:* identification and characterization of abundant proteins. Electrophoresis," 18:1347–1360.

Gerber, S. A. et al. (1999), "Analysis of rates of multiple enzymes in cell lysates by electrospray ionization mass spectrometry," J. Am. Chem. Soc. 121:1102–1103.

Gygi, S. P. et al. (1999), "Correlation between portein and mRNA abundance in yeast," Mol. Cell. Biol. 19:1720–1730.

Gygi, S. P. et al. (1999), "Protein analysis by mass spectrometry and sequence database searching: tools for cancer research in the post-genomic era," Electrophoresis 20:310–319.

Haynes, P. A., Fripp, N., and Aebersold, R. (1998), "Identification of gel-separated proteins by liquid chromatography electrospray tandem mass spectrometry: Comparison of methods and their limitations," Electrophoresis 19:939–945.

Hodges, P. E. et al. (1999), "The Yeast Proteome Database (YPD): a model for the organization and presentation of genome-wide functional data," Nucl. Acids Res. 27:69–73.

Johnston, M. and Carlson, M. (1992), in *The Molecular and Cellular Biology of the Yeast Saccharomyces,* Johnes, E. W. et al. (eds.), Cold Spring Harbor Press, New York City, pp. 193–281

Link, A. J., Hays, L. G., Carmack, E. B., and Yates, J. R., 3rd (1997), "Identifying the major proteome components of *Haemophilus influenzae* type-strain NCTC 8143," Electrophoresis 18:1314–1334.

Link, J. et al. (1999), "Direct analysis of large protein complexes using mass spectrometry," Nat. Biotech. In press.

Mann, M., and Wilm, M. (1994), "Error-tolerant identification of peptides in sequence databases by peptide sequence tags," Anal. Chem. 66:4390–4399.

Morris, A. A. M. and Turnbull, D. M. (1994) Curr. Opin. Neurol. 7:535–541.

Neufeld, E. and Muenzer, J. (1995), "The mucopolysaccharidoses" In *The Metabolic and Molecular Bases of Inherited Disease,* Scriver, C. R. et al. (eds.) McGraw-Hill, New York, pp. 2465–2494.

Oda, Y. et al. (1999), "Accurate quantitation of protein expression and site-specific phosphorylation," Proc. Natl. Acad. Sci. USA 96:6591–6596.

Okada, S. and O'Brien, J. S. (1968) Science 160:10002.

Opiteck, G. J. et al. (1997), "Comprehensive on-line LC/LC/MS of proteins," Anal. Chem. 69:1518–1524.

Pennington, S. R., Wilkins, M. R., Hochstrasser, D. F., and Dunn, M. J. (1997), "Proteome analysis: From protein characterization to biological function," Trends Cell Bio. 7:168–173.

Qin, J. et al. (1997), "A strategy for rapid, high-confidence protein identification," Anal. Chem. 69:3995–4001.

Ronne, H. (1995), "Glucose repression in fungi," Trends Genet. 11:12–17.

Scriver, C. R. et al. (1995), *The Metabolic and Molecular Bases of Inherited Disease,* McGraw-Hill, New York.

Scriver, C. R. et al. (1995), *The Metabolic and Molecular Bases of Inherited Disease,* Scriver, C. R. et al. (eds.) McGraw-Hill, New York, pp. 1015–1076.

Sechi, S. and Chait, B. T. (1998), "Modification of cysteine residues by alkylation. A tool in peptide mapping and protein identification," Anal. Chem. 70:5150–5158.

Segal, S. and Berry, G. T. (1995), *The Metabolic and Molecular Bases of Inherited Disease,* Scriver, C. R. et al. (eds.), McGraw-Hill, New York, pp. 967–1000.

Romanowska, A. et al. (1994) Methods Enzymol. 242:90–101.

Roth, F. P. et al. (1998), "Finding DNA regulatory motifs within unaligned noncoding sequences clustered by whole-genome mRNA quantitation," Nat. Biotechnol. 16:939–945

Shalon, D., Smith, S. J., and Brown, P. O. (1996), "A DNA microarray system for analyzing complex DNA samples using two-color fluorescent probe hybridization," Genome Res. 6:639–645.

Shevchenko, A., Jensen, O. N., Podtelejnikov, A. V., Sagliocco, F., Wilm, M., Vorm, O., Mortensen, P., Shevchenko, A., Boucherie, H., and Mann, M. (1996), "Linking genome and proteome by mass spectrometry: large-scale identification of yeast proteins from two dimensional gels," Proc. Natl. Acad. Sci. U.S.A. 93:14440–14445.

Shevchenko, A., Wilm, M., Vorm, O., and Mann, M. (1996), "Mass spectrometric sequencing of proteins silver-stained polyacrylamide gels," Anal. Chem. 68:850–858.

Velculescu, V. E., Zhang, L., Zhou, W., Vogelstein, J., Basrai, M. A., Bassett, D. E., Jr., Hieter, P., Vogelstein, B., and Kinzler, K. W. (1997), "Characterization of the yeast transcriptome," Cell 88:243–251.

Wilbur, D. S. et al. (1997) Bioconjugate Chem. 8:572–584.

Yates, J. R. d., Eng, J. K., McCormack, A. L., and Schieltz, D. (1995), "Method to correlate tandem mass spectra of modified peptides to amino acid sequences in the protein database," Anal. Chem. 67:1426–1436.

Brockhausen, I.; Hull, E.; Hindsgaul, O.; Schachter, H.; Shah, R. N.; Michnick, S. W.; Carver, J. P. (1989) Control of glycoprotein synthesis. *J. Biol. Chem.* 264, 11211–11221.

Chapman, A.; Fujimoto, K.; Kornefeld, S. (1980) The primary glycosylation defect in class E Thy-1-negative mutant mouse lymphoma cells is an inability to synthesize dolichol-P-mannose. *J. Biol. Chem.* 255, 4441–4446.

Freeze, H. H. (1998) Disorders in protein glycosylation and potential therapy. *J. Pediatrics* 133, 593–600.

Freeze, H. H. (1999) Human glycosylation disorders and sugar supplement therapy. *Biochem. Biophys. Res. Commun.* 255, 189–193.

Gerber, S. A.; Scott, C. R.; Turecek, F.; Gelb, M. H. (1999) Analysis of rates of multiple enzymes in cell lysates by electrospray ionization mass spectrometry. *J. Am. Chem. Soc.* 121, 1102–1103.

Glaser, L. (1966) Phosphomannomutase from yeast. In *Meth. Enzymol.* Vol. VIII, Neufeld, E. F.; Ginsburg, V. Eds; Academic Press: New York 1966, pp. 183–185.

Kaur, K. J.; Hingsgaul, O. (1991) A simple synthesis of octyl 3,6-di-O-(α-D-mannopyranosyl)-β-D-manopyranoside and its use as an acceptor for the assay of N-acetylglucosaminetransferase I activity. *Glycoconjugate J.* 8, 90–94.

Kaur, K. J.; Alton, G.; Hindsgaul, O. (1991) Use of N-acetylglucosaminyltranserases I and II in the preparative synthesis of oligosaccharides. Carbohydr. Res. 210, 145–153.

Komer, C.; Knauer, R.; Holzbach, U.; Hanefeld, F.; Lehle, L.; von Figura, K. (1998) Carbohydrate-deficient glycoprotein syndrome type V: deficiency of dolichyl-P-Glc:Man9GlcNAc2-PP-dolichyl glucosyltransferase. *Proc Natl Acad Sci U.S.A.* 95, 13200–13205.

McMurry, J. E.; Kocovsky, P. (1984) A method for the palladium-catalyzed allylic oxidation of olefins. *Tetrahedron Lett.* 25, 4187–4190.

Paulsen, H.; Meinjohanns, E. (1992) Synthesis of modified oligosaccharides of N-glycoproteins intended for substrate specificity studies of N-acetylglucosaminyltransferases II-V *Tetrahedron Lett.* 33, 7327–7330.

Paulsen, H.; Meinjohanns, E.; Reck, F.; Brockhausen, I. (1993) Synthese von modifizierten Oligosacchariden der N-Glycoproteine zur Untersuchung der Spezifitat der N-Acetylglucosaminyltransferase II. *Liebigs Ann. Chem.* 721–735.

Preiss, J. (1966) GDP-mannose pyrophosphorylase from Arthrobacter. In *Meth. Enzymol.* Vol. VIII, Neufeld, E. F.; Ginsburg, V. Eds; Academic Press: New York 1966, pp. 271–275.

Ronin, C.; Caseti, C.; Bouchilloux, C. (1981) Transfer of glucose in the biosynthesis of thyroid glycoproteins. I. Inhibition of glucose transfer to oligosaccharide lipids by GDP-mannose. *Biochim. Biophys. Acta* 674, 48–57.

Ronin, C.; Granier, C.; Caseti, C.; Bouchilloux, S.; Van Rietschoten, J. (1981a) Synthetic substrates for thyroid oligosaccharide transferase. Effects of peptide chain length and modifications in the -Asn-Xaa-Thr-region. *Eur. J. Biochem.* 118, 159–164.

Rush, J. S.; Wachter, C. J. (1995) Transmembrane movement of a water-soluble analogue of mannosylphosphoryldolichol is mediated by an endoplasmic reticulum protein. *J. Cell. Biol.* 130, 529–536.

Schachter, H. (1986) Biosynthetic controls that determine the branching and microheterogeneity of protein-bound oligosaccharides. *Biochem. Cell Biol.* 64, 163–181.

Tan, J.; Dunn, J.; Jaeken, J.; Schachter, H. (1996) Mutations in the MGAT2 gene controlling complex glycan synthesis cause carbohydrate deficient glycoprotein syndrome type II, an autosomal recessive disease with defective brain development. *Am. J. Hum. Genet.* 59, 810–817.

We claim:

1. A method for identifying and determining the relative amounts of one or more proteins or protein functions in two or more samples containing mixtures of proteins which comprises the steps of:

(a) providing an affinity tagged, substantially chemically identical but isotopically distinguishable protein reactive reagent for each sample wherein the reagent has the formula:

A—L—PRG where A is an affinity label that selectively binds to a capture reagent, L is a linker group which is differentially labeled with one or more stable isotopes and PRG is a protein reactive group that selectively reacts with a protein functional group or is a substrate for an enzyme;

(b) reacting each sample with one of the protein reactive reagents to provide affinity tagged proteins or affinity tagged enzyme products in the sample, affinity tagged proteins or enzyme products in different samples being thereby differentially labeled with one or more stable isotopes;

(c) combining the differentially labeled samples;

(d) capturing affinity tagged differentially labeled proteins or affinity tagged differentially labeled enzyme products of the samples using the capture reagent that selectively binds A;

(e) releasing captured affinity tagged differentially labeled proteins or affinity tagged differentially labeled enzyme products from the capture reagent by disrupting the interaction between the affinity tagged differentially labeled proteins or affinity tagged differentially labeled enzyme products and the capture reagent;

(f) detecting and identifying the released affinity tagged differentially labeled proteins or affinity tagged differentially labeled enzyme products by mass spectrometry; and (g) measuring the relative amounts of the affinity tagged differentially labeled proteins, the relative amounts of the affinity tagged differentially labeled enzyme products or both.

2. The method of claim 1 wherein the affinity tagged proteins in the combined samples are digested or fragmented, before or after their capture, to convert them into affinity tagged peptides.

3. The method of claim 2 wherein one or more of the affinity tagged peptides are sequenced by tandem mass spectroscopy to identify the affinity tagged protein from which the peptide originated.

4. The method of claim 1 wherein a protein portion of one or more of the affinity tagged proteins is sequenced by tandam mass spectrometry to identify the protein.

5. The method of claim 1 in which the amount of one or more proteins in the samples is also determined by mass spectrometry and which further comprises the step of introducing into each of the two or more samples a known amount of one or more internal standards for each of the proteins to be quantitated.

6. The method of claim 5 wherein the internal standard is an affinity tagged differentially isotopically labeled peptide that is characteristic of a protein to be identified in each of the two or more samples.

7. The method of claim 5 wherein PRG is a protein reactive group that selectively reacts with protein functional groups of interest and a plurality of proteins are detected and identified in each of the samples.

8. The method of claim 1 wherein PRG is an enzyme substrate and the enzymatic velocities of one or more enzymes in a sample are determined by quantitation of affinity tagged enzyme products and which further comprises the step of introducing into each of the two or more samples a known amount of one or more internal standards for each of the affinity tagged enzyme products to be quantitated.

9. The method of claim 1 wherein the released affinity tagged proteins or affinity tagged enzyme products are separated by chromatography prior to detecting and identifying by mass spectrometry.

10. The method of claim 1 in which a plurality of proteins or protein functions in each samples are detected and identified.

11. The method of claim 1 further comprising a step in which one or more of the proteins in a sample are treated enzymatically or chemically to expose a protein functional group that can react with the protein reactive group of the protein reactive reagent.

12. The method of claim 1 wherein the PRG is an enzyme substrate for one or more enzymes, enzymatic deficiencies of which, are linked to a disease state.

13. The method of claim 1 wherein an affinity tagged, substantially chemically identical but isotopically distinguishable substrate is provided for each enzyme that is to be detected and identified in the two or more samples.

14. The method of claim 1 wherein PRG is a protein reactive group that selectively reacts with a protein functional group and a plurality of proteins containing that protein functional group are detected and identified in the two or more samples.

15. The method of claim 14 wherein two or more affinity tagged, substantially chemically identical but isotopically distinguishable protein reactive reagents having different specificities for reaction with proteins are provided and reacted with each sample to be analyzed.

16. The method of claim 15 wherein all of the proteins in each sample are detected and identified.

17. The method of claim 1 which determines relative amounts of membrane proteins in two or more different samples.

18. The method of claim 1 in which different samples contain proteins originating from different organelles or different subcellular fractions.

19. The method of claim 1 in which different samples represent proteins expressed in response to different environmental or nutritional conditions, different chemical or physical stimuli or at different times.

20. The method of claim 1 wherein one or more of the proteins or protein functions identified is associated with a birth defect.

21. The method of claim 1 wherein one or more of the proteins or protein functions identified is associated with a lysosomal storage disease.

22. The method of claim 1 wherein the samples are samples comprising cell surface proteins.

23. The method of claim 1 wherein the method identifies one or more marker proteins characteristic of a particular cell state.

24. The method of claim 1 wherein the reagent has the formula:

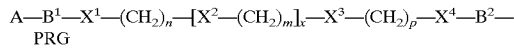

where:

A is the affinity label;

PRG is the protein reactive group; and $B^1-X^1-(CH_2)_n-[X^2-(CH_2)_m]_x-X^3-(CH_2)_p-X^4-B^2$ is the linker group wherein:

$X^1$, $X^2$, $X^3$ and $X^4$, independently of one another, and $X^2$ independently of other $X^2$, can be selected from O, S, NH, NR, NRR'$^+$, CO, COO, COS, S—S, SO, $SO_2$, CO—NR', CS—NR', Si—O, aryl and diaryl groups or $X^1$–$X^4$ may be absent;

$B^1$ and $B^2$, independently of one another, are optional groups selected from COO, CO, CO—NR', CS—NR', $(CH_2)_q$—CONR', $(CH_2)_q$—CS—NR', and $(CH_2)_q$;

n, m, p, q and x are whole numbers that can take values from 0 to about 100, where the sum of n+xm+p+q is less than about 100;

R is an alkyl, alkenyl, alkynyl, alkoxy or an aryl group that is optionally substituted with one or more alkyl, alkenyl, alkynyl, or alkoxy groups; and R' is a hydrogen, an alkyl, alkenyl, alkynyl, alkoxy or an aryl group that is optionally substituted with one or more alkyl, alkenyl, alkynyl, or alkoxy groups wherein one or more of the $CH_2$ groups in the linker can be optionally substituted with alkyl, alkenyl, alkoxy groups, an aryl group that is optionally substituted with one or more alkyl, alkenyl, alkynyl, or alkoxy groups, an acidic group, a basic group or a group carrying a permanent positive or negative charge; wherein one or more single bonds linking non-adjacent $CH_2$ groups in the linker can be replaced with a double or a triple bond and wherein one or more of the atoms in the linker is substituted with one or more stable isotopes.

25. The method of claim 24 wherein in the reagent at least one of $B^1$ or $B^2$ is CO—NR' or CS—NR.

26. The method of claim 24 wherein in the reagent $X^1$ and $X^4$ are selected from the group consisting of NH, NR, and NRR'$^+$, $X^3$ is O and all $X^2$ groups are O.

27. The method of claim 1 wherein the affinity label in the reagent is biotin or a modified biotin.

28. The method of claim 1 wherein the affinity label in the reagent is selected from the group consisting of a 1,2-diol, glutathione, maltose, a nitrilotriacetic acid group, and an oligohistidine.

29. The method of claim 1 wherein the affinity label in the reagent is a hapten.

30. The method of claim 1 wherein PRG of the reagent is a sulfhydryl-reactive group.

31. The method of claim 1 wherein PRG of the reagent is an iodoacetylamide group, an epoxide, an α-haloacyl group, a nitriles, a sulfonated alkyl, an aryl thiols or a maleimide.

32. The method of claim 1 wherein PRG of the reagent is an amine reactive group, a group that reacts with a homoserine lactone or a group that reacts with carboxylic acid group.

33. The method of claim 1 wherein PRG of the reagent is selected from the group consisting of an amine reactive pentafluorophenyl ester group, an amine reactive N-hydroxy succinimide ester group, a sulfonyl halide, an isocyanate, an isothiocyanate, an active ester, a tetrafluorophenyl ester, an acid halide, an acid anhydride, a homoserine lactone-reactive primary amine group, a carboxylic acid reactive amine, alcohols, and 2,3,5,6-tetrafluorophenyl trifluoroacetate.

34. The method of claim 1 wherein PRG of the reagent is a substrate for β-galactosidase, acetyl-α-D-glucosaminidase, heparan sulfamidase, acetyl-CoA-α-D-glucosaminide N-acetyltransferase or N-acetylglucosamine-6-sulfatase.

35. The method of claim 1 wherein in the reagent the linker group contains a disulfide group.

36. The method of claim 1 wherein in the reagent any atom of the linker group may be substituted with a heavy isotope.

37. The method of claim 1 wherein in the reagent the linker group is cleavable.

38. The method of claim 5 which determines the relative amounts of membrane proteins in two or more different samples.

39. The method of claim 5 in which different samples contain proteins originating from different organelles or different subcellular fractions.

40. The method of claim 5 in which different samples represent proteins expressed in response to different environmental or nutritional conditions, different chemical or physical stimuli or at different times.

41. The method of claim 5 wherein one or more of the proteins or protein functions identified is associated with a birth defect.

42. The method of claim 5 wherein one or more of the proteins or protein functions identified is associated with a lysosomal storage disease.

43. The method of claim 5 wherein the samples are samples comprising cell surface proteins.

44. The method of claim 5 wherein the method identifies one or more marker proteins characteristic of a particular cellular state.

45. The method of claim 5 wherein the internal standard is an affinity tagged differentially isotopically labeled peptide that is characteristic of a protein to be identified in each of the samples.

46. The method of claim 5 wherein the affinity label in the reagent is selected from the group consisting of a 1,2-diol, glutathione, maltose, a nitrilotriacetic acid group, an oligohistidine and a hapten.

47. The method of claim 5 wherein PRG of the reagent is a sulfhydryl reactive group.

48. The method of claim 5 wherein PRG of the protein reactive reagent is an iodoacetylamide group, an epoxide, an α-haloacyl group, a nitrites, a sulfonated alkyl, an aryl thiols or a maleimide.

49. The method of claim 5 wherein the linker group of the protein reactive reagent contains a disulfide group.

50. The method of claim 5 wherein in the reagent any atom of the linker may be substituted with a heavy isotope.

51. The method of claim 5 wherein in the reagent the linker is cleavable.

52. The method of claim 8 wherein enzyme velocities of one or more enzymes in each sample are determined by quantitation of affinity tagged enzyme products as a function of time.

53. The method of claim 8 wherein the PRG is an enzyme substrate for one or more enzymes, enzymatic deficiencies of which, are linked to a disease state.

54. The method of claim 8 wherein one or more of the proteins or protein functions identified is associated with a birth defect.

55. The method of claim 8 wherein an affinity tagged, substantially chemically identical and differentially isotopically labeled enzyme substrate is provided for each enzyme that is to be detected and identified in a sample.

56. The method of claim 8 wherein one or more of the proteins or protein functions identified is associated with a lysosomal storage disease.

57. The method of claim 8 wherein PRG of the reagent is a substrate for β galactosidase, acetyl α D glucosaminidase, heparin sulfamidase, acetyl CoA α D glucosaminide N acetyltransferase or N acetylglucosamine 6 sulfatase.

58. The method of claim 8 wherein the affinity label in the protein reactive reagent is biotin or a modified biotin.

59. The method of claim 8 wherein the affinity label in the protein reactive reagent is selected from the group consisting of a 1,2-diol, glutathione, maltose, a nitrilotriacetic acid group, an oligohistidine and a hapten.

60. The method of claim 8 wherein in the reagent the linker group contains a disulfide group.

61. The method of claim 8 wherein in the reagent any atom of the linker may be substituted with a heavy isotope.

62. The method of claim 8 wherein in the reagent the linker is cleavable.

63. A method for determining relative amounts of proteins in two or more samples containing proteins which comprises the steps of:

(a) providing an affinity tagged, substantially chemically identical but isotopically distinguishable labeled protein reactive reagent for each sample wherein the reagent has the formula:

$$A\text{—}L\text{—}PRG$$

where A is an affinity label that selectively binds to a capture reagent, L is a linker group which is differentially labeled with one or more stable isotopes and PRG is a protein reactive group that selectively reacts with a protein functional group;

(b) reacting each sample with one of the protein reactive reagents to provide affinity tagged proteins in the sample, affinity tagged proteins in different samples, being thereby differentially labeled with stable isotopes;

(c) combining the differentially labeled samples and treating the combined sample to cleave the proteins therein and to generate peptides;

(d) capturing affinity tagged differentially labeled peptides of the combined sample using the capture reagent that selectively binds A;

(e) releasing captured affinity tagged differentially labeled peptides from the capture reagent by disrupting the interaction between the affinity tagged differentially labeled peptides and the capture reagent;

(f) detecting and identifying the released affinity tagged differentially labeled peptides by mass spectrometry; and (g) measuring relative abundances of isotopically distinctions generated from each affinity tagged differentially labeled peptide to determine relative amounts of the protein from which the affinity tagged differentially labeled peptide originated.

64. The method of claim 63 further comprising adding a known amount of one or more internal standards to two or more of the samples to be analyzed.

65. The method of claim 64 wherein the internal standard is an affinity tagged differentially isotopically labeled peptide that is characteristic of a protein whose amount is to be determined.

66. The method of claim 63 wherein the two or more samples are samples comprising cell surface proteins.

67. The method of claim 66 wherein the method determines the relative expression levels of one or more marker proteins characteristic of a particular cellular state in the two or more samples comprising cell surface proteins.

68. The method of claim 63 wherein PRG of the reagent is a sulfhydryl-reactive group, an iodoacetylamide group, an epoxide, an α-haloacyl group, a nitrites, a sulfonated alkyl, an aryl thiol, a maleimide, an amine reactive group, a group that reacts with a homoserine lactone or a group that reacts with carboxylic acid group.

69. The method of claim 63 wherein in the reagent the linker group contains a disulfide group.

70. The method of claim 63 wherein in the reagent any atom of the linker group may be substituted with a heavy isotope.

71. The method of claim 63 wherein one or more of the proteins identified is associated with a birth defect.

72. The method of claim 63 wherein one or more of the proteins identified is associated with a lysosomal storage disease.

73. The method of claim 63 wherein the samples are samples comprising cell surface proteins.

74. The method of claim 63 wherein the method identifies one or more marker proteins characteristic of a particular cellular state.

75. The method of claim 63 wherein in the reagent the linker group contains a disulfide group.

76. The method of claim 63 wherein in the reagent any atom of the linker may be substituted with a heavy isotope.

77. The method of claim 63 wherein in the reagent the linker is cleavable.

78. A method for identifying one or more proteins or protein functions in two or more samples containing mixtures of proteins which comprises the steps of:

(a) providing an affinity tagged protein reactive reagent wherein the reagent has the formula:

where A is an affinity label that selectively binds to a capture reagent, L is a linker group which is differentially labeled with one or more stable isotopes and PRG is a protein reactive group that is a substrate for an enzyme;

(b) reacting each sample with the protein reactive reagent to provide affinity tagged differentially labeled enzyme products in each sample, (c) capturing the affinity tagged differentially labeled enzyme products of the samples using the capture reagent that selectively binds A;

(d) releasing the captured affinity tagged differentially labeled enzyme products from the capture reagent by disrupting the interaction between the affinity tagged differentially labeled enzyme products and the capture reagent; and (e) detecting and identifying the released affinity tagged differentially labeled enzyme products by mass spectrometry to identify one or more proteins or protein functions in the samples.

79. The method of claim 78 wherein an affinity tagged substantially chemically identical but isotopically distinguishable protein reactive agent is provided for each sample by differentially labeling the linker group of the protein reactive reagent with one or more stable isotopes.

80. A method for determining an enzyme velocity of one or more enzymes in two or more samples by quantitation of one or more affinity tagged products of the one or more enzymes in the sample which comprises the steps of:

(a) providing an affinity tagged protein reactive reagent wherein the reagent has the formula:

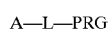

where A is an affinity label that selectively binds to a capture reagent, L is a linker group which is differentially labeled with one or more stable isotopes and PRG is a protein reactive group that is a substrate for an enzyme;

(b) reacting each sample with the protein reactive reagent to provide affinity tagged differentially labeled enzyme products in each sample, (c) introducing into each of the samples a known amount of one or more internal standards for each of the affinity tagged differentially labeled enzyme products to be quantitated, (d) capturing the affinity tagged differentially labeled enzyme products of each of the samples using the capture reagent that selectively binds A;

(e) releasing the captured affinity tagged differentially labeled enzyme products from the capture reagent by disrupting the interaction between the affinity tagged differentially labeled enzyme products and the capture reagent; and (f) identifying and quantitating the released affinity tagged differentially labeled enzyme products by mass spectrometry to determine the enzyme velocity of the one or more enzymes in the samples.

81. The method of claim 80 wherein one or more of the enzymes, the velocities of which are determined, is associated with a birth defect.

82. The method of claim 80 wherein the deficiency of one or more of the enzymes, the velocities of which are determined, is linked to a disease state.

83. The method of claim 78 wherein relative amounts of one or more proteins or protein functions in two or more different samples is also determined and which further comprises the steps of combining the differentially labeled samples, capturing affinity tagged differentially labeled enzyme products from the combined samples and measuring the relative amounts of the affinity tagged differentially labeled enzyme products in the different samples.

84. The method of claim 78 wherein PRG of the reagent is a substrate for β-galactosidase, acetyl-α-D- glucosaminidase, heparin sufamidase, acetyl-CoA-D-glucosaminide N-acetyltransferase or N-acetylglucosamine-6-sulfatase.

85. The method of claim 78 wherein PRG is an enzyme substrate for one or more enzymes, the deficiencies of which are linked to a disease state.

86. The method of claim 78 wherein one or more of the proteins or protein functions identified is associated with a lysosomal storage disease.

87. The method of claim 78 wherein one or more of the proteins or protein functions identified is associated with a birth defect.

88. The method of claim 78 wherein the affinity label in the protein reactive reagent is biotin or a modified biotin.

89. The method of claim 78 wherein the affinity label in the protein reactive reagent is selected from the group consisting of a 1,2-diol, glutathione, maltose, a nitriliotriacetic acid group, an oligohistidine and a hapten.

90. The method of claim 78 wherein the linker group in the protein reactive reagent contains a disulfide group.

91. The method of claim 78 wherein the linker group in the protein reactive reagent is cleavable.

92. The method of claim 78 wherein the linker group in the protein reactive group may be substituted with a heavy isotope.

93. The method of claim 78 wherein the reagent has the formula:

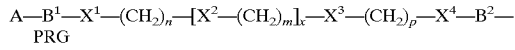

where:

A is the affinity label;

PRG is the enzyme substrate; and $B^1$—$X^1$—$(CH_2)_n$—$[X^2$—$(CH_2)_m]_x$—$X^3$—$(CH_2)_p$—$X^4$—$B^2$ is the linker group wherein:

$X^1$, $X^2$, $X^3$ and $X^4$, independently of one another, and $X^2$ independently of other $X^2$, can be selected from O, S, NH, NR, NRR'+, CO, COO, COS, S—S, SO, $SO_2$, CO—NR', CS—NR', Si—O, aryl and diaryl groups or $X^1$-$X^4$ may be absent;

$B^1$ and $B^2$, independently of one another, are optional groups selected from COO, CO, CO—NR', CS—NR', $(CH_2)_q$—CONR', $(CH_2)_q$13 CS—NR', and $(CH_2)_q$;

n, m, p, q and x are whole numbers that can take values from 0 to about 100, where the sum of n+xm+p+q is less than about 100;

R is an alkyl, alkenyl, alkynyl, alkoxy or an aryl group that is optionally substituted with one or more alkyl, alkenyl, alkynyl, or alkoxy groups; and R' is a hydrogen, an alkyl alkenyl, alkynyl, alkoxy or an aryl group that is optionally substituted with one or more alkyl, alkenyl, alkynyl, or alkoxy groups wherein one or more of the $CH_2$ groups in the linker can be optionally substituted with alkyl, alkenyl, alkoxy groups, an aryl group that is optionally substituted with one or more alkyl, alkenyl, alkynyl, or alkoxy groups, an acidic group, a basic group or a group carrying a permanent positive or negative charge; wherein one or more single bonds linking non-adjacent $CH_2$ groups in the linker can be replaced with a double or a triple bond and wherein one or more of the atoms in the linker is substituted with one or more stable isotopes.

94. The method of claim 93 wherein in the reagent at least one of $B^1$ or $B^2$ is CONR' or CSNR.

95. The method of claim 93 wherein in the reagent $X^1$ and $X^4$ are selected from the group consisting of NH, NR and NRR', $X^3$ is O and all $X^2$ groups are O.

96. The method of claim 93 wherein the affinity label in the reagent is biotin or a modified biotin.

* * * * *

UNITED STATES PATENT AND TRADEMARK OFFICE
CERTIFICATE OF CORRECTION

PATENT NO. : 6,670,194 B1
DATED : December 30, 2003
INVENTOR(S) : Aebersold et al.

It is certified that error appears in the above-identified patent and that said Letters Patent is hereby corrected as shown below:

Column 11,
Line 25, please delete "method herein to quantitative" and replace with -- methods herein to quantilate --.
Line 41, please delete "taggged" and replace with -- tagged --.

Column 16,
Line 29, please delete "corresponding the" and replace with -- corresponding to the --.
Line 61, please delete "invetion" and replace with -- invention --.

Column 19,
Line 20, please delete "procedure such as ID" and replace with -- procedures such as 1D --.
Line 51, please delete "tagged peptides tagged" and replace with -- peptides tagged --.
Line 66, please delete "spacer of capable" and replace with -- spacer capable --.

Column 20,
Line 7, please delete "with and".

Column 21,
Line 6, please delete "DOCH2CH2OCH2CH2OD with CD2" and replace with
-- $DOCH_2CH_2OCH_2CH_2OD$ with $CD_2$ --.
Line 11, please delete "CD2dCDCN in CH3CN" and replace with -- $CD_2dCDCN$ in $CH_3CN$ --.

Column 22,
Line 24, please delete "D-glucosamini-dase" and replace with -- D-glucosaminidase. --.
Line 30, please delete "mlz" and replace with -- m/z --.

Column 24,
Line 52, please delete "pyranosylphenylisothiocyanatecan" and replace with
-- "pyranosylphenylisothiocyanate can --.
Line 67, please delete "apreparative" and replace with -- a preparative --.

Column 26,
Line 9, please delete "20 û 30" and replace with -- 20 ~ 30 --.
Line 17, please delete "50 û 75" and replace with -- 50 ~ 75 --.
Line 22, please delete "4.5 N 6" and replace with -- 4.5 ~ 6 --.
Line 62, please delete "N20" and replace with -- ~20 --.

Column 28,
Line 49, please delete "-B-D" and replace with -- -β-D --.
Line 50, please delete "o-D" and replace with -- β-D --.

UNITED STATES PATENT AND TRADEMARK OFFICE
CERTIFICATE OF CORRECTION

PATENT NO. : 6,670,194 B1
DATED : December 30, 2003
INVENTOR(S) : Aebersold et al.

It is certified that error appears in the above-identified patent and that said Letters Patent is hereby corrected as shown below:

Column 29,
Line 14, please delete "CHC13/CH3OH" and replace with -- $CHCl_3/CH_3OH$ --.
Lines 20 and 62, please delete "H2O" and replace with -- $H_2O$ --.
Lines 46 and 48, please delete "H2" and replace with -- $H_2$ --.
Line 53, please delete "H20" and replace with -- $H_2O$ --.
Line 59, please delete "37?C" and replace with -- 37°C --.

Column 30,
Lines 9 and 17, please delete "H2O" and replace with -- $H_2O$ --.
Line 15, please delete "B-D" and replace with -- β-D --.
Line 34, please delete "(MgSO4)" and replace with -- $(MgSO_4)$ --.
Line 53, please delete [CaH$_z$]" and replace with -- $[CaH_2]$ --.

Column 31,
Line 18, please delete "(Na2SO4)" and replace with -- $(Na_2SO_4)$ --.
Line 45, please delete "N-B-D" and replace with -- N-β-D --.
Lines 49 and 60, please delete "-?-" and replace with -- -β- --.
Line 54, please delete both instances of "H2" and replace with -- $H_2$ --.

Column 32,
Lines 22 and 24, please delete both instances of "H2" and replace with -- $H_2$ --.
Lines 28 and 51, please delete "H2O" and replace with -$H_2O$ --.
Line 34, please delete "37?C" and replace with -- 37°C --.
Line 45, please delete "CHC13/CH3OH" and replace with -- $CHCl_3/CH_3OH$ --.

Column 33,
Lines 4 and 6, please delete both instances of "H2" and replace with -- $H_2$ --.
Lines 10, 20, 35, 43 and 66, please delete "H2O" and replace with -- $H_2O$ --.
Line 14, please delete "?-D" and replace with -- β-D --.
Line 28, please delete "CHC13/CH3OH" and replace with -- $CHCl_3/CH_3OH$ --.
Line 40, please delete "MgCl2" and replace with -- $MgCl_2$ --.
Line 41, please delete "?" and replace with -- β --.
Line 63, please delete "-20?C" and replace with -- -20°C --.

Column 34,
Lines 4 and 34, please delete "37?C" and replace with -- 37°C --.
Lines 8, 22, 38, and 52, please delete all instances of "H2O" and replace with -- $H_2O$ --.
Line 46, please delete "CHCl3/CH3OH" and replace with -- $CHCl_3/CH_3OH$ --.
Line 66, please delete "CHCl3" and replace with -- $CHCl_3$ --.

UNITED STATES PATENT AND TRADEMARK OFFICE
CERTIFICATE OF CORRECTION

PATENT NO.   : 6,670,194 B1                                              Page 3 of 4
DATED        : December 30, 2003
INVENTOR(S)  : Aebersold et al.

It is certified that error appears in the above-identified patent and that said Letters Patent is hereby corrected as shown below:

Column 35,
Line 1, please delete "CHCl3" and replace with -- $CHCl_3$ --.
Line 18, please delete both instances of "CHCl3/CH3OH" and replace with -- $CHCl_3/CH_3OH$ --.

Column 38,
Table 1, in the footnote please delete "4" and replace with -- $4^-$ --.

Column 37,
Table 2, in the footnote please delete "190" and replace with -- # --.

Column 43,
Table 4, under "Disease" about halfway down the column, please delete "and mut" and replace with -- and mut$^-$) --.
Table 4, under "Dysfunction" about halfway down the column, please delete "mut" and replace with -- mut$^-$ --.

Columns 67 and 68,
Please delete molecule 12 of Scheme 16 and replace with the following:

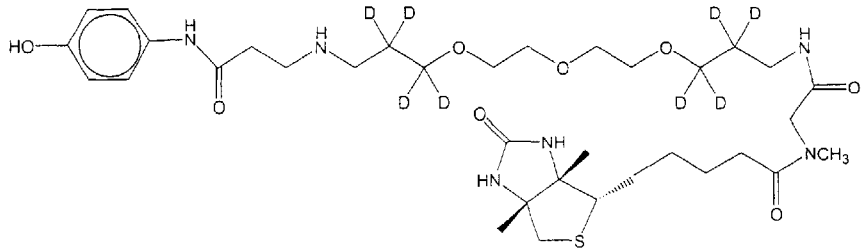

Column 71,
please delete molecule 38 of Scheme 22, and replace with the following:

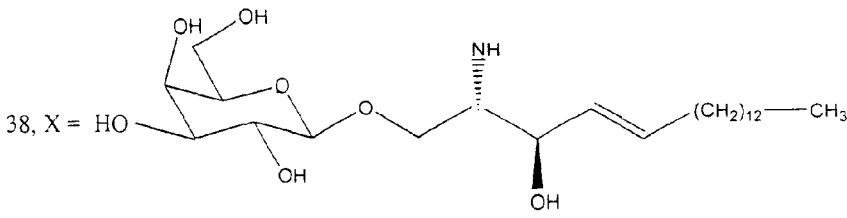

UNITED STATES PATENT AND TRADEMARK OFFICE
CERTIFICATE OF CORRECTION

PATENT NO. : 6,670,194 B1
DATED : December 30, 2003
INVENTOR(S) : Aebersold et al.

It is certified that error appears in the above-identified patent and that said Letters Patent is hereby corrected as shown below:

Column 105,
Line 42, please delete "samples" and replace with -- sample --.

Column 107,
Line 11, please delete "nitriles" and replace with -- nitrile --.
Line 11, please delete "thiols" and replace with -- thiol --.

Column 108,
Line 3, please delete "nitrites" and replace with -- nitrite --.
Line 3, please delete "thiols" and replace with -- thiol --.
Line 28, please delete "β galactosidase, acetyl α D plucosaminidase," and replace with -- β-galactosidase, acetyl-α-D-glucosaminidase, --.

Column 109,
Lines 8 and 9, please delete "distinc-tions" and replace with -- distinct ions --.
Line 27, please delete "nitrites" and replace with -- nitrile --.
Line 30, please insert --a-- between "with" and "carboxylic".

Column 112,
Line 8, please delete "$(CH_2)_q 13\ CS$" and replace with -- $(CH_2)_q—CS$ --.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,670,194 B1
DATED : December 30, 2003
INVENTOR(S) : Aebersold et al.

It is certified that error appears in the above-identified patent and that said Letters Patent is hereby corrected as shown below:

Column 11,
Line 25, please delete "method herein to quantitative" and replace with -- methods herein to quantitate --.
Line 41, please delete "taggged" and replace with -- tagged --.

Column 16,
Line 29, please delete "corresponding the" and replace with -- corresponding to the --.
Line 61, please delete "invetion" and replace with -- invention --.

Column 19,
Line 20, please delete "procedure such as ID" and replace with -- procedures such as 1D --.
Line 51, please delete "tagged peptides tagged" and replace with -- peptides tagged --.
Line 66, please delete "spacer of capable" and replace with -- spacer capable --.

Column 20,
Line 7, please delete "with and".

Column 21,
Line 6, please delete "DOCH2CH2OCH2CH2OD with CD2" and replace with
-- DOCH$_2$CH$_2$OCH$_2$CH$_2$OD with CD$_2$ --.
Line 11, please delete "CD2dCDCN in CH3CN" and replace with -- CD$_2$dCDCN in CH$_3$CN --.

Column 22,
Line 24, please delete "D-glucosamini-dase" and replace with -- D-glucosaminidase. --.
Line 30, please delete "mlz" and replace with -- m/z --.

Column 24,
Line 52, please delete "pyranosylphenylisothiocyanatecan" and replace with
-- "pyranosylphenylisothiocyanate can --.
Line 67, please delete "apreparative" and replace with -- a preparative --.

Column 26,
Line 9, please delete "20 û 30" and replace with -- 20 ~ 30 --.
Line 17, please delete "50 û 75" and replace with -- 50 ~ 75 --.
Line 22, please delete "4.5 N 6" and replace with -- 4.5 ~ 6 --.
Line 62, please delete "N20" and replace with -- ~20 --.

Column 28,
Line 49, please delete "-B-D" and replace with -- -β-D --.
Line 50, please delete "o-D" and replace with -- β-D --.

UNITED STATES PATENT AND TRADEMARK OFFICE
CERTIFICATE OF CORRECTION

PATENT NO. : 6,670,194 B1
DATED : December 30, 2003
INVENTOR(S) : Aebersold et al.

It is certified that error appears in the above-identified patent and that said Letters Patent is hereby corrected as shown below:

Column 29,
Line 14, please delete "CHC13/CH3OH" and replace with -- $CHCl_3/CH_3OH$ --.
Lines 20 and 62, please delete "H2O" and replace with -- $H_2O$ --.
Lines 46 and 48, please delete "H2" and replace with -- $H_2$ --.
Line 53, please delete "H20" and replace with -- $H_2O$ --.
Line 59, please delete "37?C" and replace with -- $37°C$ --.

Column 30,
Lines 9 and 17, please delete "H2O" and replace with -- $H_2O$ --.
Line 15, please delete "B-D" and replace with -- $\beta$-D --.
Line 34, please delete "(MgSO4)" and replace with -- $(MgSO_4)$ --.
Line 53, please delete [CaH$_z$]" and replace with -- $[CaH_2]$ --.

Column 31,
Line 18, please delete "(Na2SO4)" and replace with -- $(Na_2SO_4)$ --.
Line 45, please delete "N-B-D" and replace with -- N-$\beta$-D --.
Lines 49 and 60, please delete "-?-" and replace with -- -$\beta$- --.
Line 54, please delete both instances of "H2" and replace with -- $H_2$ --.

Column 32,
Lines 22 and 24, please delete both instances of "H2" and replace with -- $H_2$ --.
Lines 28 and 51, please delete "H2O" and replace with -$H_2O$ --.
Line 34, please delete "37?C" and replace with -- $37°C$ --.
Line 45, please delete "CHC13/CH3OH" and replace with -- $CHCl_3/CH_3OH$ --.

Column 33,
Lines 4 and 6, please delete both instances of "H2" and replace with -- $H_2$ --.
Lines 10, 20, 35, 43 and 66, please delete "H2O" and replace with -- $H_2O$ --.
Line 14, please delete "?-D" and replace with -- $\beta$-D --.
Line 28, please delete "CHC13/CH3OH" and replace with -- $CHCl_3/CH_3OH$ --.
Line 40, please delete "MgCl2" and replace with -- $MgCl_2$ --.
Line 41, please delete "?" and replace with -- $\beta$ --.
Line 63, please delete "-20?C" and replace with -- $-20°C$ --.

Column 34,
Lines 4 and 34, please delete "37?C" and replace with -- $37°C$ --.
Lines 8, 22, 38, and 52, please delete all instances of "H2O" and replace with -- $H_2O$ --.
Line 46, please delete "CHCl3/CH3OH" and replace with -- $CHCl_3/CH_3OH$ --.
Line 66, please delete "CHCl3" and replace with -- $CHCl_3$ --.

UNITED STATES PATENT AND TRADEMARK OFFICE
CERTIFICATE OF CORRECTION

PATENT NO. : 6,670,194 B1
DATED : December 30, 2003
INVENTOR(S) : Aebersold et al.

It is certified that error appears in the above-identified patent and that said Letters Patent is hereby corrected as shown below:

Column 35,
Line 1, please delete "CHCl3" and replace with -- $CHCl_3$ --.
Line 18, please delete both instances of "CHCl3/CH3OH" and replace with -- $CHCl_3/CH_3OH$ --.

Column 38,
Table 1, in the footnote please delete "4" and replace with -- $4^-$ --.

Column 37,
Table 2, in the footnote please delete "190" and replace with -- # --.

Column 43,
Table 4, under "Disease" about halfway down the column, please delete "and mut" and replace with -- and $mut^-$) --.
Table 4, under "Dysfunction" about halfway down the column, please delete "mut" and replace with -- $mut^-$ --.

Columns 67 and 68,
Please delete molecule 12 of Scheme 16 and replace with the following:

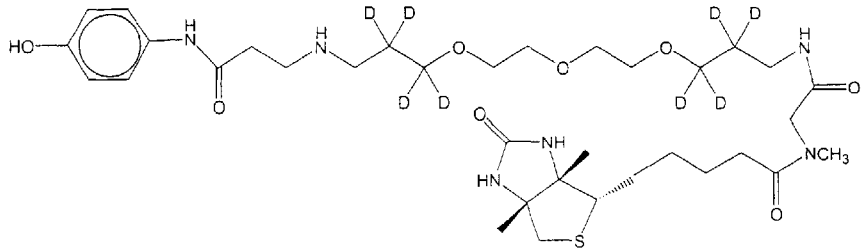

Column 71,
please delete molecule 38 of Scheme 22, and replace with the following:

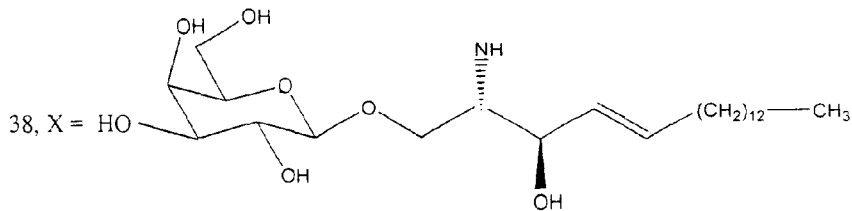

UNITED STATES PATENT AND TRADEMARK OFFICE
CERTIFICATE OF CORRECTION

PATENT NO.     : 6,670,194 B1
DATED          : December 30, 2003
INVENTOR(S)    : Aebersold et al.

It is certified that error appears in the above-identified patent and that said Letters Patent is hereby corrected as shown below:

Column 105,
Line 42, please delete "samples" and replace with -- sample --.

Column 107,
Line 11, please delete "nitriles" and replace with -- nitrile --.
Line 11, please delete "thiols" and replace with -- thiol --.

Column 108,
Line 3, please delete "nitrites" and replace with -- nitrite --.
Line 3, please delete "thiols" and replace with -- thiol --.
Line 28, please delete "β galactosidase, acetyl α D plucosaminidase," and replace with -- β-galactosidase, acetyl-α-D-glucosaminidase, --.

Column 109,
Lines 8 and 9, please delete "distinc-tions" and replace with -- distinct ions --.
Line 27, please delete "nitrites" and replace with -- nitrile --.
Line 30, please insert --a-- between "with" and "carboxylic".

Column 112,
Line 8, please delete "$(CH_2)_q 13$ CS" and replace with -- $(CH_2)_q$—CS --.

This certificate supersedes Certificate of Correction issued August 24, 2004.

Signed and Sealed this

Seventh Day of December, 2004

JON W. DUDAS
*Director of the United States Patent and Trademark Office*

```
                          SEQUENCE LISTING

<160> NUMBER OF SEQ ID NOS:   64

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:
      Heptapeptide motif found in substrates for glycosylation

<400> SEQUENCE: 1

Tyr Gln Ser Asn Ser Thr Met
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:  Test
      peptide

<400> SEQUENCE: 2

Lys Ala Leu Cys Ser Glu Lys
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Test
      peptide

<400> SEQUENCE: 3

Lys Cys Glu Val Phe Arg
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Test
      peptide

<400> SEQUENCE: 4

Lys Leu Asp Gln Trp Leu Cys Glu Lys
 1               5

<210> SEQ ID NO 5
<211> LENGTH: 15
<212> TYPE: PRT
```

```
<213> ORGANISM: Artificial Sequence
<220> FEATURE:
<223> OTHER INFORMATION: Description of Artificial Sequence: Test
      peptide

<400> SEQUENCE: 5

Lys Phe Leu Asp Asp Asp Leu Thr Asp Asp Ile Met Cys Val Lys
  1               5                  10                  15

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Test
      peptide

<400> SEQUENCE: 6

Lys Asp Asp Gln Asn Pro His Ser Ser Asn Ile Cys Asn Ile Ser Cys
  1               5                  10                  15

Asp Lys

<210> SEQ ID NO 7
<211> LENGTH: 43
<212> TYPE: PRT
<213> ORGANISM: Artificial Sequence
<220> FEATURE:
<223> OTHER INFORMATION: Description of Artificial Sequence: Test
      peptide

<400> SEQUENCE: 7

Lys Gly Tyr Gly Gly Val Ser Leu Pro Glu Trp Val Cys Thr Thr Phe
  1               5                  10                  15

His Thr Ser Gly Tyr Asp Thr Gln Ala Ile Val Gln Asn Asn Asp Ser
             20                  25                  30

Thr Glu Tyr Gly Leu Phe Gln Ile Asn Asn Lys
             35                  40

<210> SEQ ID NO 8
<211> LENGTH: 6
<212> TYPE: PRT
<213> ORGANISM: bovine
<220> FEATURE:
<221> NAME/KEY: VARIANT
<222> LOCATION: (3)
<223> OTHER INFORMATION: C at position 3 is ICAT- labeled cysteinyl
      residue

<400> SEQUENCE: 8

Ala Leu Cys Ser Glu Lys
  1               5

<210> SEQ ID NO 9
<211> LENGTH: 13
<212> TYPE: PRT
<213> ORGANISM: bovine
<220> FEATURE:
<221> NAME/KEY: VARIANT
<222> LOCATION: (11)
<223> OTHER INFORMATION: C at position 11 is ICAT-labeled cysteinyl
      residue.

<400> SEQUENCE: 9

Phe Leu Asp Asp Leu Thr Asp Asp Ile Met Cys Val Lys
  1               5                  10
```

```
<210> SEQ ID NO 10
<211> LENGTH: 10
<212> TYPE: PRT
<213> ORGANISM: chicken
<220> FEATURE:
<221> NAME/KEY: VARIANT
<222> LOCATION: (8)
<223> OTHER INFORMATION: C at position 8 is ICAT-labeled cysteinyl
      residue.

<400> SEQUENCE: 10

Ala Asp His Pro Phe Leu Phe Cys Ile Lys
 1               5                  10

<210> SEQ ID NO 11
<211> LENGTH: 12
<212> TYPE: PRT
<213> ORGANISM: chicken
<220> FEATURE:
<221> NAME/KEY: VARIANT
<222> LOCATION: (10)
<223> OTHER INFORMATION: C at position 10 is ICAT labeled cysteinyl
      residue.

<400> SEQUENCE: 11

Tyr Pro Ile Leu Pro Glu Tyr Leu Gln Cys Val Lys
 1               5                  10

<210> SEQ ID NO 12
<211> LENGTH: 8
<212> TYPE: PRT
<213> ORGANISM: E coli
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 12

Leu Thr Ala Ala Cys Phe Asp Arg
 1               5

<210> SEQ ID NO 13
<211> LENGTH: 13
<212> TYPE: PRT
<213> ORGANISM: E coli
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 13

Ile Gly Leu Asn Cys Gln Leu Ala Gln Val Ala Glu Arg
 1               5                  10

<210> SEQ ID NO 14
<211> LENGTH: 17
<212> TYPE: PRT
<213> ORGANISM: E coli
<220> FEATURE:
<221> NAME/KEY: VARIANT
<222> LOCATION: (14)
<223> OTHER INFORMATION: C at position 14 is ICAT-labeled cysteinyl
      residue.

<400> SEQUENCE: 14

Ile Ile Phe Asp Gly Val Asn Ser Ala Phe His Leu Trp Cys Asn Gly
 1               5                  10                  15
```

Arg

<210> SEQ ID NO 15
<211> LENGTH: 9
<212> TYPE: PRT
<213> ORGANISM: bovine
<220> FEATURE:
<221> NAME/KEY: VARIANT
<222> LOCATION: (6)
<223> OTHER INFORMATION: C at position 6 is ICAT-labeled cysteinyl
      residue.

<400> SEQUENCE: 15

Trp Glu Asn Gly Glu Cys Ala Gln Lys
 1               5

<210> SEQ ID NO 16
<211> LENGTH: 14
<212> TYPE: PRT
<213> ORGANISM: bovine
<220> FEATURE:
<221> NAME/KEY: VARIANT
<222> LOCATION: (12)
<223> OTHER INFORMATION: C at position 12 is ICAT-labeled cysteinyl
      residue.

<400> SEQUENCE: 16

Leu Ser Phe Asn Pro Thr Gln Leu Glu Glu Gln Cys His Ile
 1               5                  10

<210> SEQ ID NO 17
<211> LENGTH: 14
<212> TYPE: PRT
<213> ORGANISM: rabbit
<220> FEATURE:
<221> NAME/KEY: VARIANT
<222> LOCATION: (13)
<223> OTHER INFORMATION: C at position 13 is ICAT-labeled cysteinyl
      residue.

<400> SEQUENCE: 17

Val Pro Thr Pro Asn Val Ser Val Val Asp Leu Thr Cys Arg
 1               5                  10

<210> SEQ ID NO 18
<211> LENGTH: 17
<212> TYPE: PRT
<213> ORGANISM: rabbit
<220> FEATURE:
<221> NAME/KEY: VARIANT
<222> LOCATION: (1)..(17)
<223> OTHER INFORMATION: C at positions 7 and 11 are ICAT-labeled
      cysteinyl residues.

<400> SEQUENCE: 18

Ile Val Ser Asn Ala Ser Cys Thr Thr Asn Cys Leu Ala Pro Leu Ala
 1               5                  10                  15

Lys

<210> SEQ ID NO 19
<211> LENGTH: 15
<212> TYPE: PRT
<213> ORGANISM: rabbit
<220> FEATURE:
<221> NAME/KEY: VARIANT
<222> LOCATION: (2)
<223> OTHER INFORMATION: C at position 2 is ICAT-labeled cysteinyl
      residue.

```
<400> SEQUENCE: 19

Ile Cys Gly Gly Trp Gln Met Glu Glu Ala Asp Asp Trp Leu Arg
 1               5                  10                  15

<210> SEQ ID NO 20
<211> LENGTH: 16
<212> TYPE: PRT
<213> ORGANISM: rabbit
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 20

Thr Cys Ala Tyr Thr Asn His Thr Val Leu Pro Glu Ala Leu Glu Arg
 1               5                  10                  15

<210> SEQ ID NO 21
<211> LENGTH: 16
<212> TYPE: PRT
<213> ORGANISM: rabbit
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 21

Trp Leu Val Leu Cys Asn Pro Gly Leu Ala Glu Ile Ile Ala Glu Arg
 1               5                  10                  15

<210> SEQ ID NO 22
<211> LENGTH: 12
<212> TYPE: PRT
<213> ORGANISM: yeast
<220> FEATURE:
<221> NAME/KEY: VARIANT
<222> LOCATION: (4)
<223> OTHER INFORMATION: C at position 4 is ICAT-labeled cysteinyl
      residue.

<400> SEQUENCE: 22

Lys His Asn Cys Leu His Glu Pro His Met Leu Lys
 1               5                  10

<210> SEQ ID NO 23
<211> LENGTH: 21
<212> TYPE: PRT
<213> ORGANISM: yeast
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 23

Tyr Ser Gly Val Cys His Thr Asp Leu His Ala Trp His Gly Asp Trp
 1               5                  10                  15

Pro Leu Pro Val Lys
                20

<210> SEQ ID NO 24
<211> LENGTH: 11
<212> TYPE: PRT
<213> ORGANISM: yeast
<220> FEATURE:
<221> NAME/KEY: VARIANT
```

```
<222> LOCATION: (1)..(2)
<223> OTHER INFORMATION: C at positions 1 and 2 are ICAT-labeled
      cysteinyl residues.

<400> SEQUENCE: 24

Cys Cys Ser Asp Val Phe Asn Gln Val Val Lys
  1               5                  10

<210> SEQ ID NO 25
<211> LENGTH: 21
<212> TYPE: PRT
<213> ORGANISM: yeast
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 25

Tyr Ser Gly Val Cys His Thr Asp Leu His Ala Trp His Gly Asp Trp
  1               5                  10                  15

Pro Leu Pro Thr Lys
            20

<210> SEQ ID NO 26
<211> LENGTH: 11
<212> TYPE: PRT
<213> ORGANISM: yeast
<220> FEATURE:
<221> NAME/KEY: VARIANT
<222> LOCATION: (1)
<223> OTHER INFORMATION: C at position 1 is ICAT-labeled cysteinyl
      residue.

<400> SEQUENCE: 26

Cys Ser Ser Asp Val Phe Asn His Val Val Lys
  1               5                  10

<210> SEQ ID NO 27
<211> LENGTH: 20
<212> TYPE: PRT
<213> ORGANISM: yeast
<220> FEATURE:
<221> NAME/KEY: VARIANT
<222> LOCATION: (14)
<223> OTHER INFORMATION: C at position 14 is ICAT-labeled cysteinyl
      residue.

<400> SEQUENCE: 27

Thr Phe Glu Val Ile Asn Pro Ser Thr Glu Glu Glu Ile Cys His Ile
  1               5                  10                  15

Tyr Glu Gly Arg
            20

<210> SEQ ID NO 28
<211> LENGTH: 12
<212> TYPE: PRT
<213> ORGANISM: yeast
<220> FEATURE:
<221> NAME/KEY: VARIANT
<222> LOCATION: (9)
<223> OTHER INFORMATION: C at position 9 is ICAT-labeled cysteinyl
      residue.

<400> SEQUENCE: 28

Ser Glu His Gln Val Glu Leu Ile Cys Ser Tyr Arg
  1               5                  10
```

<210> SEQ ID NO 29
<211> LENGTH: 12
<212> TYPE: PRT
<213> ORGANISM: yeast
<220> FEATURE:
<221> NAME/KEY: VARIANT
<222> LOCATION: (5)
<223> OTHER INFORMATION: C at position 9 is ICAT-labeled cysteinyl
      residue.

<400> SEQUENCE: 29

Tyr Arg Pro Asn Cys Pro Ile Ile Leu Val Thr Arg
 1               5                  10

<210> SEQ ID NO 30
<211> LENGTH: 25
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 30

Asn Cys Thr Pro Lys Pro Thr Ser Thr Thr Glu Thr Val Ala Ala Ser
 1               5                  10                  15

Ala Val Ala Ala Val Phe Glu Gln Lys
            20                  25

<210> SEQ ID NO 31
<211> LENGTH: 19
<212> TYPE: PRT
<213> ORGANISM: yeast
<220> FEATURE:
<221> NAME/KEY: VARIANT
<222> LOCATION: (17)
<223> OTHER INFORMATION: C at position 17 is ICAT-labeled cysteinyl
      residue.

<400> SEQUENCE: 31

Ser Ile Ala Pro Ala Tyr Gly Ile Pro Val Val Leu His Ser Asp His
 1               5                  10                  15

Cys Ala Lys

<210> SEQ ID NO 32
<211> LENGTH: 6
<212> TYPE: PRT
<213> ORGANISM: yeast
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 32

Glu Gln Val Gly Cys Lys
 1               5

<210> SEQ ID NO 33
<211> LENGTH: 24
<212> TYPE: PRT
<213> ORGANISM: yeast
<220> FEATURE:
<221> NAME/KEY: VARIANT
<222> LOCATION: (9)
<223> OTHER INFORMATION: C at position 9 is ICAT-labeled cysteinyl
      residue.

<400> SEQUENCE: 33

Leu Thr Gly Ala Gly Trp Gly Cys Thr Val His Leu Val Pro Gly
 1               5                  10                  15
Gly Pro Asn Gly Asn Ile Glu Lys
             20

<210> SEQ ID NO 34
<211> LENGTH: 13
<212> TYPE: PRT
<213> ORGANISM: yeast
<220> FEATURE:
<221> NAME/KEY: VARIANT
<222> LOCATION: (11)
<223> OTHER INFORMATION: C at position 11 is ICAT-labeled cysteinyl
      residue.

<400> SEQUENCE: 34

His His Ile Pro Phe Tyr Glu Val Asp Leu Cys Asp Arg
 1               5                  10

<210> SEQ ID NO 35
<211> LENGTH: 6
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 35

Asp Cys Val Thr Leu Lys
 1               5

<210> SEQ ID NO 36
<211> LENGTH: 18
<212> TYPE: PRT
<213> ORGANISM: yeast
<220> FEATURE:
<221> NAME/KEY: VARIANT
<222> LOCATION: (3)
<223> OTHER INFORMATION: C at position 3 is ICAT-labeled cysteinyl
      residue.

<400> SEQUENCE: 36

Leu Trp Cys Thr Gln His His Glu Pro Glu Val Ala Leu Asp Gln Ser
 1               5                  10                  15
Leu Lys

<210> SEQ ID NO 37
<211> LENGTH: 18
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT labeled cysteinyl
      residue.

<400> SEQUENCE: 37

Ile Cys Ser Val Asn Leu His Gly Asp His Thr Phe Ser Met Glu Gln
 1               5                  10                  15
Met Lys

<210> SEQ ID NO 38

```
<211> LENGTH: 6
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 38

Ile Cys Ser Gln Leu Lys
 1               5

<210> SEQ ID NO 39
<211> LENGTH: 9
<212> TYPE: PRT
<213> ORGANISM: yeast
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 39

Gly Gly Thr Gln Cys Ser Ile Met Arg
 1               5

<210> SEQ ID NO 40
<211> LENGTH: 30
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 40

Asn Cys Phe Pro His His Gly Tyr Ile His Asn Tyr Gly Ala Phe Pro
 1               5                  10                  15

Gln Thr Trp Glu Asp Pro Asn Val Ser His Pro Glu Thr Lys
             20                  25                  30

<210> SEQ ID NO 41
<211> LENGTH: 13
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 41

Val Cys His Ala His Pro Thr Leu Ser Glu Ala Phe Lys
 1               5                  10

<210> SEQ ID NO 42
<211> LENGTH: 14
<212> TYPE: PRT
<213> ORGANISM: yeast
<220> FEATURE:
<221> NAME/KEY: VARIANT
<222> LOCATION: (11)
<223> OTHER INFORMATION: C at position 11 is ICAT-labeled cysteinyl
      residue.

<400> SEQUENCE: 42

Lys Gly Trp Thr Gly Gln Tyr Thr Leu Asp Cys Asn Thr Arg
```

```
                1               5                  10
```

```
<210> SEQ ID NO 43
<211> LENGTH: 10
<212> TYPE: PRT
<213> ORGANISM: yeast
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 43

Ser Val Val Leu Cys Asn Ser Thr Ile Lys
  1               5                  10

<210> SEQ ID NO 44
<211> LENGTH: 23
<212> TYPE: PRT
<213> ORGANISM: yeast
<220> FEATURE:
<221> NAME/KEY: VARIANT
<222> LOCATION: (1)
<223> OTHER INFORMATION: C at position 1 is ICAT-labeled cysteinyl
      residue.

<400> SEQUENCE: 44

Cys Thr Gly Gly Ile Ile Leu Thr Ala Ser His Asn Pro Gly Gly Pro
  1               5                  10                  15

Glu Asn Asp Met Gly Ile Lys
            20

<210> SEQ ID NO 45
<211> LENGTH: 17
<212> TYPE: PRT
<213> ORGANISM: yeast
<220> FEATURE:
<221> NAME/KEY: VARIANT
<222> LOCATION: (4)
<223> OTHER INFORMATION: C at position 4 is ICAT-labeled cysteinyl
      residue.

<400> SEQUENCE: 45

Leu Ser Ile Cys Gly Glu Glu Ser Phe Gly Thr Gly Ser Asn His Val
  1               5                  10                  15

Arg

<210> SEQ ID NO 46
<211> LENGTH: 10
<212> TYPE: PRT
<213> ORGANISM: yeast
<220> FEATURE:
<221> NAME/KEY: VARIANT
<222> LOCATION: (3)
<223> OTHER INFORMATION: C at position 3 is ICAT-labeled cysteinyl
      residue.

<400> SEQUENCE: 46

Ile Pro Cys Leu Ala Asp Ser His Pro Lys
  1               5                  10

<210> SEQ ID NO 47
<211> LENGTH: 17
<212> TYPE: PRT
<213> ORGANISM: yeast
<220> FEATURE:
<221> NAME/KEY: VARIANT
<222> LOCATION: (1)
```

```
<223> OTHER INFORMATION: C at position 1 is ICAT-labeled cysteinyl
      residue.

<400> SEQUENCE: 47

Cys Ile Asn Leu Ser Ala Glu Lys Glu Pro Glu Ile Phe Asp Ala Ile
 1               5                  10                  15

Lys

<210> SEQ ID NO 48
<211> LENGTH: 12
<212> TYPE: PRT
<213> ORGANISM: Yeast
<220> FEATURE:
<221> NAME/KEY: VARIANT
<222> LOCATION: (1)
<223> OTHER INFORMATION: C at position 1 is ICAT-labeled cysteinyl
      residue.

<400> SEQUENCE: 48

Cys Ala Tyr Pro Ile Asp Tyr Ile Pro Ser Ala Lys
 1               5                  10

<210> SEQ ID NO 49
<211> LENGTH: 23
<212> TYPE: PRT
<213> ORGANISM: yeast
<220> FEATURE:
<221> NAME/KEY: VARIANT
<222> LOCATION: (20)
<223> OTHER INFORMATION: C at position 20 is ICAT-labeled cysteinyl
      residue.

<400> SEQUENCE: 49

Ile Val Glu Glu Pro Thr Ser Lys Asp Glu Ile Trp Trp Gly Pro Val
 1               5                  10                  15

Asn Lys Pro Cys Ser Glu Arg
                20

<210> SEQ ID NO 50
<211> LENGTH: 12
<212> TYPE: PRT
<213> ORGANISM: yeast
<220> FEATURE:
<221> NAME/KEY: VARIANT
<222> LOCATION: (9)
<223> OTHER INFORMATION: C at position 9 is ICAT-labeled cysteinyl
      residue.

<400> SEQUENCE: 50

Ala Leu Val His His Tyr Glu Glu Cys Ala Glu Arg
 1               5                  10

<210> SEQ ID NO 51
<211> LENGTH: 14
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 51

Ser Cys Gly Val Asp Ala Met Ser Val Asp Asp Leu Lys Lys
 1               5                  10

<210> SEQ ID NO 52
```

```
<211> LENGTH: 24
<212> TYPE: PRT
<213> ORGANISM: yeast
<220> FEATURE:
<221> NAME/KEY: VARIANT
<222> LOCATION: (8)
<223> OTHER INFORMATION: C at position 8 is ICAT-labeled cysteinyl
      residue.

<400> SEQUENCE: 52

His Pro Glu Met Leu Glu Asp Cys Phe Gly Leu Ser Glu Glu Thr Thr
 1               5                  10                  15

Thr Gly Val His His Leu Tyr Arg
             20

<210> SEQ ID NO 53
<211> LENGTH: 11
<212> TYPE: PRT
<213> ORGANISM: yeast
<220> FEATURE:
<221> NAME/KEY: VARIANT
<222> LOCATION: (2)
<223> OTHER INFORMATION: C at position 2 is ICAT-labeled cysteinyl
      residue.

<400> SEQUENCE: 53

Glu Cys Ile Asn Ile Lys Pro Gln Val Asp Arg
 1               5                  10

<210> SEQ ID NO 54
<211> LENGTH: 25
<212> TYPE: PRT
<213> ORGANISM: yeast
<220> FEATURE:
<221> NAME/KEY: VARIANT
<222> LOCATION: (14)
<223> OTHER INFORMATION: C at position 14 is ICAT-labeled cysteinyl
      residue.

<400> SEQUENCE: 54

Gly Phe His Ile His Glu Phe Gly Asp Ala Thr Asn Gly Cys Val Ser
 1               5                  10                  15

Ala Gly Pro His Phe Asn Pro Phe Lys
             20                  25

<210> SEQ ID NO 55
<211> LENGTH: 9
<212> TYPE: PRT
<213> ORGANISM: yeast
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 55

Arg Gly Asn Val Cys Gly Asp Ala Lys
 1               5

<210> SEQ ID NO 56
<211> LENGTH: 6
<212> TYPE: PRT
<213> ORGANISM: yeast
<220> FEATURE:
<221> NAME/KEY: VARIANT
<222> LOCATION: (1)
<223> OTHER INFORMATION: C at position 1 is ICAT-labeled cysteinyl
      residue.
```

```
<400> SEQUENCE: 56

Cys Gly Gly Ile Asp Lys
 1               5

<210> SEQ ID NO 57
<211> LENGTH: 20
<212> TYPE: PRT
<213> ORGANISM: yeast
<220> FEATURE:
<221> NAME/KEY: VARIANT
<222> LOCATION: (8)
<223> OTHER INFORMATION: C at position 8 is ICAT-labeled cysteinyl
      residue.

<400> SEQUENCE: 57

Phe Val Pro Ser Lys Pro Met Cys Val Glu Ala Phe Ser Glu Tyr Pro
 1               5                  10                  15

Pro Leu Gly Arg
            20

<210> SEQ ID NO 58
<211> LENGTH: 20
<212> TYPE: PRT
<213> ORGANISM: yeast
<220> FEATURE:
<221> NAME/KEY: VARIANT
<222> LOCATION: (19)
<223> OTHER INFORMATION: C at position 19 is ICAT-labeled cysteinyl
      residue.

<400> SEQUENCE: 58

Ile Pro Ile Phe Ser Ala Ser Gly Leu Pro His Asn Glu Ile Ala Ala
 1               5                  10                  15

Gln Ile Cys Arg
            20

<210> SEQ ID NO 59
<211> LENGTH: 10
<212> TYPE: PRT
<213> ORGANISM: yeast
<220> FEATURE:
<221> NAME/KEY: VARIANT
<222> LOCATION: (5)
<223> OTHER INFORMATION: C at position 5 is ICAT-labeled cysteinyl
      residue.

<400> SEQUENCE: 59

His Tyr Ser Leu Cys Ser Ala Ser Thr Lys
 1               5                  10

<210> SEQ ID NO 60
<211> LENGTH: 14
<212> TYPE: PRT
<213> ORGANISM: rabbit
<220> FEATURE:
<221> NAME/KEY: VARIANT
<222> LOCATION: (13)
<223> OTHER INFORMATION: C at position 13 is ICAT-labeled cysteinyl
      residue.

<400> SEQUENCE: 60

Val Pro Thr Pro Asn Val Ser Val Val Asp Leu Thr Cys Arg
 1               5                  10

<210> SEQ ID NO 61
<211> LENGTH: 18
<212> TYPE: PRT
```

```
<213> ORGANISM: Streptomyces lividans

<400> SEQUENCE: 61

Leu Gly Lys Pro Val Leu Thr Ala Asn Gln Val Thr Ile Trp Glu Gly
 1               5                  10                  15

Leu Arg

<210> SEQ ID NO 62
<211> LENGTH: 19
<212> TYPE: PRT
<213> ORGANISM: Unknown
<220> FEATURE:
<223> OTHER INFORMATION: Description of Unknown Organism: Unidentifed

<400> SEQUENCE: 62

Ile Ala Asn Pro Asn Val Tyr Thr Glu Thr Leu Thr Ala Ala Thr Val
 1               5                  10                  15

Cys Thr Ile

<210> SEQ ID NO 63
<211> LENGTH: 19
<212> TYPE: PRT
<213> ORGANISM: Unknown
<220> FEATURE:
<223> OTHER INFORMATION: Description of Unknown Organism: Unidentifed

<400> SEQUENCE: 63

Leu Ala Leu Leu Pro Ser Asp Ala Glu Gly Pro His Gly Gln Phe Val
 1               5                  10                  15

Thr Asp Lys

<210> SEQ ID NO 64
<211> LENGTH: 20
<212> TYPE: PRT
<213> ORGANISM: Homo sapiens

<400> SEQUENCE: 64

Ala Leu Leu Val Leu Val Ala Pro Ala Met Ala Ala Gly Asn Gly Glu
 1               5                  10                  15

Asp Leu Arg Asn
            20
```